United States Patent
Yang et al.

(10) Patent No.: US 10,550,176 B2
(45) Date of Patent: Feb. 4, 2020

(54) VIRAL VECTORS ENCODING MULTIPLE HIGHLY HOMOLOGOUS NON-VIRAL POLYPEPTIDES AND THE USE OF SAME

(71) Applicant: Roger Williams Hospital, Providence, RI (US)

(72) Inventors: Wen Yang, Sharon, MA (US); Richard P. Junghans, Boston, MA (US); Anthony J. Bais, Providence, RI (US)

(73) Assignee: ROGER WILLIAMS MEDICAL CENTER, Providence, RI (US)

( * ) Notice: Subject to any disclaimer, the term of this patent is extended or adjusted under 35 U.S.C. 154(b) by 0 days.

(21) Appl. No.: 14/960,236

(22) Filed: Dec. 4, 2015

(65) Prior Publication Data

US 2016/0083462 A1    Mar. 24, 2016

Related U.S. Application Data

(62) Division of application No. 13/145,488, filed as application No. PCT/US2010/021825 on Jan. 22, 2010, now Pat. No. 9,206,440.

(60) Provisional application No. 61/146,755, filed on Jan. 23, 2009.

(51) Int. Cl.

| C07K 16/18 | (2006.01) |
|---|---|
| C12N 15/86 | (2006.01) |
| C07K 14/725 | (2006.01) |
| C07K 14/705 | (2006.01) |
| C07K 16/08 | (2006.01) |
| C07K 16/40 | (2006.01) |
| C12N 7/00 | (2006.01) |
| A61K 35/00 | (2006.01) |
| A61K 38/00 | (2006.01) |
| A61K 48/00 | (2006.01) |

(52) U.S. Cl.
CPC .......... *C07K 16/18* (2013.01); *C07K 14/7051* (2013.01); *C07K 14/70521* (2013.01); *C07K 16/084* (2013.01); *C07K 16/40* (2013.01); *C12N 7/00* (2013.01); *C12N 15/86* (2013.01); *A61K 35/00* (2013.01); *A61K 38/00* (2013.01); *A61K 48/00* (2013.01); *C07K 2317/622* (2013.01); *C07K 2319/70* (2013.01); *C12N 2740/10032* (2013.01); *C12N 2740/10052* (2013.01); *C12N 2740/13043* (2013.01); *C12N 2740/13045* (2013.01); *C12N 2810/855* (2013.01); *C12N 2810/859* (2013.01)

(58) Field of Classification Search
None
See application file for complete search history.

(56) References Cited

U.S. PATENT DOCUMENTS

| 6,410,298 | B1 | 6/2002 | Crouzet et al. |
|---|---|---|---|
| 8,337,859 | B2 | 12/2012 | Silvestre et al. |
| 9,206,440 | B2 | 12/2015 | Yang et al. |
| 2003/0152559 | A1 | 8/2003 | Yang et al. |
| 2006/0292682 | A1 | 12/2006 | Hawkins et al. |
| 2008/0153770 | A1* | 6/2008 | Kim ............... C12N 15/86 514/44 R |
| 2012/0134970 | A1 | 5/2012 | Yang et al. |

FOREIGN PATENT DOCUMENTS

WO    WO 2007046787 A2 *    4/2007    ............. C07H 21/04

OTHER PUBLICATIONS

Willemsen et al. Genetic Engineering of T Cell Specificity for Immunotherapy of Cancer. Human Immunology, 2003. 64:56-68.*
Weissman et al. "Molecular Cloning and Chromosomal Localization of the human T-cell receptor Zeta Chain: Distinction from the Molecular CD3 complex" PNAS, 1988 (85):9709-9713.*
Laczkó et al, Conformational Effect of Phosphorylation on T Cell Receptor/CD3ζ-Chain Sequences. Biochemical and Biophysical Research Communications, 1998 (242): 474-479.*
International Search Report from PCT Patent Application No. PCT/US2010/021825 dated Jul. 30, 2010, application published as int. Publication No. WO2012/085660 dated Jul. 29, 2010.
International Preliminary Report on Patentability and Written Opinion from PCT Patent Application No. PCT/US2010/021825 dated Jul. 26, 2011, application published as International Publication No. WO2012/085660 dated Jul. 29, 2010.
Maher et al., "Human T-lymphocyte cytotoxicity and proliferation directed by a single chimeric TCRzeta /CD28 receptor", Nat. Biotechnol., vol. 20, No. 1, pp. 70-75 (2002).

(Continued)

*Primary Examiner* — Christopher M Babic
*Assistant Examiner* — Kimberly A. Aron
(74) *Attorney, Agent, or Firm* — McDermott Will & Emery LLP

(57) ABSTRACT

The present invention relates to compositions and methods for creation of vector nucleic acid sequences (e.g., retroviral nucleic acid sequences) that comprise two or more exogenous nucleic acid sequences that encode highly homologous (e.g., identical) polypeptide sequences, yet wherein at least one of the exogenous nucleic acid sequences has been mutated using degenerate codons for purpose of reducing homology between the two or more exogenous nucleic acid sequences while maintaining the encoded polypeptide sequence. Preferred nucleic acid sequences include those encoding multi-chimeric immune receptor (CIR) genes. Specific nucleic acid sequences of such CIR genes are also disclosed.

19 Claims, 42 Drawing Sheets

Specification includes a Sequence Listing.

(56) References Cited

OTHER PUBLICATIONS

Sadelain et al, "The promise and potential pitfalls of chimeric antigen receptors", Curr. Opin. Immunol., vol. 21, No. 2, pp. 215-223 (2009).

Szymczak et al., "Correction of multi-gene deficiency in vivo using a single 'self-cleaving' 2A peptide-based retroviral vector", Nat. Biotechnol., vol. 22, No. 5, pp. 589-594 (2004).

Wilkie et al., "Retargeting of human T cells to tumor-associated MUC1: the evolution of a chimeric antigen receplor", J. Immunol., vol. 180, No. 7, pp. 4901-4909 (2008).

Yang et al., "Chimeric immune receptors (CIRs) specific to JC virus for immunotherapy in progressive multifocal leukoencephalopathy (PML)", Int. Immunol., vol. 19, No. 9, pp. 1083-1093 (2007).

Yang et al., "Creating Retroviral Vector Encoding Two Homologous Chimeric Immune Receptors with Degenerated Codons", J. Immunol., vol. 178, Abstract #17.28, 2 pages (2007), online article downloaded from http://www.iimmunol.org/cgi/content/meeting_abstract/178/MeetingAbstracts/178/S71-d on Jun. 21, 2010.

\* cited by examiner

FIG. 1

```
1    ttggatcctaagtttatgttattagacgggatttattatacggagtgatatta   60
     L  D  P  K  L  C  Y  L  L  D  G  I  L  F  I  Y  G  V  I  L 61   acagcgctattttacgtgtcaaatttcacgctccgctgatgcgccgctatcaacaa  120
     T  A  L  F  L  R  V  K  F  S  R  S  A  D  A  P  A  Y  Q  Q 121  gggcaaaatcaattgtacaatgaattgggtcgtagagaagaatgacgtactc     180
     G  Q  N  Q  L  Y  N  E  L  N  L  G  R  R  E  E  Y  D  V  L 181  gataaacggagggggcgcgatccagaaatgggcggcaaaccacggcgaaaaatccacaa  240
     D  K  R  R  G  R  D  P  E  M  G  G  K  P  R  R  K  N  P  Q 241  gagggattatataacgagttacaaaggacaaaatgcagaagcatattcagaaataggt  300
     E  G  L  Y  N  E  L  Q  K  D  K  M  A  E  A  Y  S  E  I  G 301  atgaaggggaaaggagacgaggaaaggtcatgacgattgtatcaaggattatcgacc  360
     M  K  G  E  R  R  R  G  K  G  H  D  G  L  Y  Q  G  L  S  T 361  gcgactaaagatacgtatgatgcgttacacatgcaagcattaccgccaagataa   414 (SEQ ID NO:1)
     A  T  K  D  T  Y  D  A  L  H  M  Q  A  L  P  P  R  *        (SEQ ID NO:2)
```

FIG. 2

```
Mutated partial CD3ζ  TTGGATCCCTAAGTTATGTTATTTATTAGACGGGATTTTATTTATATACGG
Partial CD3ζ          CTGGATCCCCAAACTCTGCTACCTGCTGGATGGAATCCTCTTCATCTATGG
                      * ******  ** ** ** *  * ***  * *** ** ** *** ** **

Mutated partial CD3ζ  AGTGATATTAACAGCGCTATTTTTACGTGTCAAATTTTCACGCTCCGCTG
Partial CD3ζ          TGTCATTCTCACTGCCTTGTCCTTGAGAGTGAAGTTCAGCAGGAGCGCAG
                      ** ** * * *   *  *  * ** * * * ***   *  *  ***

Mutated partial CD3ζ  ATGCGCCGGCCTATCAACAAGGGCAAAATCAATTGTACAATGAATTGAAC
Partial CD3ζ          ACGCCCCGCGTACCAGCAGGGCCAGAACCAGCTCTATAACGAGCTCAAT
                      * *** *** *  ** ***** * ** *  * ***  ***   ** **

Mutated partial CD3ζ  TTGGGTCGTAGAGAAGAATATGACGTACTCGATAAACGGAGGGGGCGA
Partial CD3ζ          CTAGGACGAAGAGAGAGGAGTACGATGTTTTGGACAAGAGACGTGGCCGGGA
                      * ***   * ** *  *  *   **  * ***     **  **  * **

Mutated partial CD3ζ  TCCAGAAATGGGCGGCAAACCACGGCGAAAAATCCACAAGAGGATTAT
Partial CD3ζ          CCCTGAGATGGGGGAAAGCCGAGAAGAAGAACCCTCAGGAAGGCCCTGT
                      *  * ** ****   * * ** * ***  *  ** ** *** * *  *

Mutated partial CD3ζ  ATAACGAGTTACAAAAGGACAAAATGGCAGAAGCATATTCAGAAATAGGT
Partial CD3ζ          ACAATGAACTGCAGAAAGATAAGATGGCGGAGGCCTACAGTGAGATTGGG
                      * ** ***  * * ** ** *  ***** ** ** ** ** * ** **
```

FIG. 2 (continued)

```
Mutated partial CD3ζ    ATGAAGGGGGGAAGGAGAGACGAGGGAAAGGTTCATGACGGATTGTATCAAGG
Partial CD3ζ            ATGAAAGGGCGAGCGCCGGAGGGGCAAGGGCACGATGGCCCTTTACCAGGG
                        *****  **  *   *  *  *  * ***  ** ** ** **  ** ***

Mutated partial CD3ζ    ATTATCGACCGCGACTAAAGATACGTATGATGCGTTACACATGCAAGCAT
Partial CD3ζ            TCTCAGTACAGCCACCAAGGACCACCTACGACGCCCTTCACATGCAGGCCC
                         *   ** *** *     * **  ** ** **   *  * ******** **

Mutated partial CD3ζ    TACCGCCAAGATAA      (SEQ ID NO:1)
Partial CD3ζ            TGCCCCCTCGCTAA      (SEQ ID NO:3)
                        * ** ** ** ***
```

FIG. 3

```
1    cctaggaagatcgaggtaatgtaccaccgcccctatctcgataacgaaaaagtaacggt      60
     P  R  K  I  E  V  M  Y  P  P  P  Y  L  D  N  E  K  S  N  G 61   acaataattcacgttaagggaaagcattatgcccttccccgttgttcccgggcccaagc    120
     T  I  I  H  V  K  G  K  H  L  C  P  S  P  L  F  P  G  P  S
```

FIG. 3 (continued)

```
121 aaacgttctgggttctcgtagttgtaggcggtgttgttagcatgttactctctccttgtt   180
    K  P  F  W  V  L  V  V  V  G  G  V  L  A  C  Y  S  L  L  V 181 acagtagctttcataatctttggtccgatcaaacgctctcgattgttacattccgat      240
    T  V  A  F  I  I  F  W  V  R  S  K  R  S  R  L  L  H  S  D 241 tatatgaatatgacaccgagagacctggcccgacgaggaaacactatcaaccgtacgca     300
    Y  M  N  M  T  P  R  R  P  G  P  T  R  K  H  Y  Q  P  Y  A 301 cctccgagagattttgctgcgtacaggagtcgtgtcaaatttcacgctccgctgatgcg    360
    P  P  R  D  F  A  A  Y  R  S  R  V  K  F  S  R  S  A  D  A 361 ccggcctatcaacaaggcaaaatcaattgtacaatgaattgaactttgggtcgtagagaa   420
    P  A  Y  Q  Q  G  Q  N  Q  L  Y  N  E  L  N  L  G  R  R  E 421 gaatatgacgtactcgataacgagggggcgcgatccagagaaatgggcggcaaaccacgg   480
    E  Y  D  V  L  D  K  R  R  G  R  D  P  E  M  G  G  K  P  R 481 cgaaaaaatccacaagaggggattatatcgagttacaaaggacaaaatggcagaagca     540
    R  K  N  P  Q  E  G  L  Y  N  E  L  Q  K  D  K  M  A  E  A 541 tattcagaaataggtatgaaggggaagagagacgagggaaaggtcatgacggattgtat    600
    Y  S  E  I  G  M  K  G  E  R  R  R  G  K  G  H  D  G  L  Y 601 caaggattatcgaccgcgactaaagatacgtatgatgcgttacacacatgcaagcattaccg 660
    Q  G  L  S  T  A  T  K  D  T  Y  D  A  L  H  M  Q  A  L  P 661 ccaagataa  (SEQ ID NO:4)                                        669
    P  R  *   (SEQ ID NO:5)
```

FIG. 4

```
Mutated CD28CD3ζ  CCTAGGAAGATCGAGGTAATGTACCCACCGCCCTATCTCGATAACGAAAA    50
CD28CD3ζ          CCTAGGAAAATTGAAGTTATGTATCCTCCTCCTTACCTAGACAATGAGAA
                  **********  ***** ** ******* **** ** *** *** ****

Mutated CD28CD3ζ  AAGTAACGGTACAATAATTCACGTTAAGGGAAAGCATTTATGCCCTTCCC   100
CD28CD3ζ          GAGCAATGGAACCATTATCCATGTGAAAGGAAACACCTTTGTCCAAGTC
                   ** ** ***  ** *  **  ** ** ****** **  ** ** * *

Mutated CD28CD3ζ  CGTTGTTCCCGGGCCCAAGCAAACCGTTCTGGGTTCTCGTAGTGTAGGC   150
CD28CD3ζ          CCCTATTTCCCGGACCTTCTAAGCCCTTTTTGGGTGCTGGTGGTGGTGGT
                  *   * ** *** **  * *** **  *  *****  * ** ** **

Mutated CD28CD3ζ  GGTGTGTTAGCATGTTACTCTCCTTGTTACAGTAGCTTTCATAATCTT   200
CD28CD3ζ          GGAGTCCTGGCTTGCTATAGTTGCTAGTAACAGTGGCCTTTATTATTTT
                  ** ** * * **  *     * *  **  ** ** **  *** *  **

Mutated CD28CD3ζ  TTGGGTCCGATCAAAACGCTCTCGATTGTTACATTCCGATTATATGAATA   250
CD28CD3ζ          CTGGGTGAGGAGTAAGAGGAGCAGGCTCCTGCACAGTGACTACATGAACA
                   *****   *   *    *  **  *   *  ** ** ** ******

Mutated CD28CD3ζ  TGACACCGAGGAGACCTGGCCCGACGAGGAAAACACTATCAACCGTACCA   300
CD28CD3ζ          TGACTCCCCCGCCCGGCCCCCGCCCAAGCATTACCAGCCCTATGCC
                  **** **  **  *   * ****  ****     *   **  ****

Mutated CD28CD3ζ  CCTCCGAGAGATTTTGCTGCGTACAGGAGTCGTGTCAAATTTTCACGCTC   350
CD28CD3ζ          CCACCACGCGACTTCGCAGCCTATGCGCTCCAGAGTCGAAGTTCAGGAG
                  ** *  ** ** *   *   **    *   ** *  **  ****  *
```

FIG. 4 (continued)

```
Mutated CD28CD3ζ  CGCTGATGCGGCCGGCCTATCAACAAGGGCAAAATCAATTGTACAATGAAT    400
CD28CD3ζ          CGCAGAGACGCCCCCGCGTACCAGCAGGGCCAGAACCAGCTCTATAACGAGC
                  **    *    *   **  ** * **   **   ** * ** **  ** *

Mutated CD28CD3ζ  TGAACTTGGGTCGTAGAGAAGAATATGACGTACTCGATAAACGGAGGGGG     450
CD28CD3ζ          TCAATCTAGGACGAAGAGAGGAGTACGATGTTTTTGGACAAGAGACTGGC
                  * ** * ***  * *** ** ** ** ** *      ** * **  ***

Mutated CD28CD3ζ  CGCGATCCAGAAATGGGGCGGCCAAACCACGGCGAAAAAATCCACAAGAGGG   500
CD28CD3ζ          CGGGACCCCTGAGATGGGGGAAAGCCGAGAAGGAAGAACCCTCAGGAAGG
                   * ** ** * *** ****   *** **   ** *** * * ** ** **

Mutated CD28CD3ζ  ATTATATAACGAGTTACAAAAGGACAAAATGGCAGAAGCATATATTCAGAAA    550
CD28CD3ζ          CCTGTACAATGAACTGCAGAAAGATAAGATGGCGGAGGCCTACAGTGAGA
                   * * *  ** ** * ** ****  **  ***** *** ** * ** ***

Mutated CD28CD3ζ  TAGGTATGAAGGGGGCGAGGGAAAGAGACGAGGGGAAAGGTCATGACGGATTGTAT    600
CD28CD3ζ          TTGGGATGAAAGGGCGAGGGCCGAGGGCACGAGGGCAAGGGCACGATGGCCTTTAC
                   ** ***** ***** ****    * **  **  **** ** **   * * **

Mutated CD28CD3ζ  CAAGGATTATCGACCGCGACTAAAGATACGTATGATGCGTTACACATGCA      650
CD28CD3ζ          CAGGGTCTCAGTACAGCCACCAAGGACACACCTACGACGCCCTTCACATGCA
                  **  * *  ** ** * ** **   ** ** ** * ** *  * *******

Mutated CD28CD3ζ  AGCATTACCGCCCAAGATAA    (SEQ ID NO:4)                  669
CD28CD3ζ          GGCCCTGCCCCCCTGCTAA    (SEQ ID NO:6)
                   ** **  * **  * ***
```

FIG. 5

```
1    cctcaattatgttacatattagacgcgatttcttatacgggatcgtttaacatta    60
     P  Q  L  C  Y  I  L  D  A  I  L  F  L  Y  G  I  V  L  T  L 61   ttatattgccgtttaaaattcaggttcggaaagccgcgatcacttcatacgaaaagagc   120
     L  Y  C  R  L  K  I  Q  V  R  K  A  A  I  T  S  Y  E  K  S 121  gacggcgtgtatacaggtttatcaacacgaaatcaagaaaacgtatgaaacctaaaacac  180
     D  G  V  Y  T  G  L  S  T  R  N  Q  E  T  Y  E  T  L  K  H 181  gaaaagcccctcaatag                                            198
     E  K  P  P  Q  *
```

(SEQ ID NO:7)
(SEQ ID NO:8)

FIG. 6

```
Mutated hFcεRIγ      ------------------------------------------------
hFcεRIγ M33195.1     CAGAACGGCCGATCTCCAGCCCAAGATGATTCCAGCAGTGGTCTTGCTCTTACTCCTTTT Mutated hFcεRIγ      ----------------CCTCAATTATGTTACATATATTAGACGCGATTTT
hFcεRIγ M33195.1     GGTTGAACAAGCAGCGGCCCTGGGAGAGCCTCAGCTCTGCTATATCCTGGATGCCATCCT
                                     *****  *  ** ** ** ** *

Mutated hFcεRIγ      ATTCTTATACGGGATCGTTTTAACATTATTATATTGCCGTTAAAAATTCAGGTTCGGAA
hFcεRIγ M33195.1     GTTTCTGTATGGAATTGTCCTCACCCTCCTCTACTGTCGAAGATCCAAGTGCGAAA
                     **  * *** **  ** ** ** *   *  *   *   **  ** ** ** ** **

Mutated hFcεRIγ      AGCCGCGATCACTTCATACGAAAAGAGCGACGGCGTGTATACAGGTTTATCAACACGAAA
hFcεRIγ M33195 1     GGCAGCTATAACCAGCTATGAGAAATCAGATGGTGTTTACACGGGCCTGAGCACCAGGAA
                     **  * *** **    ** *** **    ** **  ** ** * *   **    ** **

Mutated hFcεRIγ      TCAAGAAACGTATGAAACCTTAAAACACGAAAAGCCCCCTCAATAG-----------
hFcεRIγ M33195.1     CCAGGAGACTTACGAGACTCTGAAGCATGAGAAACCACCAGTAGCTTTAGAATAGATG
                     ** ** ** ** ** **  *   ** ** ** ** ** ** ***
```

Mutated hFcεRIγ
(SEQ ID NO:7)
hFcεRIγ M33195.1
(SEQ ID NO:9)

FIG. 12

Anti-p36 TCRα sequence-GGGGATCTGGATCCCAAACTCTGCTGCTGGATGGAATCCTCTTC
ATCTATGGTGTCATTCTCACTGCCTTGTTCCTGAGAGTGAAGTTCAGCAGGAGCGCAGACGCCCCGTACCAG
CAGGGCCAGAACCAGTCTCTATAACGAGCTCAATCTAGGACGAAGAGAGAAGTACGATGTTTTGACAAGAGACGT
GGCCCGGGACCCTGAGATGGGGGAAAGCCGAGAAGAAGAACCCTCAGGAAGGCCTGTACAATGAACTGCAGAAA
GATAAGATGGCGGAGGCCTACAGTGAGATTGGGATGAAAGGCGCAAGGGCGCAAGGGCACGATGGCCTT
TACCAGGGTCTCAGTACAGCCACCAAGGACACCTACGACGCCCCTTCACATGCAGCCCCTGCCCCCTCGCTAA (SEQ ID NO:10)

FIG. 14

Anti-p36 TCRβ sequence-GGGGATCTGGATCCCAAACTCTGCTACCTGCTGCTGGATGGAATCCTCTTCATCTAT
GGTGTCATTCTCACTGCCTTGTTCCTGAGAGTGAAGTTCAGCAGGAGCGCAGACGCCCCGTACCAGCAGGGCCAGAAC
CAGTCTCTATAACGAGCTCAATCTAGGACGAAGAGAGAAGTACGATGTTTTGACAAGAGACGTGGCCGGGACCCTGAGATG
GGGGAAAGCCGAGAAGGAAGAAACCCTCAGGAAGGCCTGTACAATGAACTGCAGAAAGATAAGATGGCGGAGGCCTACAGT
GAGATTGGGATGAAAGGCGCAAGGGCACGATGGCCTTTACCAGGGTCTCAGTACAGCCACCAAGGAC
ACCTACGACGCCCCTTCACATGCAGCCCCTGCCCCCTCGCTAA (SEQ ID NO:13)

FIG. 13

```
                                        -----------Anti-p36 TCRα sequence-
                                        ----amino acids encoded by anti-p36 TCRα sequence-
                                                                                                    TM of CD3ζ
ggggatctggatcccaaactctgctacctgctgatggaatcctcttcatctatggt
 G  D  L  D  P  K  L  C  Y  L  L  D  G  I  L  F  I  Y  G gtcattctcactgcctgttcctgagagtgaagttcagcaggagcgcagacgccccgcg
 V  I  L  T  A  L  F  L  R  V  K  F  S  R  S  A  D  A  P  A taccagcagggccagaaccagtctctataacgagctcaatctaggacgaagagagtac
 Y  Q  Q  G  Q  N  Q  L  Y  N  E  L  N  L  G  R  R  E  E  Y gatgttttggacaagagacgtggccgggacccctgagatgggggggaaagccgagaaggaag
 D  V  L  D  K  R  R  G  R  D  P  E  M  G  G  K  P  R  R  K aaccctcaggaaggcctgtacaatgaactgcagaaagataagatggcggaggcctacagt
 N  P  Q  E  G  L  Y  N  E  L  Q  K  D  K  M  A  E  A  Y  S gagattgggatgaaaggcgagcgccgaagggggcaagggggcacgatggccttaccagggt
 E  I  G  M  K  G  E  R  R  R  G  K  H  D  G  L  Y  Q  G ctcagtacagcaccaaggacacctacgacgccctcacatgcaggccctgccccctcgc
 L  S  T  A  T  K  D  T  Y  D  A  L  H  M  Q  A  L  P  P  R taa   (SEQ ID NO:11)
 *    (SEQ ID NO:12)
```

FIG. 15

```
--------Anti-p36 TCRβ sequence-ggggatctggatccaaactctgctac
-Anti-p36 TCRβ encoded amino acids--G D L D P K L C Y ctgctggatggaatcctcttcatctatggtgtcattctcactgcctgttcctgagagtg
 L  L  D  G  I  L  F  F  I  Y  G  V  I  L  T  A  L  F  L  R  V aagttcagcaggagcgcagacgcgccccccgctaccaggccagaaccagtctctataac
 K  F  S  R  S  A  E  P  P  A  Y  Q  Q  G  Q  N  Q  L  Y  N gagctcaatctaggacgagagagaggagtacgatgttttggacaagagacgtggccgggac
 E  L  N  L  G  R  R  E  E  Y  D  V  L  D  K  R  R  G  R  D cctgagatgggggggaaagccgagggcctacagtgagattgggatgaaaggcgagccggagg
 P  E  M  G  G  K  P  R  R  K  N  P  Q  E  G  L  Y  N  E  L cagaaagataagatggcggaggcctacagtgagattgggatgaaaggcgagccggagg
 Q  K  D  K  M  A  E  A  Y  S  E  I  G  M  K  G  E  R  R  R ggcaaggggcacgatgggctttaccagggtctcagtacagccaccaaggacacctacgac
 G  K  G  H  D  G  L  Y  Q  G  L  S  T  A  T  K  D  T  Y  D cccttcacatgcaggccctgcccctcgctaa      (SEQ ID NO:14)
 A  L  H  M  Q  A  L  P  P  R  *     (SEQ ID NO:15)
```

FIG. 16

Anti-p36 TCRβ sequence-GGGGATCTGGATCCAAACTCTGCTACCTGCTGGATGGAATCCTCTTCATCTATGGTGTCATTCTCACTGCCTGTTCCTGAGAGTGAAGTTCAGCAGGAGCGCAGAGCCGCCTATCAACAAGGCCAAAATCAATTGTACAATGAATTGAACTTGGGTCGTAGAGAAGAATATGACGTTCTCGATAAACGGAGGGGCCGAGATCCAGAGAATGGGCGGCAAAACCACGGCGAAAAATCCACAGAAGAGGATTATAACGAGTTACAAAAATGGCAGAAGCATATTCAGAAGAATATGCCGTATGAAGGGGAAAGGACGAGGAAAGTTCATGACGATTGTATCAAGGATTATCGACCGCGACTAAAGATACCGTATGATGCGTTACACATGCAAGCATTACCGCCAAGATAA (SEQ ID NO:16)

FIG. 17

Anti-p36 TCRα sequence-<u>CCTAGGAAAAATTGAAGTTATGTATCCTCCTCCTTACCTAGACAATGAGAAGAGC</u>
AATGGAAGCATTATCCATGTGAAAGGGAAACACCCTTTGTCCAAGTCCCCGACCTTCTAAGCCCTTTGGGTG
CTGGTGGTTGGTTGGTGGAGTCCTGGCTTGCTAGTAGCTTGCTAGTAACAGTGCCTTTATTATTTCTGGGTGAGGAGTAAG
AGGAGCAGGCTCCTGCACAGTGACTACAGACATGAACTCCCCGCGCAGTCCCCGCAAGCATTACCAGCCCTAT
GCCCCACCGCGACTTCGCAGCCTATCGCTCCTCCAGAGTGAAGTTCAGGAGGAGTACGATGTTTTGGACAGAGACGTGGCCGGACCCT
CAGAACCAGCTCTATACGAGCTCAATCTAGGACGAAGAAGAAGAACCCTCAGGAAGGGCGCGAGAAGGGGAGGGCCAGGGCCGGGAGAGCC
GAGATGGGGGAAAGCCGAGAATGGGATGAAAGGCGAGCGCCGGAGGGCGAGGGCGCCCAAGGGCACGATGGCCTTTACCCAGGGTCTCAGTACAGCCACC
AAGGACACCTACGACGCCCCTTCACATGCAGCGCAGCGCCCCCTGCCCCTCGCTAA (SEQ ID NO:17)

FIG. 19

Anti-p36 TCRβ sequence-<u>CCTAGGAAGAAGATCGAGGTAATGTACCCACCGCCCTATCTCGATAACGA</u>
AAAAGTAACGGTACAATAATTCACGTTAAGGGAAAAGCATTATGCCCTTCCCGTTGTCCCGGCCCA
AGCAAACCGTTTGGGTTCTCGTAGTTGTAGGCGGTGTGTTAGCATGTGTTACTCTCTCCTTGTTACAGTAG
CTTTCATAATCTTTTGGGTCCCGATCAAAACGCTTCGATTGTTACATTCCGATTATATGAATATGACACC
GAGGAGACCTGGCCCGACGAGACAAAACACTATCAACGCCGCCTATCAACAAGGCAGATTTTGCTGCGTACAGG
AGTCGTGTCAAATTTCACGCTCCGCTGATGCCGCCTATCAACAAGGCGAGGGCAAAATCAATTGTACAATG
AATTGAACTTGGGTCGTAGAGAAGAATATGACGTACTCGATAATAACGAGGGCCGATCCAGAAATGGG
CGGCAAACCACGCGAAATTCAGAGGGATTATATACCACGAGTTACAAAGGACAAAATGGCAGAA
GCATATTCAGAATAGTATGAAGGGGAAAGGTCATGACGGATTGTATCAAGAT
TATCGACCGCGACTAAAGATACGTATGATCGCTTACACATGCAAGCATTACCGCCAAGATAA (SEQ ID NO:20)

FIG. 18

---------------Anti-p36 TCRα sequence-
---------amino acids encoded by anti-p36 TCRα sequencecctaggaaaattgaagttatgtatcctccttactagacaatgagagagcaatgga
P  R  K  I  E  V  M  Y  P  P  P  Y  L  D  N  E  K  S  N  G accattatccatgtgaaagggaaacacctttgtccaagtccccctatttccggacctct
T  I  I  H  V  K  G  K  H  L  C  P  S  P  L  F  P  P  G  P  S aagcccttttgggtgctgtgtgtggttggtggagtcctggcttgctatagcttgctagta
K  P  F  W  V  <u>L  V  V  V  G  G  V  L  A  C  Y  S  L  L  V</u> acagtggcctttattatttttctggggtgagagtaagaagaggagcaggctcctgcacagtgac     CD/<u>TM</u>/CY of CD28
<u>T  V  A  F  I  I  F  W  V  R  S  K  R</u>  S  R  L  L  H  S  D tacatgaacatgactccccgcccccggcccccgggcccaagcattaccagccctatgcc
Y  M  N  M  T  P  R  R  P  G  P  T  R  K  H  Y  Q  P  Y  A ccaccacgcgacttcgcagcctatcgctcccagagtgaagttcagcaggagcagagacgcc
P  P  R  D  F  A  A  Y  R  S  R  V  K  F  S  R  S  A  D  A FIG. 18 (continued)

Cy of CD3ζ cccgcgtaccagcaggccagaaccagctctataacgagctcaatctaggacgaagagag
 P  A  Y  Q  Q  G  Q  N  Q  L  Y  N  E  L  N  L  G  R  R  E gagtacgatgtttggacaagagacgtggccgggacccctgagatgggggaaagccgaga
 E  Y  D  V  L  D  K  R  R  G  R  D  P  E  M  G  G  K  P  R aggaagaaccctcaggaaggcctgtacaatgaactgcagaaagataagatggcggaggcc
 R  K  N  P  Q  E  G  L  Y  N  E  L  Q  K  D  K  M  A  E  A tacagtgagattgggatgaaaggcgagcgccggagggggcaagggggcacgatggcctttac
 Y  S  E  I  G  M  K  G  E  R  R  R  G  K  G  H  D  G  L  Y cagggtctcagtacagccaccaaggacacctacgacgccctccacatgcaggccctgccc
 Q  G  L  S  T  A  T  K  D  T  Y  D  A  L  H  M  Q  A  L  P cctcgctaa   (SEQ ID NO:18)
 P  R  *    (SEQ ID NO:19)

FIG. 20

ATGAACCGGGAGTCCCTTTTAGGCACTTGCTTCTGTGCTGCAACTGGCGTCCTCCCAGCAGCCACTC
AGGGAAAGAAAGTGGTGCTGGGCAAAAAAACTCCAACCAGATACAGTGGAACTGTACAGCTTCCCAGAAGAA
GAGCATACAATTCCACTGGAAAAAATCTGAATGATCGCGCTGACTCAAGAAGATTCTGGAAATCAGGCTCCTTCTTAACT
AAAGGTCCATCCAAGCTTGAATGATCGCGCTGACTCAAGAAGAAGCCTTTGGACCAAGGAAACTTTCCCC
TGATCATCAAGAATCTTAAGATAGAAGACTCAGATACTTACATCTGTGAAGTGGAGGACCAGAAGGAGGA
GGTGCAATTGCTAGTGTTCGGATTGACTGCCAACTCTGACACCACCACCTGCTTCAGGGCAGAGCCTGACC
CTGACCTTGGAGAGCCCCCCTGGTAGTAGCCCCTCAGTGCAATGTAGGAGTCAAGGGTAAAACATAC
AGGGGGAAGACCCTCTCCGTGTCTGGAGTTCAAAATAGACATCGTGGTGCTAGCTTTCCAGAAGGCCTCCAGCATA
GCAGAACCAGAAGAAGTGGAGTGGAGGGGAACAGTGGCAGGCGGAGAGGGCTTCCTCCTCCAAGTCTTGGATCACTTTGACCTGAA
GTCTATAAGAAGAGAAAGAGGGGAACAGTGGCAGGCGGAGAGGGCTTCCTCCTCCAAGTCTTGGATCACTTTGACCTGAA
GCAGTGGCGAGCTGTGTGGCAGGCGGAGAGGGCTTACCCAGGACCCTAAGCTCCAGGATGGGCAAGAAGCTCCCGCTC
GAACAAGAAGTGCTGTAAAACGGGTTGCCTCAGTAACCGGGTTGCCTCAGTATGCTGGCTGTGATGAGAACCTCAGCTCCCTTGAAGCGA
CACCTCACCCTGCCCCAGGCCTTGCCCCAGGCCTTGCCTCAGTATGCTGGCTGTGATGAGAACCTCAGCTCCCTTGAAGCGA
AAACAGGAAAGTTGCATCAGGAGACCCACCTCCCCTAAGCTGAACCTGCCTCAGTATGCTGGCTGTGATGAGAACCTCAGCTCCCTTGAAGCGA
AAACAGGAAAGTTGCATCAGGAGACCCACCTCCCCTAAGCTGAACCTGGGTGAACCCTGGGTGCTGAACCCTGGGTGCTGAACCCTGAGTG
CTGTGAGGTGTGGGGAGCGGAGAAGCGGTGGGTGCTGAACCCTGGGTGCTGTGCTGTGCTGAGTG
GTCTCGAAGCGGACAGGTCCTGCTGGAATCCAACATCAAGGTTCTGCCCACCCCCGGTGTCCACCCCCGGTGTGCTGCAGCCAATG
ACTCGGGACAGGTCCTGCTGGAATCCAACATCAAGGTTCTGCCCACCCCCGGTGTCCACCCCCGGTGTGCTGCAGCCAATG (SEQ ID NO: 21)

FIG 21

ATGAACCGAGGGGTGCCATTCAGACACATTTGCTGCTTGTCCTCCAGCTTGCCCTGCTTCCTGCCGCAACTC
AAGGAAAAAAGGTCGTCCTCGGGAAGAAGGAGACACTGTTGAGCTAACATGCACTGCATGCAAAAGAAGAGTA
TTCAGTTTCATTGGAAGAATCAAATCAAATACTCGGTAACCAAGGTCGTTTTGACAAAGGG
ACCTTCGAAACTCAACGACCGGCAGATTCTAGGAGAAGTCTATGGGATCAGGTAATTCCCGCTCATA
ATAAAAACCTAAAAATTGAGGATTCTGACACATATATTTGCGAGGTCGAAGATCAAAAGAAGAAGTCC
AGTTACTTGTCTTTGGTTTAACAGCGAATTCAGATACGCCATCTCCTACAAGGCCAAAGTCTCACGCTCAC
GTTAGAAAGTCCGCCAGGAAGCAGTCCGTCGTCCAGTGCAAGACAGCGGGACTTGTACAGTGTTACAAA
GGCAAAACGCTGTCGTCTCACAACTCGAACTGCAAGACAGCGGGACTGCATTTCAAAAGCGTCGAGTATTGTGTA
ATCAAAAAGGTCGAATTTAAGATTGATATAGTCGTCCTTGCCGTTTCCTCGGCGTTCACTGTAGAGAAACTCACCGGAGC
CAAAAGGAAGGCGAGCAAGTCAAGTCGAATTTTCGTTTCCTCGGCGTTCACTGTAGAGAAACTCACCGGAGC
GGGGAACTCTGGTGGCAAGCGGAAAGAGCATCGTCGTCGAAATCATGATTACGTTCGATCTCAAAATA
AAGAGGTCTCAGTTAAGCGCGTTACCACAATACGCAGGTCAGGGAATCTGACGCTCCGCTAGAGGCCAAGACT
GACGCTCCCGCAAGCGTTACCACAATACGCAGGTCAATCTCGTCATGAGGGCGACACAACTGCAAAAGAACTTAACGTGCG
GGTAAATTACACCAAGAGGTCAATCTCGTCATGAGGGCGACACAACTGCAAAAGAACTTAACGTGCG
AAGTCTGGGGTCCGACGTCCAGTCGCCAAAACTCATGCTCAGTTTAAAGCTCGAAAATAAAGAAGCTAAAGTGTC
CAAACGCGAAAAAGCCGTCTGGGTCCTCAATCCAGAAGCCGGCAATGCCTCCTCAGCGATTCC
GGGCAAGTGCTCCTCGAGTCGAATATTAAAGTACTCCCGACTTGGTCGACGCCCGTACAACCTATG (SEQ ID NO:22)

FIG. 22

```
CD4_SignalpepECD   ATGAACCGGGGAGTCCCTTTTAGGCACTTGCTTCTGGTGCTGCAACTGGCGCTCTCCCA
Mu_CD4_SignalECD   ATGAACCGAGGGGTGCCATTCAGACATTTGCTGCTTGTCCTCCAGCTTGCCCTGCTTCCT
                   ** ***** *  ** * ***  ** *   ** ** ***  ** * ** * **    * *

CD4_SignalpepECD   GCAGCCACTCAGGGAAAGAAAGTGGTTCTGGGCAAAAAAGGGGATACAGTGAACTGACC
Mu_CD4_SignalECD   GCCGCAACTCAAGGAAAAAAAGGTCGTCCTCGGGAAGAAGGGAGACACTGTTGAGCTAACA
                    * ** **** *****  **** *  ** ** ***  *** *** *  ** ** * * *

CD4_SignalpepECD   TGTACAGCTTCCCAGAAGAAGAGCATACAATTCCACTGGAAAAACTCCAACCAGATAAAG
Mu_CD4_SignalECD   TGCACTGCATCGCAAAAGAAGAGTATTCAGTTTCATTGGAAGAATTCAATCAAATCAAA
                   ** ** ** ** *** ******* **  * ** ** ****** **  *** *  * ***

CD4_SignalpepECD   ATTCTGGAAATCAGGGCTCCTCTTAACTAAAGGTCCATCCAAGCTGAATGATCGCGCT
Mu_CD4_SignalECD   ATACTCGGTAACCAAGGTCGTTTTTGACAAAGGGACCTTCGAAACTCAACGACCGGGCA
                   ** ** *   * **  * *  ** *  *****  * **  ***  * ** ** * **

CD4_SignalpepECD   GACTCAAGAAGAAGCCTTTGGGACCAAGGAAACTTTCCCCTGATCATCAAGAATTCTTAAG
Mu_CD4_SignalECD   GATTCTAGGAGAAGTCTATGGGATCAGGTAATTCTCCCGCTCATAATAAAAACCTAAAA
                   **  * ** *****  * ***** ** *  * * ****  * **  *  **  *  * *

CD4_SignalpepECD   ATAGAAGACTCAGATACTTACATCTGTGAAGTGGAGGACCAGAAGGAGGAGGTGCAATTG
Mu_CD4_SignalECD   ATTGAGGATTCTGACAGAAGTCTATGGAGTCGAGGTCGAAGATCAAAAGAAGAAGTCCAGTTA
                   ** ** **  *  ** *   * *   ***  *** *  **    **  *****  * **

CD4_SignalpepECD   CTAGTGTTCGGATTGACTGCCAACTCTGACACCACCTGCTTCAGGGGCAGAGCCTGACC
Mu_CD4_SignalECD   CTTGTCTTTGGTTTAACAGCGAATTCAGATACGCCATCTCCTACAAGGCCAAAGTCTCACG
                   ** ** ** **  *  * ** ** ** ** ** **   **  * ***** *  *  * *

CD4_SignalpepECD   CTGACCTTGGAGCCCCCCTGGTAGTAGCCCCTCAGTGCAATGTAGGAGTCCAAGGGGT
Mu_CD4_SignalECD   CTCACGTTAGAAAAGTCCGCCAGGAAGCAGTCCGTCCGTGCAGAAGCCCTAGAGGA
                   ** ** ** **    ** *  * * *** * ** *  *****  * *** **  * **
```

FIG. 22 (continued)

```
CD4_SignalpepECD   AAAAACATACAGGGGGGAAGACCCTCTCCGTGTCTCAGCTGGAGCTCCAGGATAGTGGC
Mu_CD4_SignalECD   AAGAATATTCAAGGCGGGCAGTGTCGGTCTCCACAACGCTGGTCTTCGAACTGCAAGACAGCGGG
                   ** ** *  *   * *  *  * **  ** *  ** ** ** ** ***  **  *   *  **

CD4_SignalpepECD   ACCTGGACATGCCACTGTCTTGCAGAACCAGAGAAGAAGGTGGAGTTCAAAATAGACATCGTG
Mu_CD4_SignalECD   ACGTGGACTTGTACAGTGTTACACAGTAATCAAAAATCAAAAAAAAGGTCGAATTTAAGATTGATATAGTC
                   ** ****  **  * * *  *    *    **  ****   *  ***  * *      **

CD4_SignalpepECD   GTGCTAGCTTTCCAGAAGGCCTCCAGCATAGTCTATAAGAAGAGGGGAACAGGTGGAG
Mu_CD4_SignalECD   GTCCTTGCATTTCAAAAAGCGTCGAGTATTGTGTACAAAAAGCAAGGCGAGCAAGTCGAA
                   **  *  * **** *** ** **  **  *  **  * ** *** *  * * **  **

CD4_SignalpepECD   TTCTCCTTCCCACTGCCTTTACAGTTGAAAAGCTGACGGGGCCAGTGGCGAGCTGTGGTGG
Mu_CD4_SignalECD   TTTTCGTTTCCTCTGGCGTTCACTGTAGAGAAACTTCACCGGGAGCCGAGCAAGTCTGGTGG
                   ** ** ** **  **  * * ***  ** ****  *  *** ** ****    *******

CD4_SignalpepECD   CAGGCGGAGAGGGCTTCCTCCTCCAAGTCTTGGATCACCTTTGACCTGAAGAACAAGGAA
Mu_CD4_SignalECD   CAAGCGGAAAGAGAGCATCGTCGTGGAAATCATGATTTACGTTCGATTCAAAAAATAAAGAG
                   ** ***** ** *   *  *** **** *  ** *  * ** *   **  ** ** ***

CD4_SignalpepECD   GTGTCTGTAAAACGGGTTACCCAGGACCCTAAGCTCCAGATGGGCAAGATGGGCAAGAAGCTCCCGCTC
Mu_CD4_SignalECD   GTCCTCAGTTAAGCGGTAAGCGGTTACCACAAGATCCAAAACTGCAAATGGGGGAAAAAACTGCCCCTG
                   **  **  * ** *** *  **  * **  *   *** ****   ** **** ** ** **

CD4_SignalpepECD   CACCTCACCCTGCCCCAGGCCTTGCCTCAGTATGCGGCTCTGGAAACCTCACCCTGGCC
Mu_CD4_SignalECD   CATCTGACGCTCCCCGCAAGCGTTACCAGCAAGCGTTACCAATACGCGACAGGTCAGGAATCTCAGGCGTCGCG
                   ** ** ** ** ***  ** *** ** ** **  * ** ** **** * ***  ** *  *

CD4_SignalpepECD   CTTGAAGCCGAAAACAGGAAGTTGCATCAGGAAGTGAACCTGGTGATGAGCCACT
Mu_CD4_SignalECD   CTAGAGGCCAAGACTGGTAAATTACACCAAGAGGTTCAATCTCGTCGTGATGAGGCGACA
                   ** ** *** **   ** ** ** ** ** **  *  * ** **  ** ****  ** *
```

FIG. 22 Continued

```
CD4_SignalpepECD   CAGCTCCAGAGAAAAATTTGACCTGTGAGGTGTGGGGACCCACCTCCCCTAAGCTGATGCTG
Mu_CD4_SignalECD   CAACTGCAAAAGAACTTAACGTGCCGAAGTCTGGGGTCCGACGTGCCAAACTCATGCTC
                   ** ** **  *****  *  *****  *  * *****  *   * ** * ** **** *

CD4_SignalpepECD   AGCTTGAAACTGGAGAACAAGGAGGCAAAGGTCTCGAAGGCGGGAGAAGGCGGTGTGGGTG
Mu_CD4_SignalECD   AGTTTAAAGCTCGAAAATAAAGAAGCTAAAGTGTCCAAACGCCGAAAAAAGCCGTCTGGGTC
                   ** ** ** ** ** **  ** ** ** ***** **  **  *** ** * ***** *

CD4_SignalpepECD   CTGAACCCTGAGGCGGGGATGTGGCAGTGTCTGCTGAGTGACTCGGGACAGGTCCTGCTG
Mu_CD4_SignalECD   CTCAATCCAGAGAAGCCGGCATGTGGCAATGTGGCAATGCCTCCTCAGCGATTCCGGGCAAGTGCTCCTC
                   ** ** ** ** *  * **  ******  ***  *  * **** ** **  ****  **

CD4_SignalpepECD   GAATCCAACATCAAGGTTCTGCCCACATGGTCCACCCCGGTGCAGCCAATG     (SEQ ID NO:21)  (1191)
Mu_CD4_SignalECD   GAGTCGAATATTAAAGTACTCCCGACTTGGTGACGCCCGTACAACCTATG     (SEQ ID NO:22)  (1191)
                   ** ** ** ** ** ** ** ** ** *** * ** *** * * * ****
```

FIG. 23

ATGAACCGGGAGTCCCTTTAGGCACTTGCTTCTGGTGCTGCAACTGGCGCTCCTCCCAGCAGCCACTC
AGGGAAGAAAGTGGTGCTGGGCAAAAAAGGGGATACAGTGAACTGACCTGTACAGCTTCCCAGAAGAA
GAGCATACAATTCCACTGGAAAAAACTCCAACCAGATAAAGATTCTGGGAAATCAGGGCTCCTTCTTAACT
AAAGGTCCATCCAAGCTGAATGATCGCGCTGACTCAAGAAGAAGCCTTTGGACCAAGGAAACTTCCCC
TGATCATCAAGAATCTTAAGATAGAAGACTCAGATACTTACATCTGTGAAGTGGAGGACCAGAAGGAGA
GGTGCAATTGCTAGTGTTCGGATTGACTGCCAACTCTGACACCCACCTGCTTCAGGGGCAGAGCCTGACC
CTGACCTTGGAGAGCCCCCCTGGTAGTAGCCCTCAGCTGGAGCTCCAGGATAGTGGCACCTGGACACATGA
AGGGGGAAGACCCTCCGTGTCTCAGCTTCAAAATAGACATCGTGGTGCTAGCTTCCAGAAGGCCTCCAGCATA
GCAGAACCAGAGAAGTGGAGTTCAAAAATAGACATCGTGGTGCTAGCTTCCAGAAGGCCTCCAGCATA
GTCTATAAGAAGAGGGGAACAGTGGAGTTCTCCTTCCCACTCGCCTTACAGTGAAAAGTGACGG
GCAGTGGCGAGCTGTGGGTGCAGGCGGGAGAGGCTTCTCCTCCAAGTCTTGGATCACCTTTGACCTGAA
GAACAAGGAAGTGTCTGTAAAACGGGTTACCCAGGCCCTAAGCTCCAAGAACCTCACCCTGGCCCTTGAA
CACCTCACCCTGCCCCAGCCTTGCTCAGTATGCTGCTCTGGTGATGAGAGCTGAGCTTGAAACTGGAGA
AAACAGGAAGTTGCATCAGGAAGTGAACCTGGTGGTGGATCAGCCCACTCAGCTCAGACTGGAGAACAAGGAGGCAAAG
CTGTGAGGTGTGGGGGACCCACCTCCCCCCTAAGCTGGTTGAACTGTGCCTTGAACTGGAGAACAAGGAGGCAAAG
GTCTCGAAGCGGGAGAAGCGGTGTGGGTGCTGAACCCTGAGGCGGGGATGTGGCAGTGTCTGCTGAGTG
ACTCGGGACAGTTCTGCTGGAATCAGGAAGCAGGATCACCTGGAATCCCTTCATCTATGGTGTCATTCTCACTGCCTTGTCCTGAGAGTGAAGTTCAG
GGATCCAAACTCGTCTACCGTCCGGGTGGTTCACTGCCTTGTCATTCTACGAGCTCAATCTAGGACGAAGAGGAGTACGATGT
CAGGAGCGCAGAGCGCCCCGCTGACCGTCCGGGTGGTTCACTGCCTTCTCATTCTACGAGCTCAATCTAGGACGAAGAGGAGTACGATGT
TTTGGACAAGAGTGCGCGGACCCTGAGATGGGGAAGCCAGGGAAAGCCGAGAAGAAGAACCCTCAGGAAGCCTGTACAATGAACTGCA
GAAAGATAAGATGGCGGAGGCTACAGTGAGATTGGGATGAGAATGAAAGGCGAGCGCCGAGGGCAAGGGCACGATGGCCTTTACCAGGG
TCTCAGTACAGCCACCAAGGACACCTACGACGCCCTTCACATGCAGCGCCCTGCCCCCTCGCTAA  (SEQ ID NO:23)

FIG. 24

ATGAACCGAGGGGTGCCATTCAGACATTTGCTGCTTGTCCTCCAGCTTGCCCTGCCTTCCTGCCGCAACTC
AAGGA
AAAAGGTCGTCCTCGGGAAGAATTCAAATCAAATCAAATACTGTTGAGCTAACATGCACTGCAAAGAAGAGTA
TTCAGTTTCATTGGAAGAATTCAAATCAAATCAAATACTCGGTAACCAAGGGTCGTTTTTGACAAGGG
ACCTTCGAAACTCAACGACCGGGCAGATTCTAGGAGAAGTCTATGGGATCAGGTAATTTCCGCTCATA
ATAAAAAACCTAAAAAATTGAGGATTGCAGACATATATTTGCGAGGTCGAAGATCAAAAGAAGAAGTCC
AGTTACTTGTCTTTGGTTTAACAGCGAATTCAGATACGCCATCTCCTACAAGGCCAAAGTCTCACGCTAC
GTTAGAAAGTCCCGCCAGGAAGCAGTCCGTCTGTCCAGTGCAGAAGCCCTAGAGAAGCAGCGGGACTGTACAGTTCAAGGC
GGCAAAACGCTGTCGTCTCACAACTCGAAACTGCAAGACAGCGGGACGTGTACAGTGTTACAAA
ATCAAAAAAGGTCGAATTTAAGATCGTCGTTTCCTCCTCGGCGTTCGTTCAACTGTAGAGAAACTCACCGGAGC
CAAAAGGAAGCGAGCAAGTCGAGCAAGTCGAATTTCGTTCCTCCTCGGCGTTCGAAATCATGAGAAACTGCCCCTGCATCT
GGGAACTCTGGTGGCAAGCGTTAAGCGCGTAACGCAAGATCCAAAACTGCAAATGGGGAAAAAACTGCCCCTGCATCT
AAGAGGTCTCAGTTAAGCGCGTTAACCGCAAGATCCAAAACTGCAAATGGGGAAAAAACTGCCCCTGCATCT
GACGCTCCCGCAAGCGTTACCACAGAGTCAATCTCGTCGTCATGAGGCGAATCTGACGCTCGCGCTAAAAGAACTTAACGTCG
GGTAAATTACACCAAGAGTCGACGTCGCCAAAACTCATGCTCAGTTTAAAGCTCGAAATAAGAAGCTAAAGTGTC
AAGTCTGGGGTCCGACGTCTCGCCAAAACTCATGCTCAGTTTAAAGCTCGAAATAAGAAGCTAAAGTGTC
CAAACGCAAGTGCTCCTCGAGTCGAATATTAAAGTACTCCCGACTTGGTCGACGCCCGTACAACCTATG
GGGCAAGTGCTCCTCGAGTCGAATATTAAAGTACTCCCGACTTGGTCGACGCCCGTACAACCTATG
CCTAGGAAATTGCTCCTCGAGTCTATGTATCCCTCCTCCTTACCTAGACAATGAAGAGAGCAATGAACCATTATCCATGTGAAAGGG
AAACACCTTTGTCCAAGTCCCTATTTCCCGGACCTTCTAAGCCCTTTTGGGTCGTGGTTGGTGAGTCCTGGCT
TGCTATAGCTTGCTAGTAACAGTGGCCTTTATTATTTCTGGGTGAGGAGTAAGAGGAGCAGGCTCCTGCACAGTGACTAC
ATGAACATGACTCCCCACCCGGCCCACCCCGAAGCATTACCAGCCCTATGCCCACCGGACTTCGCAGCCTAT
CGCTCCTAA (SEQ ID NO:24)

FIG. 25
1. Tctv-anti-JCV p36Z CIR
Vector 1 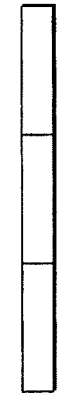
(Tctv_p36A_Z; Fig 12)
Vector 2 Va Cb Z
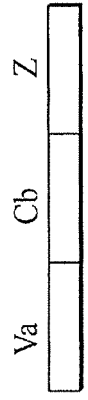
(Tctv_p36B_Z; Fig 14)
2. Tcsv-anti-JCV p36Z CIR
Vector Va Ca Z IRES Vb Cb muZ
(Tcsv_p36A_Z; Fig 12) (Tcsv_p36B_muZ; Fig 16)
**3. Tcsv-anti-JCV p3

FIG. 26

1. MuCD3Z_F1_primer (42 bp)
>MuCD3Z_F1_primer
TGCGGAGACTTGGATCCTAAGTTATGTTATTTATTAGACGGG (SEQ ID NO:25)

2. MuCD3Z_R1_primer (61 bp)
>MuCD3Z_R1_primer
AAATAGCGCTGTTAATATCACTCCGTATATAAATAAAATCCCGTCTAATAAATAACATAAC (SEQ ID NO:26)

3. MuCD3Z_F2_primer (49 bp)
>MuCD3Z_F2_primer
GTGATATTAACAGCGCTATTTTTACGTGTCAAATTTTCACGCTCCGCTG (SEQ ID NO:27)

4. MuCD3Z_R2_primer (93 bp)
>MuCD3Z_R2_primer
TTCTTCTCTACGACCCAAGTTCAATTCATTGTACAATTGATTTTGCCCTTGTTGATAGGCCGGCGCATCA
GCGGAGCGTGAAAATTTGACACG (SEQ ID NO:28)

5. MuCD3Z_F3_primer (92 bp)
>MuCD3Z_F3_primer
CTTGGGTCGTAGAGAAGAATATGACGTACTCGATAAACGGAGGGGGCGCGATCCAGAAATGGGCGGCAAA
CCACGGCGAAAAAATCCACAAG (SEQ ID NO:29)

6. MuCD3Z_R3_primer (94 bp)
>MuCD3Z_R3_primer
CCCCTTCATACCTATTTCTGAATATGCTTCTGCCATTTTGTCCTTTTGTAACTCGTTATATAATCCCTCT
TGTGGATTTTTTCGCCGTGGTTTG (SEQ ID NO:30)

7. MuCD3Z_F4_primer (97 bp)
>MuCD3Z_F4_primer
TTCAGAAATAGGTATGAAGGGGGAAAGGAGACGAGGGAAAGGTCATGACGGATTGTATCAAGGATTATCG
ACCGCGACTAAAGATACGTATGATGCG (SEQ ID NO:31)

8. MuCD3Z_R4_StopBsepI_primer (64 bp)
>MuCD3Z_R4_StopBsepI_primer
ACGATCCGGACTTATCTTGGCGGTAATGCTTGCATGTGTAACGCATCATACGTATCTTTAGTCG
(SEQ ID NO:32)

Potential problem:
- due to low rates of co-transductions

FIG. 33

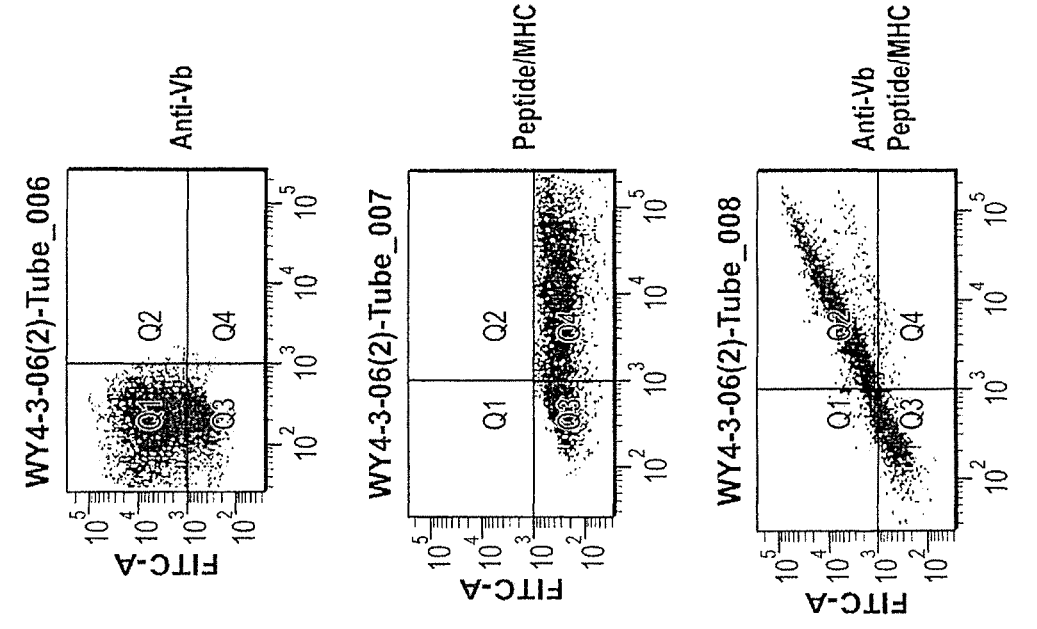
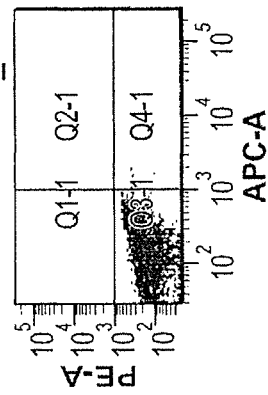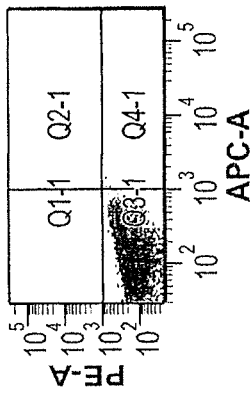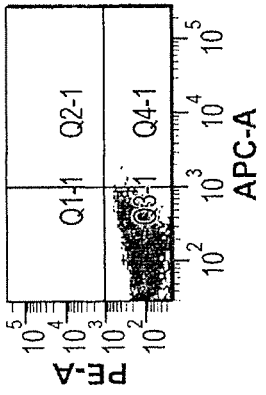
FIG. 34

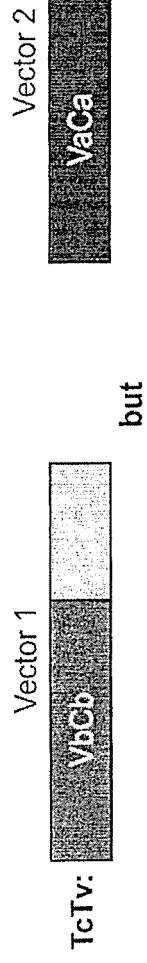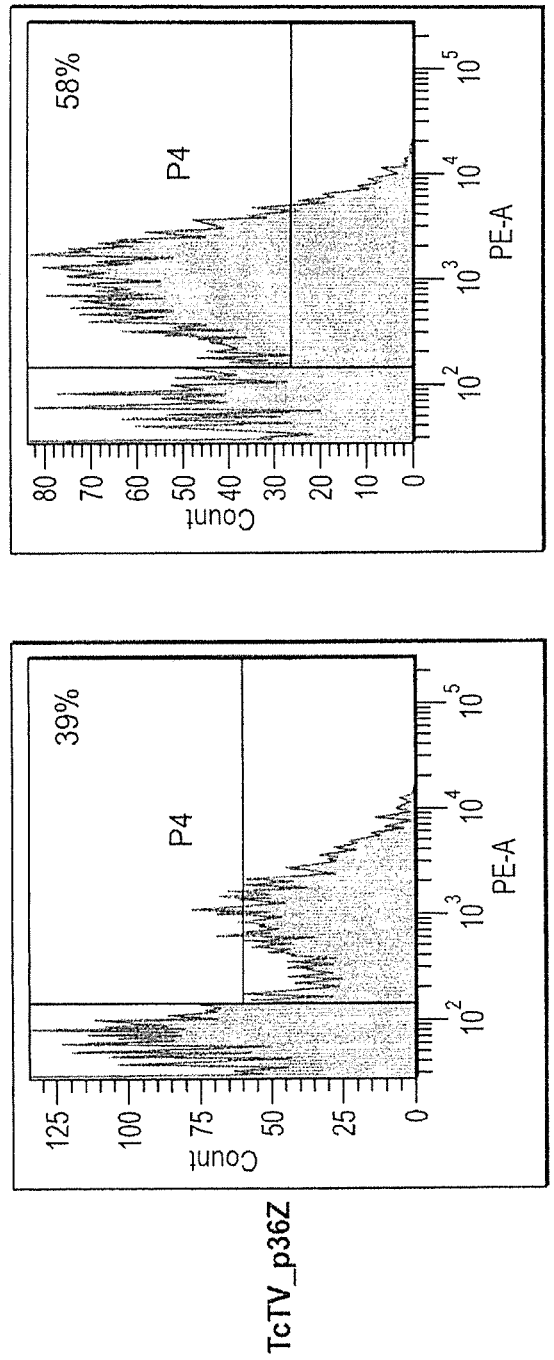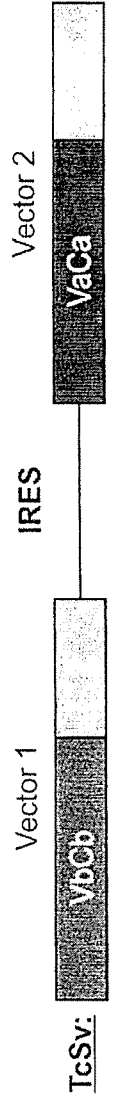
FIG. 36

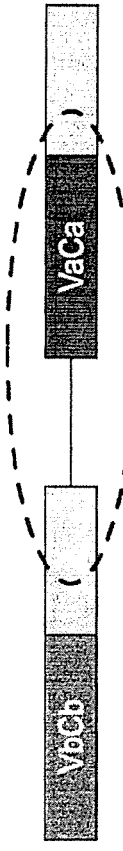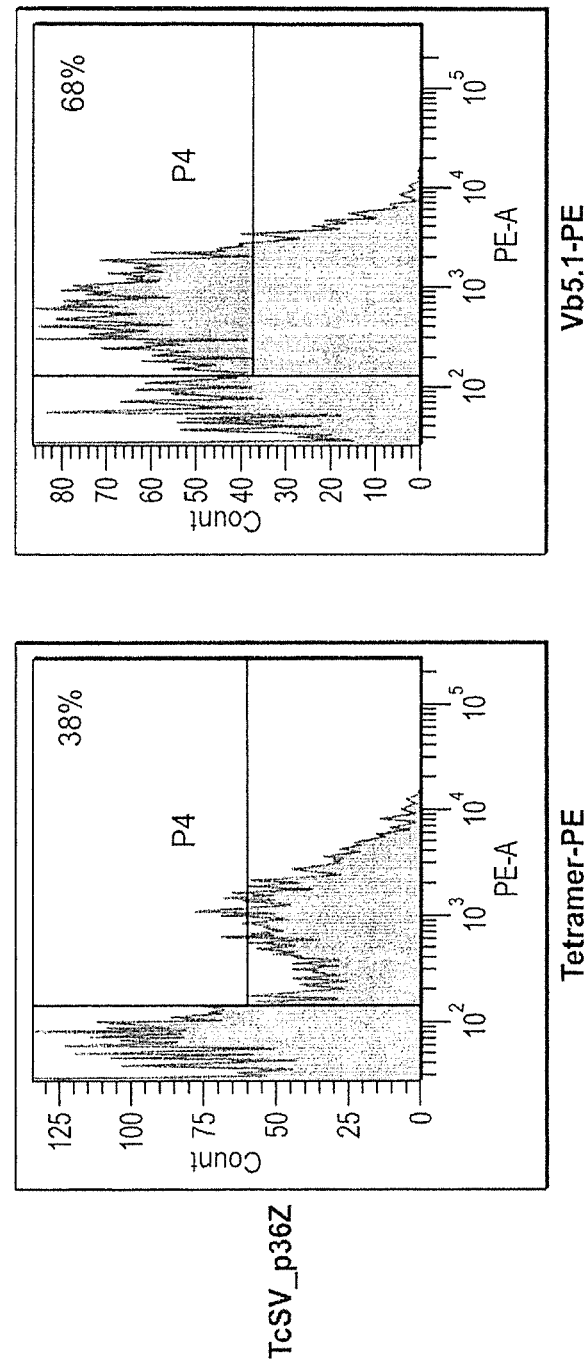
FIG. 37

FIG. 38

```
NT_Mutated_CD28CD3zeta    CCTAGGAAGATCGAGGTAATGTACCCACCGCCCTATCTCGATAACGAAAA        50
CD28CD3Z                  CCTAGGAAGATCGAGGTAATGTACCCACCGCCCTATCTCGATAACGAAAA
                          **************************************************

NT_Mutated_CD28CD3zeta    AAGTAAACGGTACAATAATTCACGTTAAGGGAAAGCATTTATGCCCTTCCC       100
CD28CD3Z                  GAGCAATGAAACCATTATCCATGTGAAAGGGAAACACCTTTGTCCAAGTC
                          *  *  **  **  **  * *  * ***** **  * *** ** ***  *

NT_Mutated_CD28CD3zeta    CGTTGTTCCCGGGCCCAAGCAAACCGTTCTGGGTTCTCGTAGTTGTAGGC       150
CD28CD3Z                  CCCTATTTCCCGGACCTTCTAAGCCCTTTTGGGTGCTGGTGGTGGTTGGT
                          * * ***  ****  **  ** ***   *** ****  ** **** ** *

NT_Mutated_CD28CD3zeta    GGTGTGTTAGCATGTTACTCTCTCCTTGTTACAGTAGCTTTCATAATCTT       200
CD28CD3Z                  GGAGTCCTGGCTTGCTCTATAGCTTGCTAGTAACAGTGGCCTTTATTTTT
                          ** **    ***   *** ** ** ****  ** ***   ** ** ** *

NT_Mutated_CD28CD3zeta    TTGGGTCCGATCAAAACGCTCTCGATTGTTACATTCCGATTATATGAATA       250
CD28CD3Z                  CTGGGTGAGGAGTAAGAGGAGCAGGCTCCTGCACAGTGACTACATGAACA
                          ****    * *  *   *  *  * ***  ** *** ** ** **** *

NT_Mutated_CD28CD3zeta    TGACACCGAGGAGACCTGGCCCGACGAGGAAACACTATCAACCGTACGCA       300
CD28CD3Z                  TGACTCCCCCGCCCGCCCGGGCCCACCCGCCAAGCATTACCAGCCTATGCC
                          **** **     *  ***  *  * **    *  ** **  ** *  **

NT_Mutated_CD28CD3zeta    CCTCCGAGAGATTTGCTGCTACAGGAGTCGTGTCAAATTTTCACGCTC         350
CD28CD3Z                  CCACCACGCCACTTCGCAGCCTATCGCTCCAGAGTCGCTCCAGAGTTCAGCGAGGAG
                          ** ** **  **  ** ** **  * ** ** ***  **  ***   *
```

FIG. 38 (continued)

```
NT_Mutated_CD28CD3zeta   CGCTGATGCGCCGGCCTATCAACAAGGGCAAAATCAATTGTACAATGAAT    400
CD28CD3Z                 CGCAGAGCGCCCCCGCGTACCTACCAGGGCCAGAACCAGCTCTATAACGAGC
                         ***  ** ** **  * ** ** *   * ***   *   **  ** **

NT_Mutated_CD28CD3zeta   TGAACTTGGGTCGTAGAGAAGAATATGACGTACTCGATAAACGGAGAGGGGG    450
CD28CD3Z                 TCAATCTAGGACGAAGAGAGAGGAGTACGATGTTTTGGACAAGAGACGTGGC
                         * **  **    ** ***** **    *   **  ** * * *   ** **

NT_Mutated_CD28CD3zeta   CGCGATCCAGAAATGGGCGGCAAACCACGGCGAAAAATCCACAAGAGGG    500
CD28CD3Z                 CGGGACCCTGAGATGGGGGGAAGCCGGAAGAAGAACCCTCAGGAAGG
                         ** **  ** ** ** ****** **  **  * **  ** ** ** ****

NT_Mutated_CD28CD3zeta   ATTATATAACGAGTTACAAAAGGACAAAATGGCAGAAGCATATATTCAGAAA    550
CD28CD3Z                 CCTGTACAATGAACTGCAGAAAGATAAGATGGCGGAGGCCTACAGTGAGA
                         * ** **  * ** **  *   *    *   ****** *** ** * ** *

NT_Mutated_CD28CD3zeta   TAGGTATGAAGGGGGAAAGGAGAGCGAGGGAAAGGTCATGACGGATTGTAT    600
CD28CD3Z                 TTGGGATGAAAGGCCGAGCGCCCGGAGGGGCACGATGGCCTTTAC
                         * ** ******   **   *    *** **  **   ** ** **   * *

NT_Mutated_CD28CD3zeta   CAAGGATTATCGACCGCGACTAAAGATACGTATGATGCGTTACACATGCA    650
CD28CD3Z                 CAGGGTCTCAGTACACAGCCACCAAGGACACCTACGACGCCCTTCACATGCA
                         ** *    **  **   **   * **  **  ** **  *  ********

NT_Mutated_CD28CD3zeta   AGCATTACCGCCAAGATAA                                    669
CD28CD3Z                 GGCCCCTGCCCCCTCGCTAA
                         ** **  **   *  * ***
```

FIG. 38 (continued)

Aligment of nucleotide sequences of chimeric CD28CD3Zeta with mutated chimeric CD28CD3Zeta. The corresponding n.t. sequences encoding partial CD28 and CD3Zeta are from native human CD28

Same problem in anti-JCV TcSv

Solution engineer degenerate nucleotides in repeated sequence to prevent homologus recombination and deletion TcSv:

Solution:
TcSv:

Mutations at n.t. seq.

Homology reduced 100% 60%

FIG. 40

- improve design two-chain single vector (tcsv)
- expression from same vector for same cell transduction
- 1st gen: 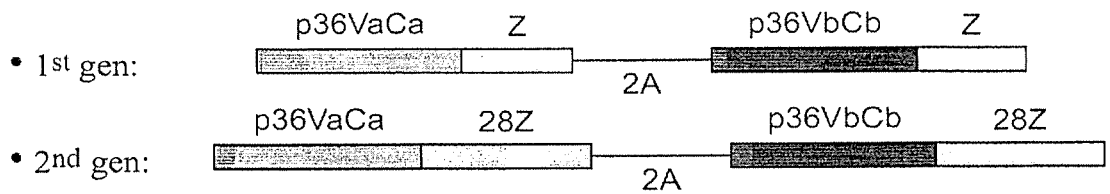
- 2nd gen:
- linked using IRES or 2A
- constructs expressed in MFG retroviral expression vector

FIG. 41

- Potential for homologous sequence recombination and deletion between repeat z or 28z

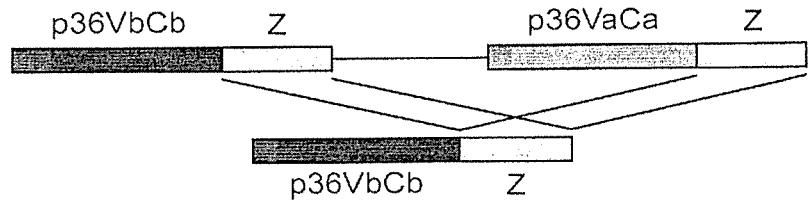

- e.g. deletion of internal VaCa chain between repeat zeta reduces heterodimer expression

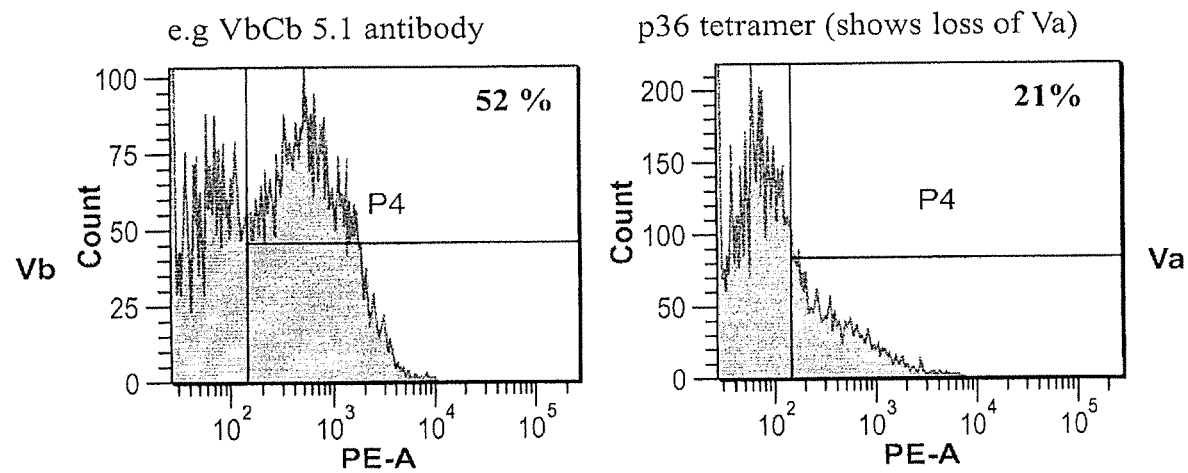

FIG. 42

- suppress recombination and deletion
- engineer codon degenerate nucleotides in repeated zeta chains to reduced homology
- tm/cyt CD3 zeta chain nucleotide homology reduced to 60%

```
       L  D  P  K  L  C  Y  L  L  D  G  I  L  F  I  Y  G  V  I  L  T  A  L  F  L  R  V  K  F  S  R  S  A  D  A
wtCD3z CTGGATCCCAAACTCTGCTACCTGCTGGATGGAATCCTCTTCATCTATGGTGTCATTCTCACTGCCTTGTTCCTGAGAGTGAAGTTCAGCAGGAGCGCAGACGCC
dCD3z  CTGGATCCCAAATTGTGTTATTTGTTGGACGGGATTTTATTTATATACGGAGTGATATTAACAGCGCTATTTTTACGTGTCAAATTTTCACGCTCCGCTGATGCG

P  A  Y  Q  Q  G  Q  N  Q  L  Y  N  E  L  N  L  G  R  R  E  E  Y  D  V  L  D  K  R  R  G  R  D  P  E  M
wtCD3z CCCGCGTACCAGCAGGGCCAGAACCAGCTCTATAACGAGCTCAATCTAGGACGAAGAGAGGAGTACGATGTTTTGGACAAGAGACGTGGCCGGGACCCTGAGATG
dCD3z  CCGGCCTATCAACAAGGGCAAAATCAATTGTACAATGAATTGAACTTGGGTCGTAGAGAAGAATATGACGTACTCGATAAACGGAGGGGGCGCGATCCAGAAATG

G  G  K  P  R  R  K  N  P  Q  E  G  L  Y  N  E  L  Q  K  D  K  M  A  E  A  Y  S  E  I  G  M  K  G  E  R
wtCD3z GGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGC
dCD3z  GGCGGCAAACCACGGCGAAAAAATCCACAAGAGGGATTATATAACGAGTTACAAAAGGACAAAATGGCAGAAGCATATTCAGAAATAGGTATGAAGGGGGAAAGG

R  R  G  K  G  H  D  G  L  Y  Q  G  L  S  T  A  T  K  D  T  Y  D  A  L  H  M  Q  A  L  P  P  R  *
wtCD3z CGGAGGGGCAAGGGGCACGATGGCCTTTACCAGGGTCTCAGTACAGCCACCAAGGACACCTACGACGCCCTTCACATGCAGGCCCTGCCCCCTCGCTAA
dCD3z  AGACGAGGGAAAGGTCATGACGGATTGTATCAAGGATTATCGACCGCGACTAAAGATACGTATGATGCGTTACACATGCAAGCATTACCGCCAAGATAA
```

SEQUENCE LISTING

```
<160> NUMBER OF SEQ ID NOS: 37

<210> SEQ ID NO 1
<211> LENGTH: 414
<212> TYPE: DNA
<213> ORGANISM: Unknown
<220> FEATURE:
<223> OTHER INFORMATION: Mutated nucleotide sequence of partial human
      CD3Zeta

<400> SEQUENCE: 1
ttggatccta agttatgtta tttattagac gggattttat ttatatacgg agtgatatta      60
acagcgctat ttttacgtgt caaattttca cgctccgctg atgcgccggc ctatcaacaa     120
gggcaaaatc aattgtacaa tgaattgaac ttgggtcgta gagaagaata tgacgtactc     180
gataaacgga gggggcgcga tccagaaatg ggcggcaaac cacggcgaaa aaatccacaa     240
gagggattat ataacgagtt acaaaaggac aaaatggcag aagcatattc agaaataggt     300
atgaaggggg aaaggagacg agggaaaggt catgacggat tgtatcaagg attatcgacc     360
gcgactaaag atacgtatga tgcgttacac atgcaagcat taccgccaag ataa           414

<210> SEQ ID NO 2
<211> LENGTH: 137
<212> TYPE: PRT
<213> ORGANISM: Unknown
<220> FEATURE:
<223> OTHER INFORMATION: Mutated amino acid sequence of partial human
      CD3Zeta

<400> SEQUENCE: 2

Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys Phe Ser Arg Ser
            20                  25                  30

Ala Asp Ala Pro Ala Tyr Gln Gln Gly Gln Asn Gln Leu Tyr Asn Glu
        35                  40                  45
```

```
Leu Asn Leu Gly Arg Arg Glu Glu Tyr Asp Val Leu Asp Lys Arg Arg
        50                  55                  60

Gly Arg Asp Pro Glu Met Gly Gly Lys Pro Arg Arg Lys Asn Pro Gln
 65                  70                  75                  80

Glu Gly Leu Tyr Asn Glu Leu Gln Lys Asp Lys Met Ala Glu Ala Tyr
                 85                  90                  95

Ser Glu Ile Gly Met Lys Gly Glu Arg Arg Arg Gly Lys Gly His Asp
            100                 105                 110

Gly Leu Tyr Gln Gly Leu Ser Thr Ala Thr Lys Asp Thr Tyr Asp Ala
        115                 120                 125

Leu His Met Gln Ala Leu Pro Pro Arg
    130                 135

<210> SEQ ID NO 3
<211> LENGTH: 414
<212> TYPE: DNA
<213> ORGANISM: Unknown
<220> FEATURE:
<223> OTHER INFORMATION: Partial human CD3Zeta of GenBank ID X55510.1

<400> SEQUENCE: 3
ctggatccca aactctgcta cctgctggat ggaatcctct tcatctatgg tgtcattctc     60
actgccttgt tcctgagagt gaagttcagc aggagcgcag acgccccccgc gtaccagcag    120 ggccagaacc agctctataa cgagctcaat ctaggacgaa gagaggagta cgatgttttg    180
gacaagagac gtggccggga ccctgagatg ggggggaaagc cgagaaggaa gaaccctcag    240
gaaggcctgt acaatgaact gcagaaagat aagatggcgg aggcctacag tgagattggg    300
atgaaaggcg agcgccggag gggcaagggg cacgatggcc tttaccaggg tctcagtaca    360
gccaccaagg acacctacga cgcccttcac atgcaggccc tgccccctcg ctaa          414

<210> SEQ ID NO 4
<211> LENGTH: 669
<212> TYPE: DNA
<213> ORGANISM: Unknown
<220> FEATURE:
<223> OTHER INFORMATION: Fusion polypeptide construct comprising partial
      human CD28 and CD3Zeta sequences that are altered
      (mutated chimeric CD28CD3Zeta)

<400> SEQUENCE: 4
cctaggaaga tcgaggtaat gtacccaccg ccctatctcg ataacgaaaa agtaacggt     60 acaataattc acgttaaggg aaagcattta tgcccttccc cgttgttccc gggcccaagc    120
aaaccgttct gggttctcgt agttgtaggc ggtgtgttag catgttactc tctccttgtt    180
acagtagctt tcataatctt tgggtccga tcaaaacgct ctcgattgtt acattccgat     240
tatatgaata tgacaccgag gagacctggc ccgacgagga acactatca accgtacgca    300 cctccgagag attttgctgc gtacaggagt cgtgtcaaat tttcacgctc cgctgatgcg    360
ccggcctatc aacaagggca aaatcaattg tacaatgaat tgaacttggg tcgtagagaa    420
gaatatgacg tactcgataa acggaggggg cgcgatccag aaatgggcgg caaaccacgg    480
cgaaaaaatc cacaagaggg attatataac gagttacaaa aggacaaaat ggcagaagca    540
tattcagaaa taggtatgaa gggggaaagg agacgaggga aggtcatga cggattgtat    600 caaggattat cgaccgcgac taagatacg tatgatgcgt tacacatgca agcattaccg    660
ccaagataa                                                            669
```

<210> SEQ ID NO 5
<211> LENGTH: 222
<212> TYPE: PRT
<213> ORGANISM: Unknown
<220> FEATURE:
<223> OTHER INFORMATION: Fusion polypeptide construct comprising partial human CD28 and CD3Zeta sequences that are altered (mutated chimeric CD28CD3Zeta)

<400> SEQUENCE: 5

Pro Arg Lys Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
            20                  25                  30

Ser Pro Leu Phe Pro Gly Pro Ser Lys Pro Phe Trp Val Leu Val Val
        35                  40                  45

Val Gly Gly Val Leu Ala Cys Tyr Ser Leu Leu Val Thr Val Ala Phe
    50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
            100                 105                 110

Lys Phe Ser Arg Ser Ala Asp Ala Pro Ala Tyr Gln Gln Gly Gln Asn
        115                 120                 125

Gln Leu Tyr Asn Glu Leu Asn Leu Gly Arg Arg Glu Glu Tyr Asp Val
    130                 135                 140

Leu Asp Lys Arg Arg Gly Arg Asp Pro Glu Met Gly Gly Lys Pro Arg
145                 150                 155                 160

Arg Lys Asn Pro Gln Glu Gly Leu Tyr Asn Glu Leu Gln Lys Asp Lys
                165                 170                 175

Met Ala Glu Ala Tyr Ser Glu Ile Gly Met Lys Gly Glu Arg Arg Arg
            180                 185                 190

Gly Lys Gly His Asp Gly Leu Tyr Gln Gly Leu Ser Thr Ala Thr Lys
        195                 200                 205

Asp Thr Tyr Asp Ala Leu His Met Gln Ala Leu Pro Pro Arg
    210                 215                 220

<210> SEQ ID NO 6
<211> LENGTH: 669
<212> TYPE: DNA
<213> ORGANISM: Unknown
<220> FEATURE:
<223> OTHER INFORMATION: Chimeric CD28CD3Zeta

<400> SEQUENCE: 6
cctaggaaaa ttgaagttat gtatcctcct ccttacctag acaatgagaa gagcaatgga      60
accattatcc atgtgaaagg gaaacacctt tgtccaagtc ccctatttcc cggaccttct     120
aagccctttt gggtgctggt ggtggttggt ggagtcctgg cttgctatag cttgctagta     180
acagtggcct ttattatttt ctgggtgagg agtaagagga gcaggctcct gcacagtgac     240
tacatgaaca tgactccccg ccgccccggg cccacccgca agcattacca gccctatgcc     300
ccaccacgcg acttcgcagc ctatcgctcc agagtgaagt tcagcaggag cgcagacgcc     360
cccgcgtacc agcagggcca gaaccagctc tataacgagc tcaatctagg acgaagagag     420
gagtacgatg tttggacaa gagacgtggc cgggaccctg agatgggggg aaagccgaga     480

```
aggaagaacc ctcaggaagg cctgtacaat gaactgcaga aagataagat ggcggaggcc    540
tacagtgaga ttgggatgaa aggcgagcgc cggaggggca aggggcacga tggcctttac    600
cagggtctca gtacagccac caaggacacc tacgacgccc ttcacatgca ggccctgccc    660
cctcgctaa                                                            669

<210> SEQ ID NO 7
<211> LENGTH: 198
<212> TYPE: DNA
<213> ORGANISM: Unknown
<220> FEATURE:
<223> OTHER INFORMATION: Gene that encodes a partial extracellular
      domain and the entire transmembrane and cytoplasmic
      domains of human FCEpsilonRIGamma

<400> SEQUENCE: 7
cctcaattat gttacatatt agacgcgatt ttattcttat acgggatcgt tttaacatta     60
ttatattgcc gtttaaaaat tcaggttcgg aaagccgcga tcacttcata cgaaaagagc    120
gacggcgtgt atacaggttt atcaacacga atcaagaaa cgtatgaaac cttaaaacac    180
gaaaagcccc ctcaatag                                                  198

<210> SEQ ID NO 8
<211> LENGTH: 65
<212> TYPE: PRT
<213> ORGANISM: Unknown
<220> FEATURE:
<223> OTHER INFORMATION: Gene that encodes a partial extracellular
      domain and the entire transmembrane and cytoplasmic
      domains of human FCEpsilonRIGamma

<400> SEQUENCE: 8

Pro Gln Leu Cys Tyr Ile Leu Asp Ala Ile Leu Phe Leu Tyr Gly Ile
1               5                   10                  15

Val Leu Thr Leu Leu Tyr Cys Arg Leu Lys Ile Gln Val Arg Lys Ala
            20                  25                  30

Ala Ile Thr Ser Tyr Glu Lys Ser Asp Gly Val Tyr Thr Gly Leu Ser
        35                  40                  45

Thr Arg Asn Gln Glu Thr Tyr Glu Thr Leu Lys His Glu Lys Pro Pro
    50                  55                  60

Gln
65

<210> SEQ ID NO 9
<211> LENGTH: 300
<212> TYPE: DNA
<213> ORGANISM: Unknown
<220> FEATURE:
<223> OTHER INFORMATION: Partial human FCEpsilonRIGamma (GenBank ID
      M33195.1)

<400> SEQUENCE: 9
cagaacggcc gatctccagc ccaagatgat tccagcagtg gtcttgctct tactccttt     60 ggttgaacaa gcagcggccc tgggagagcc tcagctctgc tatatcctgg atgccatcct    120
gtttctgtat ggaattgtcc tcaccctcct ctactgtcga ctgaagatcc aagtgcgaaa    180
ggcagctata accagctatg agaaatcaga tggtgtttac acgggcctga gcaccaggaa    240
ccaggagact tacgagactc tgaagcatga gaaccaccag tagccttt agaatagatg    300

<210> SEQ ID NO 10
```

-continued

<211> LENGTH: 420
<212> TYPE: DNA
<213> ORGANISM: Unknown
<220> FEATURE:
<223> OTHER INFORMATION: Anti-p36 TCRAlpha sequence

<400> SEQUENCE: 10

```
gggatctgg atcccaaact ctgctacctg ctggatggaa tcctcttcat ctatggtgtc     60
attctcactg ccttgttcct gagagtgaag ttcagcagga gcgcagacgc ccccgcgtac   120
cagcagggcc agaaccagct ctataacgag ctcaatctag gacgaagaga ggagtacgat   180
gttttggaca gagacgtgg ccgggaccct gagatggggg gaaagccgag aaggaagaac   240
cctcaggaag gcctgtacaa tgaactgcag aaagataaga tggcggaggc ctacagtgag   300
attgggatga aggcgagcg ccggaggggc aaggggcacg atggccttta ccagggtctc   360
agtacagcca ccaaggacac ctacgacgcc cttcacatgc aggccctgcc ccctcgctaa   420
```

<210> SEQ ID NO 11

<400> SEQUENCE: 11

000

<210> SEQ ID NO 12
<211> LENGTH: 139
<212> TYPE: PRT
<213> ORGANISM: Unknown
<220> FEATURE:
<223> OTHER INFORMATION: Anti-p36 TCRAlpha sequence

<400> SEQUENCE: 12

Gly Asp Leu Asp Pro Lys Leu Cys Tyr Leu Leu Asp Gly Ile Leu Phe
1               5                   10                  15

Ile Tyr Gly Val Ile Leu Thr Ala Leu Phe Leu Arg Val Lys Phe Ser
            20                  25                  30

Arg Ser Ala Asp Ala Pro Ala Tyr Gln Gln Gly Gln Asn Gln Leu Tyr
        35                  40                  45

Asn Glu Leu Asn Leu Gly Arg Arg Glu Glu Tyr Asp Val Leu Asp Lys
    50                  55                  60

Arg Arg Gly Arg Asp Pro Glu Met Gly Gly Lys Pro Arg Arg Lys Asn
65                  70                  75                  80

Pro Gln Glu Gly Leu Tyr Asn Glu Leu Gln Lys Asp Lys Met Ala Glu
                85                  90                  95

Ala Tyr Ser Glu Ile Gly Met Lys Gly Glu Arg Arg Arg Gly Lys Gly
            100                 105                 110

His Asp Gly Leu Tyr Gln Gly Leu Ser Thr Ala Thr Lys Asp Thr Tyr
        115                 120                 125

Asp Ala Leu His Met Gln Ala Leu Pro Pro Arg
    130                 135

<210> SEQ ID NO 13
<211> LENGTH: 420
<212> TYPE: DNA
<213> ORGANISM: Unknown
<220> FEATURE:
<223> OTHER INFORMATION: Anti-p36 TCRBeta sequence

<400> SEQUENCE: 13

```
gggatctgg atcccaaact ctgctacctg ctggatggaa tcctcttcat ctatggtgtc     60
attctcactg ccttgttcct gagagtgaag ttcagcagga gcgcagacgc ccccgcgtac   120
```

```
cagcagggcc agaaccagct ctataacgag ctcaatctag gacgaagaga ggagtacgat    180
gttttggaca agagacgtgg ccgggaccct gagatggggg aaagccgag aaggaagaac    240 cctcaggaag gcctgtacaa tgaactgcag aaagataaga tggcggaggc ctacagtgag    300
attgggatga aggcgagcg ccggaggggc aaggggcacg atggccttta ccagggtctc    360
agtacagcca ccaaggacac ctacgacgcc ttcacatgc aggccctgcc cctcgctaa    420
```

```
<210> SEQ ID NO 14
<211> LENGTH: 419
<212> TYPE: DNA
<213> ORGANISM: Unknown
<220> FEATURE:
<223> OTHER INFORMATION: Anti-p36 TCRBeta sequence

<400> SEQUENCE: 14 gggggatctgg atcccaaact ctgctacctg ctggatggaa tcctcttcat ctatggtgtc     60
attctcactg ccttgttcct gagagtgaag ttcagcagga gcgcagacgc ccccgcgtac    120
cagcagggcc agaaccagct ctataacgag ctcaatctag gacgaagaga ggagtacgat    180
gttttggaca agagacgtgg ccgggaccct gagatggggg aaagccgag aaggaagaac    240 cctcaggaag gcctgtacaa tgaactgcag aaagataaga tggcggaggc ctacagtgag    300
attgggatga aggcgagcg ccggaggggc aaggggcacg atggccttta ccagggtctc    360
agtacagcca ccaaggacac ctacgacccc ttcacatgca ggccctgccc cctcgctaa    419
```

```
<210> SEQ ID NO 15
<211> LENGTH: 139
<212> TYPE: PRT
<213> ORGANISM: Unknown
<220> FEATURE:
<223> OTHER INFORMATION: Anti-p36 TCRBeta sequence

<400> SEQUENCE: 15

Gly Asp Leu Asp Pro Lys Leu Cys Tyr Leu Leu Asp Gly Ile Leu Phe
1               5                   10                  15

Ile Tyr Gly Val Ile Leu Thr Ala Leu Phe Leu Arg Val Lys Phe Ser
            20                  25                  30

Arg Ser Ala Glu Pro Pro Ala Tyr Gln Gln Gly Gln Asn Gln Leu Tyr
        35                  40                  45

Asn Glu Leu Asn Leu Gly Arg Arg Glu Glu Tyr Asp Val Leu Asp Lys
    50                  55                  60

Arg Arg Gly Arg Asp Pro Glu Met Gly Gly Lys Pro Arg Arg Lys Asn
65                  70                  75                  80

Pro Gln Glu Gly Leu Tyr Asn Glu Leu Gln Lys Asp Lys Met Ala Glu
                85                  90                  95

Ala Tyr Ser Glu Ile Gly Met Lys Gly Glu Arg Arg Arg Gly Lys Gly
            100                 105                 110

His Asp Gly Leu Tyr Gln Gly Leu Ser Thr Ala Thr Lys Asp Thr Tyr
        115                 120                 125

Asp Ala Leu His Met Gln Ala Leu Pro Pro Arg
    130                 135
```

```
<210> SEQ ID NO 16
<211> LENGTH: 421
<212> TYPE: DNA
<213> ORGANISM: Unknown
<220> FEATURE:
<223> OTHER INFORMATION: Mutated anti-p36 TCRBeta sequence
```

(Tcsv_p36b_muZ)

<400> SEQUENCE: 16

```
ggggatctgg atcctaagtt atgttattta ttagacggga ttttatttat atacggagtg    60
atattaacag cgctattttt acgtgtcaaa ttttcacgct ccgctgatgc gccggcctat   120
caacaagggc aaaatcaatt gtacaatgaa ttgaactttg ggtcgtagag aagaatatga   180
cgtactcgat aaacggaggg ggcgcgatcc agaaatgggc ggcaaaccac ggcgaaaaaa   240
tccacaagag ggattatata acgagttaca aaggacaaa atggcagaag catattcaga    300
aataggtatg aaggggggaaa ggagacgagg gaaaggtcat gacggattgt atcaaggatt   360
atcgaccgcg actaaagata cgtatgatgc gttacacatg caagcattac cgccaagata   420
a                                                                   421
```

<210> SEQ ID NO 17
<211> LENGTH: 669
<212> TYPE: DNA
<213> ORGANISM: Unknown
<220> FEATURE:
<223> OTHER INFORMATION: Anti-p36 TCRAlpha sequence (Tcsv_p36A_28Z)

<400> SEQUENCE: 17

```
cctaggaaaa ttgaagttat gtatcctcct ccttacctag acaatgagaa gagcaatgga    60
accattatcc atgtgaaagg gaaacacctt tgtccaagtc ccctatttcc cggaccttct   120
aagccctttt gggtgctggt ggtggttggt ggagtcctgg cttgctatag cttgctagta   180
acagtggcct ttattatttt ctgggtgagg agtaagagga gcaggctcct gcacagtgac   240
tacatgaaca tgactccccg ccgccccggg cccacccgca agcattacca gccctatgcc   300
ccaccacgcg acttcgcagc ctatcgctcc agagtgaagt tcagcaggag cgcagacgcc   360
cccgcgtacc agcagggcca gaaccagctc tataacgagc tcaatctagg acgaagagag   420
gagtacgatg ttttggacaa gagacgtggc cgggaccctg agatgggggg aaagccgaga   480
aggaagaacc ctcaggaagg cctgtacaat gaactgcaga agataagat ggcggaggcc    540
tacagtgaga ttgggatgaa aggcgagcgc cggaggggca aggggcacga tggcctttac   600
cagggtctca gtacagccac caaggacacc tacgacgccc ttcacatgca ggccctgccc   660
cctcgctaa                                                          669
```

<210> SEQ ID NO 18
<211> LENGTH: 222
<212> TYPE: PRT
<213> ORGANISM: Unknown
<220> FEATURE:
<223> OTHER INFORMATION: Anti-p36 TCRAlpha sequence (Tctsv_p36A_28Z)

<400> SEQUENCE: 18

```
Pro Arg Lys Ile Glu Val Met Tyr Pro Pro Pro Tyr Leu Asp Asn Glu
 1               5                  10                  15

Lys Ser Asn Gly Thr Ile Ile His Val Lys Gly Lys His Leu Cys Pro
            20                  25                  30

Ser Pro Leu Phe Pro Gly Pro Ser Lys Pro Phe Trp Val Leu Val Val
        35                  40                  45

Val Gly Gly Val Leu Ala Cys Tyr Ser Leu Leu Val Thr Val Ala Phe
    50                  55                  60

Ile Ile Phe Trp Val Arg Ser Lys Arg Ser Arg Leu Leu His Ser Asp
65                  70                  75                  80
```

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
            100                 105                 110

Lys Phe Ser Arg Ser Ala Asp Ala Pro Ala Tyr Gln Gln Gly Gln Asn
            115                 120                 125

Gln Leu Tyr Asn Glu Leu Asn Leu Gly Arg Arg Glu Glu Tyr Asp Val
            130                 135                 140

Leu Asp Lys Arg Arg Gly Arg Asp Pro Glu Met Gly Gly Lys Pro Arg
145                 150                 155                 160

Arg Lys Asn Pro Gln Glu Gly Leu Tyr Asn Glu Leu Gln Lys Asp Lys
                165                 170                 175

Met Ala Glu Ala Tyr Ser Glu Ile Gly Met Lys Gly Glu Arg Arg Arg
            180                 185                 190

Gly Lys Gly His Asp Gly Leu Tyr Gln Gly Leu Ser Thr Ala Thr Lys
            195                 200                 205

Asp Thr Tyr Asp Ala Leu His Met Gln Ala Leu Pro Pro Arg
210                 215                 220

<210> SEQ ID NO 19
<211> LENGTH: 222
<212> TYPE: PRT
<213> ORGANISM: Unknown
<220> FEATURE:
<223> OTHER INFORMATION: Anti-p36 TCRAlpha sequence (Tctsv_p36A_28Z)

<400> SEQUENCE: 19

Pro Arg Lys Ile Glu Val Met Tyr Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
            100                 105                 110

Lys Phe Ser Arg Ser Ala Asp Ala Pro Ala Tyr Gln Gln Gly Gln Asn
            115                 120                 125

Gln Leu Tyr Asn Glu Leu Asn Leu Gly Arg Arg Glu Glu Tyr Asp Val
            130                 135                 140

Leu Asp Lys Arg Arg Gly Arg Asp Pro Glu Met Gly Gly Lys Pro Arg
145                 150                 155                 160

Arg Lys Asn Pro Gln Glu Gly Leu Tyr Asn Glu Leu Gln Lys Asp Lys
                165                 170                 175

Met Ala Glu Ala Tyr Ser Glu Ile Gly Met Lys Gly Glu Arg Arg Arg
            180                 185                 190

Gly Lys Gly His Asp Gly Leu Tyr Gln Gly Leu Ser Thr Ala Thr Lys
            195                 200                 205

Asp Thr Tyr Asp Ala Leu His Met Gln Ala Leu Pro Pro Arg
210                 215                 220

<210> SEQ ID NO 20
<211> LENGTH: 669
<212> TYPE: DNA
<213> ORGANISM: Unknown
<220> FEATURE:
<223> OTHER INFORMATION: Anti-p36 TCRBeta sequence (Tcstv_p36B_28Z)

<400> SEQUENCE: 20

```
cctaggaaga tcgaggtaat gtacccaccg ccctatctcg ataacgaaaa aagtaacggt    60
acaataattc acgttaaggg aaagcattta tgcccttccc cgttgttccc gggcccaagc   120
aaaccgtttt gggttctcgt agttgtaggc ggtgtgttag catgttactc tctccttgtt   180
acagtagctt tcataatctt ttgggtccga tcaaaacgct ctcgattgtt acattccgat   240
tatatgaata tgacaccgag gagacctggc ccgacgagga aacactatca accgtacgca   300
cctccgagag attttgctgc gtacaggagt cgtgtcaaat tttcacgctc cgctgatgcg   360
ccggcctatc aacaagggca aaatcaattg tacaatgaat tgaacttggg tcgtagagaa   420
gaatatgacg tactcgataa acggaggggg cgcgatccag aaatgggcgg caaaccacgg   480
cgaaaaaatc cacaagaggg attatataac gagttacaaa aggacaaaat ggcagaagca   540
tattcagaaa taggtatgaa gggggaaagg agacgaggga aaggtcatga cggattgtat   600
caaggattat cgaccgcgac taaagatacg tatgatgcgt tacacatgca agcattaccg   660
ccaagataa                                                            669
```

<210> SEQ ID NO 21
<211> LENGTH: 1191
<212> TYPE: DNA
<213> ORGANISM: Unknown
<220> FEATURE:
<223> OTHER INFORMATION: hu_CD4SignalpepECD sequence

<400> SEQUENCE: 21

```
atgaaccggg gagtcccttt taggcacttg cttctggtgc tgcaactggc gctcctccca    60
gcagccactc agggaaagaa agtggtgctg gcaaaaaaag gggatacagt ggaactgacc   120
tgtacagctt cccagaagaa gagcatacaa ttccactgga aaaactccaa ccagataaag   180
attctgggaa atcagggctc cttcttaact aaaggtccat ccaagctgaa tgatcgcgct   240
gactcaagaa gaagcctttg gaccaaggaa aactttcccc tgatcatcaa gaatcttaag   300
atagaagact cagatactta catctgtgaa gtggaggacc agaaggagga ggtgcaattg   360
ctagtgttcg gattgactgc caactctgac acccacctgc ttcagggggca gagcctgacc   420
ctgaccttgg agagcccccc tggtagtagc ccctcagtgc aatgtaggag tccaagggggt   480
aaaaacatac agggggggaa gaccctctcc gtgtctcagc tggagctcca ggatagtggc   540
acctggacat gcactgtctt gcagaaccag aagaaggtgg agttcaaaat agacatcgtg   600
gtgctagctt tccagaaggc ctccagcata gtctataaga agagggggaa acaggtggag   660
ttctccttcc cactcgcctt tacagttgaa aagctgacgg gcagtggcga gctgtggtgg   720
caggcggaga gggcttcctc ctccaagtct tggatcacct ttgacctgaa gaacaaggaa   780
gtgtctgtaa aacgggttac ccaggaccct aagctccaga tggcaagaa gctcccgctc   840
cacctcaccc tgcccaggc cttgcctcag tatgctggct ctggaaacct cacccctggcc   900
cttgaagcga aaacaggaaa gttgcatcag gaagtgaacc tggtggtgat gagagccact   960
cagctccaga aaaatttgac ctgtgaggtg tggggaccca cctcccctaa gctgatgctg  1020
agcttgaaac tggagaacaa ggaggcaaag gtctcgaagc gggagaaggc ggtgtgggtg  1080
```

```
ctgaaccctg aggcggggat gtggcagtgt ctgctgagtg actcgggaca ggtcctgctg      1140
gaatccaaca tcaaggttct gcccacatgg tccaccccgg tgcagccaat g               1191
```

<210> SEQ ID NO 22
<211> LENGTH: 1191
<212> TYPE: DNA
<213> ORGANISM: Unknown
<220> FEATURE:
<223> OTHER INFORMATION: Mu_hu_CD4SignalpepECD sequence

<400> SEQUENCE: 22

```
atgaaccgag gggtgccatt cagacatttg ctgcttgtcc tccagcttgc cctgcttcct       60
gccgcaactc aaggaaaaaa ggtcgtcctc gggaagaagg agacactgt tgagctaaca       120 tgcactgcat cgcaaaagaa gagtattcag tttcattgga agaattcaaa tcaaatcaaa      180
atactcggta accaagggtc gttttgaca agggaccctt cgaaactcaa cgaccgggca       240
gattctagga gaagtctatg ggatcagggt aatttcccgc tcataataaa aaacctaaaa      300
attgaggatt ctgacacata tatttgcgag gtcgaagatc aaaaagaaga agtccagtta      360
cttgtctttg gtttaacagc gaattcagat acgcatctcc tacaaggcca aagtctcacg      420
ctcacgttag aaagtccgcc aggaagcagt ccgtctgtcc agtgcagaag ccctagagga      480
aagaatattc aaggcggcaa aacgctgtcg gtctcacaac tcgaactgca agacagcggg      540
acgtggactt gtacagtgtt acaaaatcaa aaaaaggtcg aatttaagat tgatatagtc      600
gtccttgcat ttcaaaaagc gtcgagtatt gtgtacaaaa aggaaggcga gcaagtcgaa      660
ttttcgtttc ctctggcgtt cactgtagag aaactcaccg ggagcgggga actctggtgg      720
caagcggaaa gagcatcgtc gtcgaaatca tggattacgt tcgatctcaa aaataaagag      780
gtctcagtta agcgcgtaac gcaagatcca aaactgcaaa tggggaaaaa actgccctg      840 catctgacgc tcccgcaagc gttaccacaa tacgcagggt cagggaatct gacgctcgcg      900
ctagaggcca agactggtaa attacaccaa gaggtcaatc tcgtcgtcat gagggcgaca      960
caactgcaaa gaacttaacg tgcgaagtc tggggtccga cgtcgccaaa actcatgctc      1020
agtttaaagc tcgaaaataa agaagctaaa gtgtccaaac gcgaaaaagc cgtctgggtc      1080
ctcaatccag aagccggcat gtggcaatgc ctcctcagcg attccgggca agtgctcctc      1140
gagtcgaata ttaaagtact cccgacttgg tcgacgcccg tacaacctat g              1191
```

<210> SEQ ID NO 23
<211> LENGTH: 1602
<212> TYPE: DNA
<213> ORGANISM: Unknown
<220> FEATURE:
<223> OTHER INFORMATION: CD4_SignalpepECD_Z sequence

<400> SEQUENCE: 23

```
atgaaccggg gagtcccttt taggcacttg cttctggtgc tgcaactggc gctcctccca       60
gcagccactc agggaaagaa agtggtgctg ggcaaaaaag gggatacagt ggaactgacc      120
tgtacagctt cccagaagaa gagcatacaa ttccactgga aaaactccaa ccagataaag      180
attctgggaa atcagggctc cttcttaact aaaggtccat ccaagctgaa tgatcgcgct      240
gactcaagaa gaagcctttg ggaccaagga actttcccc tgatcatcaa gaatcttaag      300
atagaagact cagatactta catctgtgaa gtggaggacc agaaggagga ggtgcaattg      360
ctagtgttcg gattgactgc caactctgac acccaccctg ttcaggggca gagcctgacc      420
```

```
ctgaccttgg agagccccccc tggtagtagc ccctcagtgc aatgtaggag tccaagggt     480 aaaaacatac agggggggaa gaccctctcc gtgtctcagc tggagctcca ggatagtggc     540
acctggacat gcactgtctt gcagaaccag aagaaggtgg agttcaaaat agacatcgtg     600
gtgctagctt tccagaaggc ctccagcata gtctataaga agagggggga acaggtggag     660
ttctccttcc cactcgcctt tacagttgaa aagctgacgg gcagtggcga gctgtggtgg     720
caggcggaga gggcttcctc ctccaagtct tggatcacct ttgacctgaa gaacaaggaa     780
gtgtctgtaa acgggttac ccaggaccct aagctccaga tgggcaagaa gctcccgctc     840
cacctcaccc tgcccccaggc cttgcctcag tatgctggct ctggaaacct caccctggcc     900
cttgaagcga aaacaggaaa gttgcatcag gaagtgaacc tggtggtgat gagagccact     960
cagctccaga aaaatttgac ctgtgaggtg tggggaccca cctcccctaa gctgatgctg     1020
agcttgaaac tggagaacaa ggaggcaaag gtctcgaagc gggagaaggc ggtgtgggtg     1080
ctgaaccctg aggcggggat gtggcagtgt ctgctgagtg actcgggaca ggtcctgctg     1140
gaatccaaca tcaaggttct gcccacatgg tccaccccgg tgcagccaat ggatcccaaa     1200
ctctgctacc tgctggatgg aatcctcttc atctatggtg tcattctcac tgccttgttc     1260
ctgagagtga agttcagcag gagcgcagac gcccccgcgt accagcaggg ccagaaccag     1320
ctctataacg agctcaatct aggacgaaga gaggagtacg atgttttgga caagagacgt     1380
ggccgggacc ctgagatggg gggaaagccg agaaggaaga accctcagga aggcctgtac     1440
aatgaactgc agaaagataa gatggcggag gcctacagtg agattgggat gaaaggcgag     1500
cgccggaggg gcaaggggca cgatggcctt taccagggtc tcagtacagc caccaaggac     1560
acctacgacg cccttcacat gcaggccctg ccccctcgct aa                       1602
```

<210> SEQ ID NO 24
<211> LENGTH: 1524
<212> TYPE: DNA
<213> ORGANISM: Unknown
<220> FEATURE:
<223> OTHER INFORMATION: Mu_CD4_SignalpepECD_28 sequence

<400> SEQUENCE: 24

```
atgaaccgag gggtgccatt cagacatttg ctgcttgtcc tccagcttgc cctgcttcct     60
gccgcaactc aaggaaaaaa ggtcgtcctc gggaagaagg gagacactgt tgagctaaca     120
tgcactgcat cgcaaaagaa gagtattcag tttcattgga gaattcaaa tcaaatcaaa     180 atactcggta accaagggtc gtttttgaca aagggaccct tgaaactcaa cgaccgggca     240
gattctagga gaagtctatg ggatcagggt aatttcccgc tcataataaa aaacctaaaa     300
attgaggatt ctgacacata tatttgcgag gtcgaagatc aaaaagaaga agtccagtta     360
cttgtctttg gtttaacagc gaattcagat acgcatctcc tacaaggcca agtctcacg     420 ctcacgttag aaagtccgcc aggaagcagt ccgtctgtcc agtgcagaag ccctagagga     480
aagaatattc aaggcggcaa aacgctgtcg gtctcacaac tcgaactgca agacagcggg     540
acgtggactt gtacagtgtt acaaaatcaa aaaaggtcg aatttaagat tgatatagtc     600
gtccttgcat ttcaaaaagc gtcgagtatt gtgtacaaaa aggaaggcga gcaagtcgaa     660
ttttcgtttc ctctggcgtt cactgtagag aaactcaccg ggagcgggga actctggtgg     720
caagcggaaa gagcatcgtc gtcgaaatca tggattacgt tcgatctcaa aaataaagag     780
gtctcagtta agcgcgtaac gcaagatcca aaactgcaaa tggggaaaaa actgccctg     840 catctgacgc tcccgcaagc gttaccacaa tacgcagggt cagggaatct gacgctcgcg     900
```

-continued

```
ctagaggcca agactggtaa attacaccaa gaggtcaatc tcgtcgtcat gagggcgaca    960
caactgcaaa agaacttaac gtgcgaagtc tggggtccga cgtcgccaaa actcatgctc   1020
agtttaaagc tcgaaaataa agaagctaaa gtgtccaaac gcgaaaaagc cgtctgggtc   1080
ctcaatccag aagccggcat gtggcaatgc ctcctcagcg attccgggca agtgctcctc   1140
gagtcgaata ttaaagtact cccgacttgg tcgacgcccg tacaacctat gcctaggaaa   1200
attgaagtta tgtatcctcc tccttaccta gacaatgaga agagcaatgg aaccattatc   1260
catgtgaaag ggaaacacct ttgtccaagt cccctatttc ccggaccttc taagcccttt   1320
tgggtgctgg tggtggttgg tggagtcctg gcttgctata gcttgctagt aacagtggcc   1380
tttattattt tctgggtgag gagtaagagg agcaggctcc tgcacagtga ctacatgaac   1440
atgactcccc gccgcccgg gcccacccgc aagcattacc agccctatgc cccaccacgc   1500
gacttcgcag cctatcgctc ctaa                                         1524
```

<210> SEQ ID NO 25
<211> LENGTH: 42
<212> TYPE: DNA
<213> ORGANISM: Unknown
<220> FEATURE:
<223> OTHER INFORMATION: MuCD3Z_ F1_primer

<400> SEQUENCE: 25

```
tgcggagact tggatcctaa gttatgttat ttattagacg gg                        42
```

<210> SEQ ID NO 26
<211> LENGTH: 61
<212> TYPE: DNA
<213> ORGANISM: Unknown
<220> FEATURE:
<223> OTHER INFORMATION: MuCD3Z_ R1_primer

<400> SEQUENCE: 26

```
aaatagcgct gttaatatca ctccgtatat aaataaaatc ccgtctaata aataacataa    60
c                                                                     61
```

<210> SEQ ID NO 27
<211> LENGTH: 49
<212> TYPE: DNA
<213> ORGANISM: Unknown
<220> FEATURE:
<223> OTHER INFORMATION: MuCD3Z_ F2_primer

<400> SEQUENCE: 27

```
gtgatattaa cagcgctatt tttacgtgtc aaattttcac gctccgctg                 49
```

<210> SEQ ID NO 28
<211> LENGTH: 93
<212> TYPE: DNA
<213> ORGANISM: Unknown
<220> FEATURE:
<223> OTHER INFORMATION: MuCD3Z_ R2_primer

<400> SEQUENCE: 28

```
ttcttctcta cgacccaagt tcaattcatt gtacaattga ttttgcccatt gttgataggc   60 cggcgcatca gcggagcgtg aaaatttgac acg                                  93
```

<210> SEQ ID NO 29
<211> LENGTH: 92
<212> TYPE: DNA

```
<213> ORGANISM: Unknown
<220> FEATURE:
<223> OTHER INFORMATION: MuCD3Z_ F3_primer

<400> SEQUENCE: 29
cttgggtcgt agagaagaat atgacgtact cgataaacgg aggggggcgcg atccagaaat    60 gggcggcaaa ccacggcgaa aaatccaca ag                                   92

<210> SEQ ID NO 30
<211> LENGTH: 94
<212> TYPE: DNA
<213> ORGANISM: Unknown
<220> FEATURE:
<223> OTHER INFORMATION: MuCD3Z_ R3_primer

<400> SEQUENCE: 30 cccccttcata cctatttctg aatatgcttc tgccattttg tccttttgta actcgttata    60
taatccctct tgtggatttt ttcgccgtgg tttg                                 94

<210> SEQ ID NO 31
<211> LENGTH: 97
<212> TYPE: DNA
<213> ORGANISM: Unknown
<220> FEATURE:
<223> OTHER INFORMATION: MuCD3Z_ F4_primer

<400> SEQUENCE: 31
ttcagaaata ggtatgaagg gggaaaggag acgagggaaa ggtcatgacg gattgtatca    60
aggattatcg accgcgacta aagatacgta tgatgcg                             97

<210> SEQ ID NO 32
<211> LENGTH: 64
<212> TYPE: DNA
<213> ORGANISM: Unknown
<220> FEATURE:
<223> OTHER INFORMATION: MuCD3Z_ R4_StopBsepI_primer

<400> SEQUENCE: 32
acgatccgga cttatcttgg cggtaatgct tgcatgtgta acgcatcata cgtatcttta    60
gtcg                                                                 64

<210> SEQ ID NO 33
<211> LENGTH: 669
<212> TYPE: DNA
<213> ORGANISM: Unknown
<220> FEATURE:
<223> OTHER INFORMATION: CD28CD3Zeta sequence

<400> SEQUENCE: 33
cctaggaaaa ttgaagttat gtatcctcct ccttacctag acaatgagaa gagcaatgga    60
accattatcc atgtgaaagg gaaacacctt tgtccaagtc cctatttcc cggaccttct    120 aagccctttt gggtgctggt ggtggttggt ggagtcctgg cttgctatag cttgctagta    180
acagtggcct ttattatttt ctgggtgagg agtaagagga gcaggctcct gcacagtgac    240
tacatgaaca tgactccccg ccgcccgggg ccacccgca agcattacca gccctatgcc    300
ccaccacgcg acttcgcagc ctatcgctcc agagtgaagt tcagcaggag cgcagacgcc    360
cccgcgtacc agcagggcca gaaccagctc tataacgagc tcaatctagg acgaagagag    420
gagtacgatg ttttggacaa gagacgtggc cgggaccctg atgggggg aaagccgaga    480 aggaagaacc ctcaggaagg cctgtacaat gaactgcaga agataagat ggcggaggcc    540
```

```
tacagtgaga ttgggatgaa aggcgagcgc cggaggggca aggggcacga tggcctttac    600
cagggtctca gtacagccac caaggacacc tacgacgccc ttcacatgca ggccctgccc    660
cctcgctaa                                                            669
```

<210> SEQ ID NO 34
<211> LENGTH: 669
<212> TYPE: DNA
<213> ORGANISM: Unknown
<220> FEATURE:
<223> OTHER INFORMATION: Mutated CD28CD3Zeta sequence

<400> SEQUENCE: 34

```
cctaggaaga tcgaggtaat gtacccaccg ccctatctcg ataacgaaaa aagtaacggt     60
acaataattc acgttaaggg aaagcattta tgcccttccc cgttgttccc gggcccaagc    120
aaaccgttct gggttctcgt agttgtaggc ggtgtgttag catgttactc tctccttgtt    180
acagtagctt tcataatctt tgggtccga tcaaaacgct ctcgattgtt acattccgat     240
tatatgaata tgacaccgag gagacctggc ccgacgagga aacactatca accgtacgca    300
cctccgagag attttgctgc gtacaggagt cgtgtcaaat tttcacgctc cgctgatgcg    360
ccggcctatc aacaagggca aaatcaattg tacaatgaat tgaacttggg tcgtagagaa    420
gaatatgacg tactcgataa acggaggggg cgcgatccag aaatgggcgg caaaccacgg    480
cgaaaaaatc cacaagaggg attatataac gagttacaaa aggacaaaat ggcagaagca    540
tattcagaaa taggtatgaa gggggaaagg agacgaggga aaggtcatga cggattgtat    600
caaggattat cgaccgcgac taaagatacg tatgatgcgt tacacatgca agcattaccg    660
ccaagataa                                                            669
```

<210> SEQ ID NO 35
<211> LENGTH: 414
<212> TYPE: DNA
<213> ORGANISM: Unknown
<220> FEATURE:
<223> OTHER INFORMATION: TcSv anti-JCV TCR construct of wtCD3z

<400> SEQUENCE: 35

```
ctggatccca aactctgcta cctgctggat ggatcctctt catctatggt gtcattctca     60
ctgccttgtt cctgagagtg aagttcagca ggagcgcaga cgcccccgcg taccagcagg    120
gcccagaacc agctctataa cgagctcaat ctaggacgaa gagaggagta cgatgttttg    180
gacaagagac gtggccggga ccctgagatg ggggaaagc cgagaaggaa gaaccctcag    240
gaaggcctgt acaatgaact gcagaaagat aagatggcgg aggcctacag tgagattggg    300
atgaaaggcg agcgccggag gggcaagggg cacgatggcc tttaccaggg tctcagtaca    360
gccaccaagg acacctacga cgcccttcac atgcaggccc tgccccctcg ctaa          414
```

<210> SEQ ID NO 36
<211> LENGTH: 414
<212> TYPE: DNA
<213> ORGANISM: Unknown
<220> FEATURE:
<223> OTHER INFORMATION: TcSv anti-JCV TCR construct of dCD3z

<400> SEQUENCE: 36

```
ctggatccca aattgtgtta tttgttggac gggatttat ttatatacgg agtgatatta      60
acagcgctat ttttacgtgt caaattttca cgctccgctg atgcgccggc ctatcaacaa    120
```

```
gggcaaaatc aattgtacaa tgaattgaac ttgggtcgta gagaagaata tgacgtactc      180
gataaacgga gggggcgcga tccagaaatg ggcggcaaac cacggcgaaa aaatccacaa      240
gagggattat ataacgagtt acaaaaggac aaaatggcag aagcatattc agaaataggt      300 atgaagggg  aaaggagacg agggaaaggt catgacggat tgtatcaagg attatcgacc      360
gcgactaaag atacgtatga tgcgttacac atgcaagcat taccgccaag ataa            414
```

<210> SEQ ID NO 37
<211> LENGTH: 137
<212> TYPE: PRT
<213> ORGANISM: Unknown
<220> FEATURE:
<223> OTHER INFORMATION: amino acid sequence of TcSv anti-JCV TCR
      construct for wtCD3z and dCD3z

<400> SEQUENCE: 37

```
Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys Phe Ser Arg Ser
                20                  25                  30

Ala Asp Ala Pro Ala Tyr Gln Gln Gly Gln Asn Gln Leu Tyr Asn Glu
            35                  40                  45

Leu Asn Leu Gly Arg Arg Glu Glu Tyr Asp Val Leu Asp Lys Arg Arg
        50                  55                  60

Gly Arg Asp Pro Glu Met Gly Gly Lys Pro Arg Arg Lys Asn Pro Gln
65                  70                  75                  80

Glu Gly Leu Tyr Asn Glu Leu Gln Lys Asp Lys Met Ala Glu Ala Tyr
                85                  90                  95

Ser Glu Ile Gly Met Lys Gly Glu Arg Arg Arg Gly Lys Gly His Asp
            100                 105                 110

Gly Leu Tyr Gln Gly Leu Ser Thr Ala Thr Lys Asp Thr Tyr Asp Ala
        115                 120                 125

Leu His Met Gln Ala Leu Pro Pro Arg
    130                 135
```

US 10,550,176 B2

VIRAL VECTORS ENCODING MULTIPLE HIGHLY HOMOLOGOUS NON-VIRAL POLYPEPTIDES AND THE USE OF SAME

CROSS-REFERENCE TO RELATED APPLICATIONS

This application is a division of U.S. application Ser. No. 13/145,488, filed Jan. 26, 2012, now allowed, which is the U.S. National Stage of International Application No. PCT/US2010/021825, filed Jan. 22, 2010, which claims the benefit of U.S. Provisional Application No. 61/146,755, filed on Jan. 23, 2009. The entire teachings of the above applications are incorporated herein by reference.

GOVERNMENT SUPPORT

The invention was made with government support under grant number AI060550 awarded by the National Institutes of Health. The Government has certain rights in the invention.

CROSS-REFERENCE TO A SEQUENCE USING

A "Sequence Listing" is submitted with this application in the form of a text file, created Dec. 4, 2015, and named "09620100838011US01sequencelisting.txt" (33000 bytes), the contents of which are incorporated herein by reference in their entirety.

BACKGROUND OF THE INVENTION

Recombination between nucleic acids is a well-established phenomenon in molecular biology. Genetic recombination that requires strong sequence homology between participating nucleic acid sequences to occur is generally referred to as homologous recombination. While most genetic knockout strategies employ homologous recombination to achieve a targeted knockout, in certain systems the occurrence of genetic recombination can impact genetic manipulations detrimentally. In particular, homologous recombination events can adversely impact construction and production of vectors, particularly viral vectors (e.g., adenovirus, retrovirus, adeno-associated virus, herpes virus, etc.), where it is often desirable to maintain highly homologous sequences (e.g., identical polypeptide sequences) within a single, stable viral vector free of homologous recombination during, e.g., passage and/or propagation of viral vector through one or more host cells and/or organisms.

In bacteria, homologous recombination begins with a step that involves a single-stranded end (Meselson and Radding 1975 *Proc. Natl. Acad. Sci. USA,* 80: 358-361). In eukaryotes, a mechanism of double-strand break (DSB) (Szostak et al. 1983 *Cell* 33: 25-35) has been suggested. DSB appears to occur in two principal mechanisms of homologous recombination: one conservative, within which all the nucleic acid sequences participating in the recombination event are present in the recombination products (ibid), the other nonconservative, during which certain sequences are lost. In mammalian somatic cells, the majority of homologous recombination events by DSB appears to take place according to a nonconservative process (Lin et al. 1990 *Mol Cell Biol.* 10: 103-12).

During the production of recombinant proteins, recombination events within an expression plasmid (intramolecular homologous recombination) can, for example, lead to the excision of the expression cassette from the transgene, resulting in a loss of expression. Recombination events can also produce excision of an expression cassette which has been stably integrated into the genome of a host producer cell, thereby inducing a loss of stability. Because of the potential for deleterious impact of homologous recombination events during vector production, particularly viral vector production, a need exists for effective strategies to reduce or eliminate the occurrence of homologous recombination events during synthesis of vectors, particularly viral vectors. Accordingly, there is also a need for vector compositions that possess reduced susceptibility to the occurrence of homologous recombination events, particularly viral vectors comprising, within a single vector, nucleic acid sequences that are designed to protect against the occurrence of homologous recombination events between those sequences encoding highly homologous polypeptides.

SUMMARY OF THE INVENTION

The present invention relates, at least in part, to the discovery of a strategy for synthesis of a vector, viral vector and/or recombinant virus having two or more nucleic acid sequences encoding polypeptides that are identical or are of high homology to one another, wherein these nucleic acid sequences are, by design, of significantly lower homology to one another than their encoded polypeptide sequences. Design of such nucleic acid sequences of significantly lowered homology can be achieved via mutation of at least one nucleic acid sequence using degenerate codons—an approach that exploits the degeneracy of the genetic code. Inclusion of such mutated nucleic acid sequences that still encode highly homologous polypeptides within a single vector can dramatically lessen the probability of homologous recombination events occurring between nucleic acid sequences within such a vector, as compared to the rate of homologous recombination expected and/or observed for a vector that comprises two or more native (or otherwise unaltered) nucleic acid sequences encoding highly homologous polypeptides. Thus, a vector, viral vector and/or recombinant virus of the instant invention can be generated, extensively propagated in host cells, and utilized in, e.g., gene therapy of a subject, with high probability that both homologous polypeptide sequences are present and expressed within a host cell and/or target cell of the subject, even, e.g., following extensive preparative passaging, replication, propagation, administration and/or chromosomal integration, excision, etc.

In certain aspects of the invention, the synthesis of viral vectors by the process of the invention is particularly advantageous for gene therapy of mammalian immune cells (e.g., T cells, NK cells, macrophages), especially T cells. Accordingly, specific aspects of the present invention provide a viral vector having two or more nucleic acid sequences that each encodes a chimeric immune receptor (CIR) polypeptide, wherein the nucleic acid sequences, or fragments thereof, are, by design, of significantly lower homology to one another than their encoded polypeptide sequences. Introduction of such viral vectors to T cells allows for efficient concurrent expression of highly homologous CIRs within a T cell, which in turn allows for higher affinity targeting of a specific ligand (e.g., via expression of both ☐ and ☐ chains of an antigen binding fragment of an antibody that binds a targeted antigen with higher specificity than would be provided by a single chain antigen binding fragment), as well as enhanced T cell activation (e.g., via simultaneous expression of co-activating molecules on a single host cell). Other aspects of the invention provide methods for therapeutic administration of such viral vectors to a host cell and/or target cell of a subject in need thereof, either ex vivo or in vivo, for the purpose of treating, e.g., cancer and/or an infectious disease in the subject.

In one aspect, the instant invention provides a viral vector comprising a first nucleic acid sequence encoding a first polypeptide sequence and a second nucleic acid sequence encoding a second polypeptide sequence, wherein the first polypeptide sequence and the second polypeptide sequence comprise an identical polypeptide sequence of greater than 15 amino acids in length; and the first nucleic acid sequence and the second nucleic acid sequence contain at least one non-identical codon within the codons that encode the identical polypeptide sequence of the first and second nucleic acid sequences.

In another aspect, the instant invention provides a viral vector comprising a first nucleic acid sequence encoding a first polypeptide sequence and a second nucleic acid sequence encoding a second polypeptide sequence, wherein the first polypeptide sequence comprises a polypeptide sequence of greater than 15 amino acids in length that is greater than 90% identical to the second polypeptide sequence; and the first nucleic acid sequence and the second nucleic acid sequence contain at least one non-identical codon that encodes an identical amino acid residue, wherein the greater than 90% identical polypeptide sequence of the first and second nucleic acid sequences comprises the identical amino acid residue.

In one embodiment, at least one of the first and second nucleic acid sequences of the viral vector is a synthetic sequence. In another embodiment, the level of homology between the first and the second nucleic acid sequences of the viral vector is insufficient to cause homologous recombination between the first and the second nucleic acid sequences in a cell. In one related embodiment, the cell is a bacterial cell. In an additional related embodiment, the cell is a host cell.

In certain embodiments, the viral vector of the instant invention is selected from the group consisting of an adenovirus vector, an adeno-associated virus vector, a retrovirus vector, and a herpes virus vector.

In an additional embodiment, the first and second nucleic acid sequences of the viral vector encode non-viral polypeptide sequences. In another embodiment, the first and second nucleic acid sequences of the viral vector encode mammalian polypeptide sequences. In a further embodiment, the first and second nucleic acid sequences of the viral vector encode human polypeptide sequences.

In certain embodiments, the viral vector is a retroviral vector. In a related embodiment, the retroviral vector is selected from the group consisting of avian sarcoma-leukosis virus (ASLV), murine leukemia virus (MLV), human-, simian-, feline-, and bovine immunodeficiency viruses (HIV, SIV, FIV, BIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), MFG, FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV), AKR (endogenous) murine leukemia virus, Avian carcinoma, Mill Hill virus 2, Avian leukosis virus—RSA, Avian myeloblastosis virus, Avian myelocytomatosis virus 29, Bovine syncytial virus, Caprine arthritis encephalitis virus, Chick syncytial virus, Equine infectious anemia virus, Feline leukemia virus, Feline syncytial virus, Finkel-Biskis-Jinkins murine sarcoma virus, Friend murine leukemia virus, Fujinami sarcoma virus, Gardner-Arnstein feline sarcoma virus, Gibbon ape leukemia virus, Guinea pig type C oncovirus, Hardy-Auckerman feline sarcoma virus, Harvey murine sarcoma virus, Human foamy virus, Human spumavirus, Human T-lymphotropic virus 1, Human T-lymphotropic virus 2, Jaagsiekte virus, Kirsten murine sarcoma virus, Langur virus, Mason-Pfizer monkey vikrus, Mouse mammary tumor virus, Ovine pulmonary adenocarcinoma virus, Porcine type C oncovirus, Reticuloendotheliosis virus, Rous sarcoma virus, Simian foamy virus, Simian sarcoma virus, Simian T-lymphotropic virus, Simian type D virus 1, Snyder-Theilen feline sarcoma virus, Squirrel monkey retrovirus, Trager duck spleen necrosis virus, UR2 sarcoma virus, Viper retrovirus, Visna/maedi virus, Woolly monkey sarcoma virus, and Y73 sarcoma virus.

In another embodiment, at least 20% of the codons encoding the at least one identical polypeptide domain of the first and second nucleic acid sequences are non-identical. In a further embodiment, the first nucleic acid sequence and the second nucleic acid sequence are less than 80% identical to one another within the codons that encode the at least one identical polypeptide domain of the first and second nucleic acid sequences.

In an additional embodiment, at least one of the first and second polypeptide sequences encoded by the viral vector is a chimeric immune receptor polypeptide sequence. In a related embodiment, at least one of the first and second polypeptide sequences is a chimeric immune receptor polypeptide sequence comprising a signal sequence that directs the polypeptide to the cell surface. In a further embodiment, the signal sequence that directs the polypeptide to the cell surface is selected from the group consisting of TCR-α, TCR-β, TCR-γ, TCR-δ, IgG, IgA, IgM, IgE, IgD, CD2, CD4, CD8, CD28, CD3ζ, FcεRIγ, and LFA-1. In another embodiment, at least one of the first and second polypeptide sequences is a chimeric immune receptor (CIR) polypeptide sequence comprising an extracellular binding domain selected from the group consisting of a surface membrane polypeptide that binds specifically to at least one ligand and a secreted polypeptide that binds specifically to at least one ligand.

In certain embodiments, at least one of the first and second polypeptide sequences is a chimeric immune receptor polypeptide sequence comprising a transmembrane domain selected from the group consisting of TCR-α, TCR-β, TCR-γ, TCR-δ, IgG, IgA, IgM, IgE, IgD, CD2, CD4, CD8, CD28, CD3ζ, FcεRIγ, and LFA-1. In some embodiments, at least one of the first and second polypeptide sequences is a chimeric immune receptor polypeptide sequence comprising an intracellular cytoplasmic domain selected from the group consisting of a CD3ζ cytoplasmic domain or a functional fragment thereof, a CD28 cytoplasmic domain or a functional fragment thereof, a polypeptide that combines CD28 and CD3ζ polypeptide sequences or a functional fragment thereof, and an FcεRIγ cytoplasmic domain or a functional fragment thereof. In one embodiment, at least one of the first and second polypeptide sequences is a chimeric immune receptor polypeptide sequence comprising a signal sequence which directs the polypeptide to the cell surface; an extracellular binding domain that is a surface membrane polypeptide that binds specifically to at least one ligand or a secreted polypeptide that binds specifically to at least one ligand; a transmembrane domain; and an intracellular cytoplasmic domain that is a CD3ζ cytoplasmic domain or a functional fragment thereof, a CD28 cytoplasmic domain or a functional fragment thereof, a polypeptide that combines CD28 and CD3ζ polypeptide sequences or a functional fragment thereof, a CD2 cytoplasmic domain or a functional fragment thereof, a LFA-1 polypeptide sequence or a functional fragment thereof, or an FcεRIγ cytoplasmic domain or a functional fragment thereof.

In one embodiment, the viral vector comprises an altered (mutant) nucleic acid sequence that is the mutant sequence shown in FIG. 2, the mutant sequence shown in FIG. 4, the mutant sequence shown in FIG. 6, the mutant sequence shown in FIG. 16, the mutant sequence shown in FIG. 19, the mutant sequence shown in FIG. 21, or the mutant sequence shown in FIG. 22.

In another embodiment, one of the first and second nucleic acid sequences is the mutant sequence shown in FIG. 2, the mutant sequence shown in FIG. 4, the mutant sequence shown in FIG. 6, the mutant sequence shown in FIG. 16, the mutant sequence shown in FIG. 19, the mutant sequence shown in FIG. 21, or the mutant sequence shown in FIG. 22, or a functional fragment thereof.

In additional embodiments, the instant invention provides a cell or recombinant virus comprising the viral vector.

Another aspect of the instant invention provides a host cell comprising a viral vector comprising a first nucleic acid sequence encoding a first polypeptide sequence and a second nucleic acid sequence encoding a second polypeptide sequence, wherein the first and second polypeptide sequences comprise at least one identical polypeptide domain of greater than 15 amino acids in length and the first nucleic acid sequence and the second nucleic acid sequence do not undergo homologous recombination with one another.

In one embodiment, at least one of the first and second polypeptide sequences is a mammalian polypeptide sequence. In another embodiment, the viral vector is integrated in the host cell genome.

In an additional embodiment, the viral vector is a retroviral vector. In a related embodiment, the retroviral vector is a lentiviral vector.

In a further embodiment, at least 20% of the codons of the host cell viral vector encoding the identical polypeptide sequence of the first and second nucleic acid sequences contain at least one non-identical nucleic acid that reduces identity between the first and second nucleic acid sequences. In another embodiment, the first nucleic acid sequence and the second nucleic acid sequence of the host cell viral vector are less than 80% identical.

In another embodiment, the host cell is an immune cell. In a related embodiment the host cell is an immune cell that is a natural killer cell, a lymphokine activated cell, a cytotoxic T cell, or a helper T cell or a subtype thereof. In one embodiment, the host cell is a human T cell. In an additional embodiment, the host cell is a hematopoietic stem cell. In a further embodiment, the host cell is a tumor infiltrating lymphocyte.

In certain embodiments, at least one of the first and second polypeptide sequences of the host cell viral vector is a chimeric immune receptor sequence. In one embodiment, the chimeric immune receptor sequence of the host cell viral vector comprises a signal sequence that directs the polypeptide to the cell surface. In a related embodiment, the signal sequence that directs the polypeptide to the cell surface is that of a TCR-α, TCR-β, TCR-γ, TCR-δ, IgG, IgA, IgM, IgE, IgD, CD2, CD4, CD8, CD28, CD3ζ, FcεRIγ, or LFA-1.

In an additional embodiment, the chimeric immune receptor of the host cell viral vector comprises an extracellular binding domain selected from the group consisting of a surface membrane polypeptide that binds specifically to at least one ligand and a secreted polypeptide that binds specifically to at least one ligand. In one embodiment, the chimeric immune receptor comprises a transmembrane domain of TCR-α, TCR-β, TCR-γ, TCR-δ, IgG, IgA, IgM, IgE, IgD, CD2, CD4, CD8, CD28, CD3ζ, FcεRIγ, or LFA-1.

In another embodiment, the chimeric immune receptor of the host cell viral vector comprises an intracellular cytoplasmic domain of a CD3ζ cytoplasmic domain or a functional fragment thereof, a CD28 cytoplasmic domain or a functional fragment thereof, a polypeptide that combines CD28 and CD3ζ polypeptide sequences or a functional fragment thereof, a CD2 cytoplasmic domain or a functional fragment thereof, a LFA-1 polypeptide sequence or a functional fragment thereof, or an FcεRIγ cytoplasmic domain or a functional fragment thereof.

In certain embodiments of the instant invention, the chimeric immune receptor of the host cell viral vector comprises a signal sequence which directs the polypeptide to the cell surface; an extracellular binding domain of a surface membrane polypeptide that binds specifically to at least one ligand or a secreted polypeptide that binds specifically to at least one ligand; a transmembrane domain; and an intracellular cytoplasmic domain of a CD3ζ cytoplasmic domain or a functional fragment thereof, a CD28 cytoplasmic domain or a functional fragment thereof, a polypeptide that combines CD28 and CD3ζ polypeptide sequences or a functional fragment thereof, a CD2 cytoplasmic domain or a functional fragment thereof, a LFA-1 polypeptide sequence or a functional fragment thereof, or an FcεRIγ cytoplasmic domain or a functional fragment thereof. In one embodiment, the host cell viral vector comprises a mutant nucleic acid sequence selected from the group consisting of the mutant sequence shown in FIG. 2, the mutant sequence shown in FIG. 4, the mutant sequence shown in FIG. 6, the mutant sequence shown in FIG. 16, the mutant sequence shown in FIG. 19, the mutant sequence shown in FIG. 21, and the mutant sequence shown in FIG. 22. In another embodiment, one of the first and second nucleic acid sequences of the host cell viral vector is a mutant nucleic acid sequence selected from the group consisting of the mutant sequence shown in FIG. 2, the mutant sequence shown in FIG. 4, the mutant sequence shown in FIG. 6, the mutant sequence shown in FIG. 16, the mutant sequence shown in FIG. 19, the mutant sequence shown in FIG. 21, and the mutant sequence shown in FIG. 22, or a functional fragment thereof.

Another aspect of the instant invention provides a cell comprising a recombinant virus comprising an altered (mutant) nucleic acid sequence that is the mutant sequence shown in FIG. 2, the mutant sequence shown in FIG. 4, the mutant sequence shown in FIG. 6, the mutant sequence shown in FIG. 16, the mutant sequence shown in FIG. 19, the mutant sequence shown in FIG. 21, or the mutant sequence shown in FIG. 22.

An additional aspect of the instant invention provides a viral vector comprising a first nucleic acid sequence encoding a first polypeptide sequence and a second nucleic acid sequence encoding a second polypeptide sequence, wherein the first polypeptide sequence and the second polypeptide sequence each comprises an identical CD3ζ polypeptide sequence or functional fragment thereof; and the first nucleic acid sequence and the second nucleic acid sequence contain at least one non-identical codon within the codons encoding the identical CD3ζ polypeptide sequence or functional fragment thereof of the first and second nucleic acid sequences. In one embodiment, the identical CD3ζ polypeptide sequence encoded by the viral vector is cytoplasmic.

A further aspect of the instant invention provides a viral vector comprising a first nucleic acid sequence encoding a first polypeptide sequence and a second nucleic acid sequence encoding a second polypeptide sequence, wherein the first polypeptide sequence and the second polypeptide sequence each comprises an identical CD28 polypeptide sequence or functional fragment thereof; and the first nucleic acid sequence and the second nucleic acid sequence contain at least one non-identical codon within the codons encoding the identical CD28 polypeptide sequence or functional fragment thereof of the first and second nucleic acid sequences.

Another aspect of the instant invention provides a viral vector comprising a first nucleic acid sequence encoding a first polypeptide sequence and a second nucleic acid sequence encoding a second polypeptide sequence, wherein the first polypeptide sequence and the second polypeptide sequence each comprises an identical FcεR1 polypeptide sequence or functional fragment thereof; and the first nucleic acid sequence and the second nucleic acid sequence contain at least one non-identical codon within the codons encoding the identical FcεR1 polypeptide sequence or functional fragment thereof of the first and second nucleic acid sequences.

An additional aspect of the instant invention provides a viral vector comprising a first nucleic acid sequence encoding a first polypeptide sequence and a second nucleic acid sequence encoding a second polypeptide sequence, wherein the first polypeptide sequence and the second polypeptide sequence each comprises an identical single chain antibody polypeptide sequence or functional fragment thereof; and the first nucleic acid sequence and the second nucleic acid sequence contain at least one non-identical codon within the codons encoding the identical single chain antibody polypeptide sequence or functional fragment thereof of the first and second nucleic acid sequences. In one embodiment, the single chain antibody polypeptide sequence is an anti-CEA scFv or an anti-PSMA scFv.

A further aspect of the instant invention provides a viral vector comprising a first nucleic acid sequence encoding a first polypeptide sequence and a second nucleic acid sequence encoding a second polypeptide sequence wherein the first polypeptide sequence and the second polypeptide sequence each comprises an identical polypeptide sequence comprising a target-binding domain or functional fragment thereof; and the first nucleic acid sequence and the second nucleic acid sequence contain at least one non-identical codon within the codons that encode the identical target-binding domain or functional fragment thereof of the first and second nucleic acid sequences. In one embodiment, the target-binding domain of the viral vector binds an antigen. In one embodiment, the antigen is HIV-1 gp120, for which the target-binding domain or functional fragment thereof is a human CD4 extracellular domain or functional fragment thereof. In a further embodiment, the target-binding domain or functional fragment thereof is a single chain antibody, or fragment antigen-binding (Fab). In a related embodiment, the antigen is a viral antigen or a tumor antigen. In a related embodiment, the antigen is selected from the group consisting of MHC presented peptides as tumor antigens (such as MAGE-1) or viral antigens (such as JC virus VP1) for which CIR are created with target binding domains of TCR or antibody in single chain or other format.

Another embodiment of the instant invention provides a method for inhibiting growth of a tumor in a subject comprising administering a virus comprising the viral vector of the invention to the subject, thereby inhibiting the growth of the tumor.

An additional embodiment of the instant invention provides a method for reducing the size of a tumor in a subject comprising administering a virus comprising the viral vector of the invention to the subject, thereby reducing the size of the tumor. In one embodiment, the tumor is a prostate cancer tumor, a lung cancer tumor, a breast cancer tumor, or a colorectal cancer tumor.

A further embodiment of the instant invention provides a method for inhibiting proliferation of a cancer cell in a subject comprising administering a virus comprising the viral vector of the invention to the subject, thereby inhibiting proliferation of the cancer cell in the subject. In certain embodiments, the cancer cell is selected from the group consisting of a leukemia cancer cell, an AML cancer cell, and an ALL cancer cell.

In one embodiment, the virus is administered with a pharmaceutically acceptable carrier.

In another embodiment, the instant invention provides a method for inhibiting the proliferation of an infectious agent in a subject comprising administering a virus comprising the viral vector of the invention to the subject, thereby inhibiting proliferation of the infectious agent. In a related embodiment, the infectious agent is polyomavirus JC (JCV), HIV, HBV, HCV, CMV, or EBV.

In an additional embodiment, the instant invention provides a method for killing a virus-infected cell of a subject comprising administering a virus comprising the viral vector of the invention to the subject, thereby killing the virus-infected cell of the subject.

In another embodiment, the instant invention provides a method for treatment of a tumor or infectious disease in a subject comprising transforming lymphocyte cells with the viral vector of the invention, wherein the extracellular binding domain is a scFv domain of an antibody directed against the tumor or infectious disease, and administering the transformed cells to the subject, wherein the transformed lymphocyte cells are targeted to the tumor cells or infectious disease, thereby treating the subject. In one embodiment, the lymphocyte cells are lymphocyte cells of the subject. In an additional embodiment, peripheral blood cells of the subject are transformed. In a further embodiment, hematopoietic stem cells of the subject are transformed. In another embodiment, primary T cells of the subject are transformed.

A further embodiment of the instant invention provides a method for generating a host cell that contains a viral vector comprising at least two non-viral nucleic acid sequences encoding at least one identical polypeptide sequence of greater than 15 amino acids in length comprising introducing the viral vector of the invention into a host cell, thereby generating the host cell. In one embodiment, the method further comprises selecting for the presence of the viral vector in the host cell. In an additional embodiment, the step of selecting for presence of the viral vector in the host cell includes identifying viral particles in the host cell media. In another embodiment, at least one of the first or second polypeptide is a CIR or a functional fragment thereof.

In an additional embodiment, at least one of the CIR polypeptide sequences contains a transmembrane domain (TMD) sequence of CD3ζ TMD sequence, CD28 TMD sequence, CD8 TMD sequence, CD4 TMD sequence, or FcεRIγ TMD sequence, or a variant polypeptide or functional fragment thereof.

In another embodiment, at least one of the CIR polypeptides contains an N-terminal signal sequence of TCR-α, TCR-β, TCR-γ, TCR-δ, IgG, IgA, IgM, IgE, IgD, CD2, CD4, CD8, CD28, CD3ζ, FcεRIγ, or LFA-1.

In a further embodiment, at least one of the CIR polypeptides contains an extracellular binding domain of a surface membrane polypeptide. In certain embodiments, the extracellular binding domain of the surface membrane polypeptide binds specifically to at least one ligand or antigen.

In an additional embodiment, at least one of the CIR polypeptides contains an extracellular binding domain of a secreted polypeptide that binds specifically to at least one ligand or antigen.

In a further embodiment, at least one of the CIR polypeptides contains an intracellular cytoplasmic domain that is the CD3zeta intracellular cytoplasmic domain sequence, CD28 intracellular cytoplasmic domain sequence, CD8 intracellular cytoplasmic domain sequence, CD4 intracellular cytoplasmic domain sequence or Fc(e)RIgamma intracellular cytoplasmic domain sequence, or a variant polypeptide or functional fragment thereof. In certain embodiments, the ligand or antigen is a cancer cell ligand or antigen. In one embodiment, the cancer cell ligand or antigen is cyclin-dependent kinase-4, β-catenin, Caspase-8, MAGE-1, MAGE-3, Tyrosinase, Surface Ig idiogype, Her-2/neu, MUC-1, HPV E6, HPV E7, CD5, idiotype, CAMPATH-1, CD20, CEA, mucin-1, Lewis$^x$, CA-125, EGFR, p185$^{HER2}$, IL-2R, FAP-α, Tenascin, or a metalloproteinase. In another embodiment, the ligand or antigen is an infectious disease ligand or antigen. In a related embodiment, the infectious disease ligand or antigen is selected from the group consisting of CTL epitopes of HIV, CMV, EBV, HBV, and HCV. In one embodiment, the infectious disease ligand or antigen is HIV gp120 or HIV gp41.

In another embodiment, the extracellular domains of the first and second polypeptide sequences comprise the immunoglobulin heavy and light chains of an antibody, or functional fragments thereof. In an additional embodiment, the extracellular domain of the first polypeptide sequence or the second polypeptide sequence comprises a single chain antibody, or a functional fragment thereof. In a further embodiment, both the first and the second polypeptide is a CIR or a functional fragment thereof. In certain embodiments, both CIR polypeptides contain an extracellular binding domain of a surface membrane polypeptide. In another embodiment, the extracellular domains of the first and second polypeptide sequences comprise the alpha and beta chains of an antibody, or a functional fragment thereof.

In an additional embodiment, the extracellular domains of the first and polypeptide sequences comprise the gamma and beta chains of a TCR, or a functional fragment thereof.

A further embodiment of the instant invention provides a method for expressing in a subject at least two polypeptides encoding at least one identical polypeptide sequence of greater than 15 amino acids in length and wherein the nucleic acid sequences encoding the two polypeptides are contained on a single viral vector comprising introducing the viral vector of the invention into a host cell; and exposing the subject to virions of the host cell media, thereby expressing the polypeptides in the subject.

In one embodiment, the method further comprises selecting for a host cell that produces virions comprising the viral vector in the host cell media.

In certain embodiments, the at least two polypeptides are multi-chimeric immune receptor (CIR) polypeptides.

In another embodiment, the instant invention features a method for expressing in a subject at least two polypeptides encoding at least one identical polypeptide sequence of greater than 15 amino acids in length, wherein the nucleic acid sequences encoding the at least two polypeptides are contained on a single viral vector comprising introducing the viral vector of the invention into a host cell; and exposing the subject to the host cell, thereby expressing the polypeptides in the subject.

In certain embodiments, the host cell is an immune cell. In a related embodiment, the immune cell is a T cell. In another embodiment, the immune cell is a human immune cell.

In a further embodiment, the step of introducing the viral vector of the invention into an immune cell occurs ex vivo. In another embodiment, the step of introducing the viral vector of the invention into an immune cell occurs in vivo.

In certain embodiments, the subject is a mammal. In one embodiment, the mammal is a human.

In another embodiment, the virions are retrovirus virions. In a related embodiment, the retrovirus is a recombinant retrovirus selected from the group consisting of avian sarcoma-leukosis virus (ASLV), murine leukemia virus (MLV), human-, simian-, feline-, and bovine immunodeficiency viruses (HIV, SIV, FIV, BIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV), AKR (endogenous) murine leukemia virus, Avian carcinoma, Mill Hill virus 2, Avian leukosis virus—RSA, Avian myeloblastosis virus, Avian myelocytomatosis virus 29, Bovine syncytial virus, Caprine arthritis encephalitis virus, Chick syncytial virus, Equine infectious anemia virus, Feline leukemia virus, Feline syncytial virus, Finkel-Biskis-Jinkins murine sarcoma virus, Friend murine leukemia virus, Fujinami sarcoma virus, Gardner-Arnstein feline sarcoma virus, Gibbon ape leukemia virus, Guinea pig type C oncovirus, Hardy-Auckerman feline sarcoma virus, Harvey murine sarcoma virus, Human foamy virus, Human spumavirus, Human T-lymphotropic virus 1, Human T-lymphotropic virus 2, Jaagsiekte virus, Kirsten murine sarcoma virus, Langur virus, Mason-Pfizer monkey vikrus, Mouse mammary tumor virus, Ovine pulmonary adenocarcinoma virus, Porcine type C oncovirus, Reticuloendotheliosis virus, Rous sarcoma virus, Simian foamy virus, Simian sarcoma virus, Simian T-lymphotropic virus, Simian type D virus 1, Snyder-Theilen feline sarcoma virus, Squirrel monkey retrovirus, Trager duck spleen necrosis virus, UR2 sarcoma virus, Viper retrovirus, Visna/maedi virus, Woolly monkey sarcoma virus, and Y73 sarcoma virus. In one embodiment, the retrovirus is an MFG-based recombinant retrovirus. In an additional embodiment, the retrovirus is a lentivirus selected from the group consisting of HIV-1, HIV-2, FIV, and SIV.

A further aspect of the invention provides a pharmaceutical composition comprising a recombinant retrovirus that contains a first nucleic acid sequence encoding a first CIR polypeptide and a second nucleic acid sequence encoding a second CIR polypeptide, wherein the first CIR polypeptide and the second CIR polypeptide comprise at least one identical polypeptide sequence of greater than 15 amino acids in length and wherein the first nucleic acid sequence and the second nucleic acid sequence contain at least one non-identical codon within the codons encoding the at least one identical polypeptide sequence of the first and second nucleic acid sequences, and a pharmaceutically acceptable carrier.

Another embodiment of the instant invention provides a kit comprising a virus comprising the viral vector of the invention, and instructions for use.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the nucleotide (SEQ ID NO: 1) and amino acid (SEQ ID NO: 2) sequences of partial human CD3ζ that are mutated at the nucleotide level as described infra. The nucleotide sequence from nucleotides 10-420 encodes the polypeptide sequence of a partial CD3ζ extracellular domain and the entire transmembrane and cytoplasmic domains of CD3ζ. This encoded polypeptide sequence is 100% identical to the corresponding polypeptide sequence contained within the human CD3ζ polypeptide sequence of GenBank ID X55510.1.

FIG. 2 displays an alignment of nucleotide sequences of partial human CD3ζ (GenBank ID X55510.1; SEQ ID NO: 3) with mutated CD3ζ (SEQ ID NO: 1). The overall homomogy between these two sequences is 60.4%. Identical amino acid residues are denoted with an asterisk (*).

FIG. 3 shows the nucleotide (SEQ ID NO: 4) and amino acid (SEQ ID NO: 5) sequences of a fusion polypeptide construct comprising partial human CD28 and CD3ζ sequences that are altered at the nucleotide level (mutated chimeric CD28CD3ζ). Nucleotides 7-330 encode a polypeptide sequence comprising a partial CD28 extracelluar domain and the entire transmembrane and cytoplasmic domain of CD28. The polypeptide sequence encoded by nucleotides 7-330 is 100% identical to the corresponding polypeptide sequence contained within the human CD28 polypeptide sequence of GenBank ID J02988.1. Nucleotides 331-666 encode a polypeptide sequence comprising the entire cytoplasmic domain of CD3ζ that is 100% identical to the corresponding polypeptide sequence contained within the human CD3ζ polypeptide sequence of GenBank ID X55510.1. The first six nucleotides (cctagg), which comprise a cleavage site of restriction enzyme AvrII and encode two the two amino acid residues P and R, respectively, are included for subcloning utility.

FIG. 4 shows an alignment of nucleotide sequences of chimeric CD28CD3ζ (SEQ ID NO: 6) with mutated chimeric CD28CD3ζ (SEQ ID NO: 4). The corresponding nucleotide sequences encoding partial CD28 and CD3ζ are from native human CD28 (GenBank ID J02988.1) and CD3Zeta (GenBank ID X55510.1). The overall homology between these two sequences is 61.3%.

FIG. 5 shows the nucleotide (SEQ ID NO: 7) and amino acid (SEQ ID NO: 8) sequences of a mutated gene that encodes a partial extracellular domain and the entire transmembrane and cytoplasmic domains of human FcεRIγ. The amino acid sequence encoded by the mutated partial FcεRIγ gene is 100% identical to the corresponding polypeptide sequence within human FcεRIγ of GenBank ID M33195.1.

FIG. 6 displays an alignment of nucleotide sequences of partial human FCεRIγ (SEQ ID NO: 9; GenBank ID M33195.1) with the mutated FCεRIγ polypeptide (SEQ ID NO: 7). The overall homomogy between these two sequences is 59.1%. Identical amino acid residues are denoted with an asterisk (*).

FIG. 12 shows the nucleotide sequence encoding Tctv_p36A_Z (SEQ ID NO: 10). The sequence of CD3ζ (TMD and cytoplasmic) is underlined. An internal BamHI (GGATCC) cloning site located in the CD3ζ seq. is bolded, and the TAA stop codon is also bolded. The location of anti-p36 TCRα sequence within the CIR sequence is indicated.

FIG. 13 displays the nucleotide sequence (SEQ ID NO: 11) also from FIG. 12, along with the encoded amino acid (SEQ ID NO: 12) sequence of Tctv_p36A_Z. A BamHI site (GGATCC) is underlined; the 28 amino acid TMD of CD3ζ is underlined and italicized; and the TMD and cytoplasmic domains of CD3ζ are italicized. The location of anti-p36 TCRα sequence within the CIR sequence is indicated.

FIG. 14 displays the nucleotide sequence encoding Tctv_p36B_Z (SEQ ID NO: 13). The location of anti-p36 TCRβ sequence within the CIR sequence is indicated.

FIG. 15 displays the nucleotide sequence (SEQ ID NO: 14) from FIG. 14, along with the amino acid (SEQ ID NO: 15) sequences of Tctv_p36B_Z. The BamHI site (GGATCC) is underlined; the 28 residue amino acid sequence of the transmembrane domain (TMD) of CD3ζ is bolded and italicized; and the TMD and cytoplasmic domain of CD3ζ is italicized. The location of anti-p36 TCRβ sequence within the CIR sequence is indicated.

FIG. 16 shows the nucleotide sequence encoding Tctv_p36b_muZ (SEQ ID NO: 16). The mutated nucleotide sequence comprising degenerate codons and encoding the transmembrane domain (TMD) and cytoplasmic domain of human CD3ζ is in bold and italicized. The location of anti-p36 TCRβ sequence within the CIR sequence is indicated.

FIG. 17 displays the nucleotide sequence encoding Tcsv_p36A_28 Z (SEQ ID NO: 17). Sequence encoding the extracellular domain and transmembrane domain (TMD) of CD28 and cytoplasmic domain of CD28 and CD3ζ are in bold and italicized. An AvrII site (CCTAAG) immediately prior to the 5' end of the CD28CD3ζ sequence is underlined; and the stop codon (TAA) is also underlined. The location of anti-p36 TCRα sequence within the CIR sequence is indicated.

FIG. 18 shows the nucleotide (SEQ ID NO: 18) and amino acid (SEQ ID NO: 19) sequences of Tctv_p36A_28 Z. The cloning site of AvrII (cctagg, encoding "PR") immediately upstream of CD28CD3ζ is bolded; the 29 residue amino acid sequence of the TMD of CD28 is bolded and underlined; and the amino acid sequence of the cytoplasmic domain of CD3ζ is italicized. The location of anti-p36 TCRα sequence within the CIR sequence is indicated.

FIG. 19 shows the nucleotide sequence of Tctsv_p36B_mu28Z (SEQ ID NO: 20). The mutated nucleotide sequence, which comprises degenerated codons and encodes the TMD and cytoplasmic domain of human CD28 and the cytoplasmic domain of CD3ζ, is italicized. The location of anti-p36 TCRβ sequence within the CIR sequence is indicated.

FIG. 20 shows the nucleotide sequence encoding hu_CD4SigalpepECD (SEQ ID NO: 21). This sequence comprises the signal peptide and extracellular domain of human CD4.

FIG. 21 shows the nucleotide sequence encoding Mu_hu_CD4SigalpepECD (SEQ ID NO: 22). This sequence comprises mutated signal peptide and the extracellular domain of human CD4.

FIG. 22 displays an alignment of the nucleotide sequences CD4_SignalpepECD (SEQ ID NO: 21) and Mu_CD4_SignalECD (SEQ ID NO: 22). Both DNA sequences encode an identical polypeptide sequence comprising the signal peptide and extracellular domain of native human CD4.

FIG. 23 shows the nucleotide sequence encoding CD4_SignalpepECD_Z (SEQ ID NO: 23). The original cDNA encoding signal peptide and ECD of human CD4 is linked to the 5'end of an original cDNA encoding the native human CD3ζ TMD and cytoplasmic domains. The cDNA encoding the CD3ζ is italicized.

FIG. 24 shows the nucleotide sequence encoding Mu_CD4_SignalpepECD_28 (SEQ ID NO: 24). The mutated nucleotide sequence (replaced with degenerate codons) encoding signal peptide and ECD of human CD4 is italicized. This sequence is linked to the 5'end of an original cDNA encoding the TMD and cytoplasmic domain of native human CD28.

FIG. 25 displays exemplary structures of CIRs designed to target JC virus and HIV. "Tctv" denotes two-chain two-vector, while "Tcsv" denotes two-chain single-vector.

FIG. 26 displays nucleotide sequences of the eight overlapping oligonucleotide DNA primers that were used in PCR to generate a DNA fragment encoding mutated partial ECD, TMD and cytoplasmic domains of human CD3ζ (Z).

Figure 33:
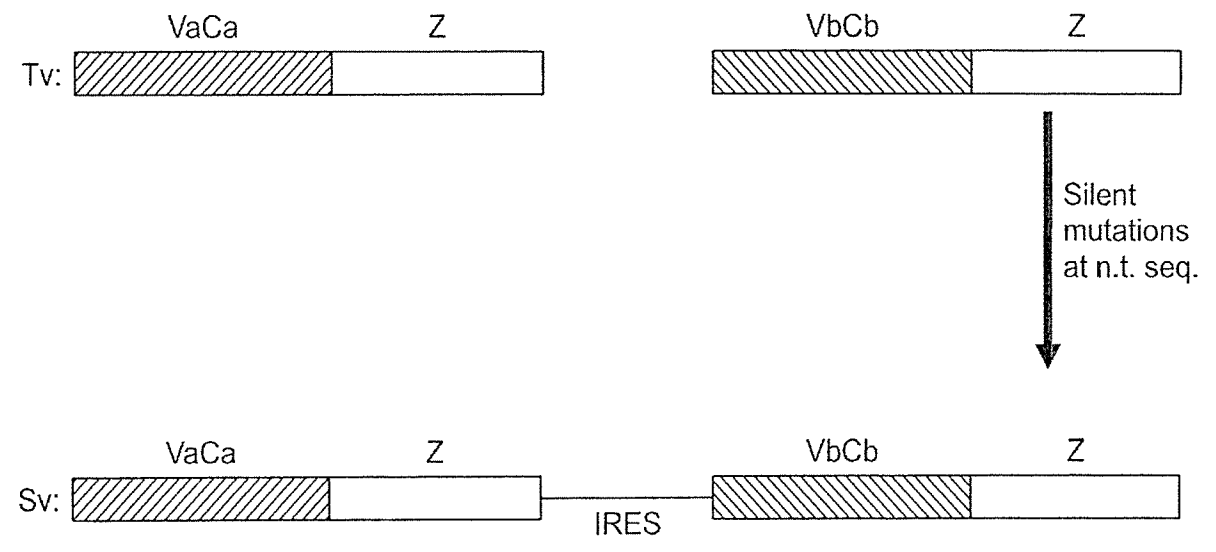

FIG. 33 depicts a schematic diagram that illustrates and compares two vector (Tctv) and single vector (Tcsv) approaches to CIR synthesis.

FIG. 34 shows cell sorting results for no vector (nv), two chain two vector (Tctv), and two chain single vector (Tcsv) CIRs of TCR α and TCR β chains, which demonstrate that the Tcsv approach (involving mutation of the nucleic acid sequence encoding a cytoplasmic (z) chain with degenerate codon usage) efficiently yields "designer T cells" that robustly express both TCR α and TCR β chains.

FIG. 36 is a schematic of two chain two vector (TcTv) CIRs and the results showing transduction of cells with two separate vectors.

FIG. 37 is a schematic of a two chain single vector (TcSv) CIR and the results showing transduction of cells with the vector.

FIG. 38 is a schematic of engineering degenerate nucleotides in repeated sequence to prevent homologous recombination and deletion.

FIG. 40 is a schematic of TcSv anti-JCV constructs.

FIG. 41 is a schematic and tetramer staining results of the potential for homologous recombination and deletion of sequences in a TcSv anti-JVC construct.

FIG. 42 shows degenerate codon TcSv anti-JCV TCR constructs for wtCD3z (SEQ ID NO: 35) and dCD3z (SEQ ID NO: 36).

Figure 7:
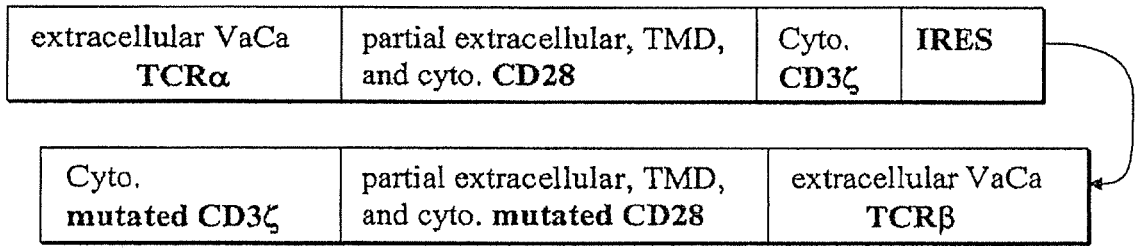
FIG. 7 depicts a schematic diagram of a viral vector comprising sequences encoding two chimeric immune receptor (CIR) polypeptides linked by an IRES sequence. Sequence encoding the first polypeptide comprises native sequences encoding the extracellular VaCa domain of TCRα, fused to the partial extracellular domain, TMD and cytoplasmic domain of CD28, which is fused to cytoplasmic CD3ζ sequence. Sequence encoding the second polypeptide comprises sequence that encodes the TCRβ extracellular sequence fused to mutated sequence (modified with degenerate codons) encoding the partial extracellular domain, TMD and cytoplasmic domain of CD28 which is fused to mutated sequence encoding the cytoplasmic CD3ζ sequence.
Figure 8:
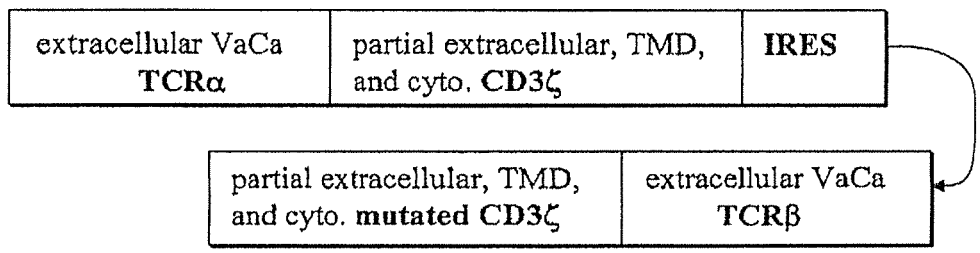
FIG. 8 displays a schematic diagram of a viral vector comprising sequences encoding two chimeric immune receptor (CIR) polypeptides linked by an IRES sequence. Sequence encoding the first polypeptide comprises native sequences encoding the extracellular VaCa domain of TCRα, fused to the partial extracellular domain, TMD and cytoplasmic domain of CD3ζ. Sequence encoding the second polypeptide comprises sequence that encodes the TCRβ extracellular sequence fused to mutated sequence (modified with degenerate codons) encoding the partial extracellular domain, TMD and cytoplasmic domain of CD3ζ.
Figure 9:
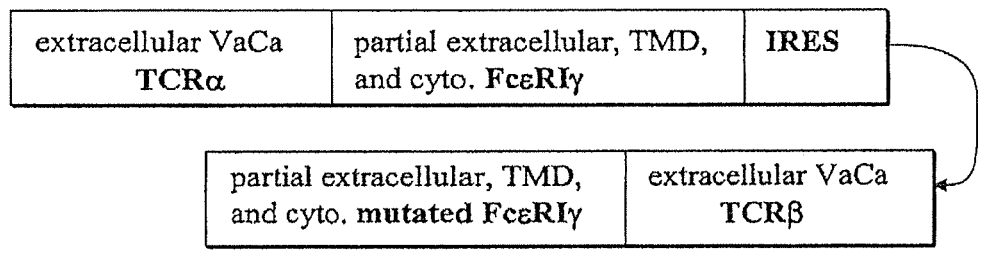
FIG. 9 displays a schematic diagram of a viral vector comprising sequences encoding two chimeric immune receptor (CIR) polypeptides linked by an IRES sequence. Sequence encoding the first polypeptide comprises native sequences encoding the extracellular VaCa domain of TCRα, fused to the partial extracellular domain, TMD and cytoplasmic domain of FcεRIγ. Sequence encoding the second polypeptide comprises sequence that encodes the TCRβ extracellular sequence fused to mutated sequence (modified with degenerate codons) encoding the partial extracellular domain, TMD and cytoplasmic domain of FcεRIγ.
Figure 10:
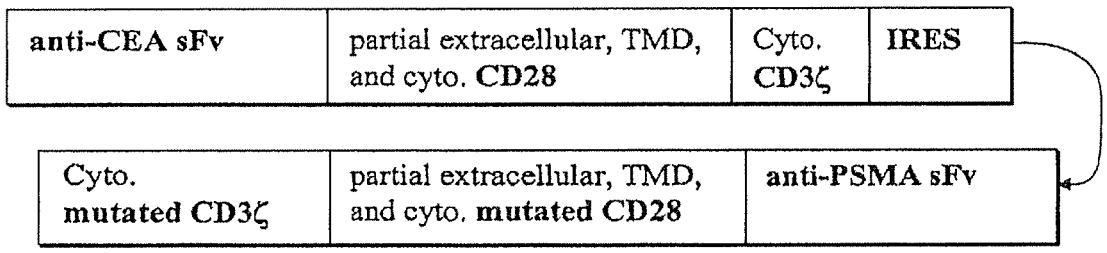
FIG. 10 depicts a schematic diagram of a viral vector comprising sequences encoding two chimeric immune receptor (CIR) polypeptides linked by an IRES sequence. Sequence encoding the first polypeptide comprises native sequences encoding anti-CEA sFv, fused to the partial extracellular domain, TMD and cytoplasmic domain of CD28, which is fused to cytoplasmic CD3ζ sequence. Sequence encoding the second polypeptide comprises sequence that encodes anti-PMSA sFv fused to mutated sequence (modified with degenerate codons) encoding the partial extracellular domain, TMD and cytoplasmic domain of CD28, which is fused to mutated sequence encoding the cytoplasmic CD3ζ sequence.

DETAILED DESCRIPTION OF THE INVENTION

The present invention relates, at least in part, to vectors, e.g., viral vectors, that comprise highly homologous polypeptides (e.g., chimeric immune receptors (CIRs)) yet reduce the likelihood of homologous recombination events between the nucleic acid sequences that encode such highly homologous polypeptides via directed alteration (mutation) of the underlying nucleic acid sequences that encode the highly homologous polypeptides. Directed alteration (mutation) of such nucleic acid sequences employs degenerate codons, which allow for nucleotide homology between two nucleic acid sequences that encode highly homologous polypeptides or even the same polypeptide (e.g., an identical polypeptide domain within two CIRs contained within the same viral vector) to be significantly reduced.

The invention, at least in part, additionally provides methods of design and synthesis of such vectors, including, in certain embodiments, design and synthesis of viral vectors that comprise two or more nucleic acid sequences that encode CIRs possessing at least one polypeptide sequence domain that is highly homologous and/or identical (e.g., a polypeptide domain comprising a span of 15 amino acid residues or greater that is identical and present in each of the two or more CIR polypeptide sequences.).

The instant invention, at least in part, also relates to therapeutic applications of the vectors, e.g., viral vectors described infra. Exemplary therapeutic applications include:

modification of immune cells (e.g., lymphocytes, such as T cells and NK cells) and/or stem cells via introduction of CIRs through retroviral transduction or DNA and/or RNA transfection, useful for immunotherapy of cancers, infectious diseases (e.g., PML, HIV/AIDS) and autoimmune diseases (e.g., CIRs may be used to target autoreactive immune cells);

correction of genetic defects via introduction of correct or missing genes to stem cells and/or tissues or organs of target patients and/or individuals; and introduction of multiple suicide genes via retroviral transduction or DNA and/or RNA transfection locally or systematically for treatment of cancer and/or autoimmune diseases or disorders.

So that the invention may be more readily understood, certain terms are first defined.

Definitions

Unless further defined below, all terms as used herein are given their customary meaning. In the case of terms specifically defined below, the definitions include their customary meaning but are expanded to include the additional context of the specific definition.

As used herein, the term "vector" refers to a nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Accordingly, the term "viral vector," as used herein, refers to a vector that can be passaged in a virus, that can be used to transduce, transform or infect a cell, thereby causing the cell to express nucleic acids and/or proteins other than those native to the cell.

As used herein, the term "chimeric immune receptor" or "CIR" refers to tumor- or virus-specific ligand molecules and/or antibody molecules that are fused to the signaling domains of either the T cell receptor (TCR) or the Fc receptor. T cells expressing such receptors recapitulate the cytopathic effects mediated by the T cell receptor and allow for the targeting of tumor or virus-infected cells in an MHC-independent manner. Exemplary CIRs of the invention comprise extracellular domains that bind to target antigens, e.g., infectious disease or tumor antigens, a transmembrane domain (TMD), and a cytoplasmic domain of CD28 and/or CD3ζ. The use of CIRs can allow for production of large numbers of T cells possessing redirected target specificity, including possession of heightened sensitivity and/or response to a target antigen when bound.

The term "T helper (Th) cells" as used herein, refers to a functional subclass of T cells which help to generate cytotoxic T cells and which cooperate with B cells to stimulate antibody production. Helper T cells recognize antigen in association with class II MHC molecules and provide contact dependent and contact independent (cytokine) signals to effector cells.

A protein "domain" is a relatively small (i.e., between about 10 and 200 amino acids) globular unit that is part of a protein. A protein can comprise two or more domains that are linked by relatively flexible stretches of amino acids. In addition to having a semi-independent structure, a given domain can be largely or wholly responsible for carrying out functions that are normally carried out by the intact protein. In addition to domains that have been determined by in vitro manipulations of protein molecules, it is understood in the art that a "domain" may also have been identified in silico, i.e, by software designed to analyze the amino acid sequences encoded by a nucleic acid in order to predict the limits of domains. The latter type of domain is more accurately called a "predicted" or "putative" domain but, in the present disclosure, the term domain encompasses both known and predicted domains unless stated otherwise. Examples of CIR polypeptide domains include, but are not limited to, the extracellular, transmembrane and cytoplasmic domains, which may be readily predicted in silico using art-recognized hydropathy analyses that are especially effective in identification of transmembrane domains (TMDs) of proteins.

The terms "variant", "homologue" or "fragment" in relation to the nucleotide sequence coding for the homologous polypeptides, e.g., CIR polypeptides, of the present invention include any substitution of, variation of, modification of, replacement of, deletion of or addition of one or more nucleic acid from or to the sequence providing the resultant nucleotide sequence codes for or is capable of coding for a polypeptide. In particular, the term "homologue" covers homology with respect to structure and/or function providing the resultant nucleotide sequence codes for or is capable of coding for a polypeptide, e.g., CIR polypeptide. With respect to sequence homology, preferably there is less than 99%, more preferably less than 98%, more preferably less than 95%, more preferably less than 85%, more preferably less than 75% homology between nucleic acid sequences of the vector construct (e.g., retroviral vector construct) encoding for homologous polypeptides of the invention. More preferably, there is less than 70% homology, more preferably less than 69%, 68%, 67%, 66%, 65%, 64%, 63%, 62%, 61%, 60%, 59%, 58%, 57%, 56%, 55%, 54%, 53%, 52% or 51% homology between two nucleic acid sequences that encode homologous polypeptide sequences of the constructs of the present invention.

In particular, the term "homology" as used herein may be equated with the term "identity". Relative sequence homology (i.e. sequence identity) can be determined by commercially available computer programs that can calculate % homology between two or more sequences. A typical example of such a computer program is CLUSTAL.

Homology of polypeptide or nucleic acid sequences may be assessed globally (e.g., across the entire expanse of aligned polypeptide sequences) or locally (e.g., via inspection of a domain or subdomain of aligned polypeptide sequences). Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=(# of identical positions/total # of positions)×100), optionally penalizing the score for the number of gaps introduced and/or length of gaps introduced.

The comparison of sequences and determination of percent identity between two sequences can be accomplished using a mathematical algorithm. In one embodiment, the alignment is generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87: 2264-68, modified as in Karlin and Altschul (1993) Proc. Natl. Acad. Sci. USA 90: 5873-77. Such an algorithm is incorporated into the BLAST programs (version 2.0) of Altschul et al. (1990) J. Mol. Biol. 215: 403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17): 3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The NCBI Basic Local Alignment Search Tool (BLAST) (Altschul et al. 1990 J. Mol. Biol. 215: 403-10) is available from several sources, including the National Center for Biotechnology Information (NCBI, Bethesda, Md.) and on the Internet, for use in connection with the sequence analysis programs blastp, blastn, blastx, tblastn and tblastx. It can be accessed on the internet via the National Library of Medicine (NLM)'s world-wide-web URL at ncbi(dot)nlm(dot)nih(dot)gov. A description of how to determine sequence identity using this program is available at the NLM's website on BLAST tutorial.

For comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 90%, 95%, 98%, or 99% sequence identity. When less than the entire sequence is being compared for sequence identity, homologs will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the "Frequently Asked questions" section of the NCBI's web-resource on BLAST.

Alternatively, one may manually align the sequences and count the number of identical amino acids in the original sequence and a reference sequence that is compared to the original sequence. This number of identical amino acids is divided by the total number of amino acids in the reference sequence and multiplied by 100 to result in the percent identity.

One of ordinary skill in the art will appreciate that these sequence identity ranges are provided for guidance only; it is entirely possible that strongly significant homologs could be obtained that fall outside of the ranges provided.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "retrovirus," as used herein, refers to any virus belonging to the family Retroviridae. Retroviruses are enveloped viruses that possess an RNA genome and replicate via a DNA intermediate. Retroviruses rely on the enzyme reverse transcriptase to perform reverse transcription of the retroviral genome from RNA into DNA, which can then be integrated into a host cell genome using the integrase enzyme.

Lentiviruses are characterized by long incubation periods between infection of the host and the manifestation of clinical disease. Lentiviruses infect a wide variety of mammals, including humans, monkeys, sheep, goats, and horses. Lentiviruses include, for example, immunodeficiency retroviruses, such as HIV-1, HIV-2, FIV, and SIV.

A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

The term "supernatant," as used herein, refers to the culture medium in which a cell is grown. The culture medium includes material from the cell, including, e.g., viral particles, e.g., retroviral particles which bud off from the cell membrane and enter the culture medium.

A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, calcium-DNA precipitates, and particle gun acceleration.

A "transfer" vector or "transducing" vector, as used herein, refers to a vector which shuttles a transgene.

A "transformed" cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

The term "transgene," as used herein, refers to an exogenous gene supplied by a vector. Examples of such genes include CIRs, single chain antibodies, and any other genes introduced via vector.

The term "transgenic cell," as used herein, refers to transformed cells which contain foreign, non-native DNA.

As used herein, the term "subject" includes a human or nonhuman mammal.

The production of proteins can be accomplished in a variety of ways. DNA sequences which encode for the protein, or a fragment or variant of the protein, can be engineered such that they allow the protein to be expressed in eukaryotic cells, bacteria, insects, and/or plants. In order to accomplish this expression, the DNA sequence can be altered and operably linked to other regulatory sequences. The final product, which contains the regulatory sequences and the therapeutic protein, is referred to as a vector. This vector can then be introduced into the eukaryotic cells, bacteria, insect, and/or plant. Once inside the cell the vector allows the protein to be produced.

One of ordinary skill in the art will appreciate that the DNA can be altered in numerous ways without affecting the biological activity of the encoded protein. For example, PCR may be used to produce variations in the DNA sequence which encodes a CIR. Such variants may be variants that are optimized for codon preference in a host cell that is to be used to express the protein, other sequence changes that facilitate expression, or sequences as described herein that are made non-identical at the nucleic acid level in order to reduce homologous recombination events.

At least two types of cDNA sequence variants may be produced. In one type, the variation in the cDNA sequence is not manifested as a change in the amino acid sequence of the encoded polypeptide. These silent variations are simply a reflection of the degeneracy of the genetic code, and are a preferred form of variation for practice of the methods of the present invention. In the second type, the cDNA sequence variation does result in a change in the amino acid sequence of the encoded protein. In such cases, the variant cDNA sequence produces a variant polypeptide sequence. In order to optimize preservation of the functional and immunologic identity of the encoded polypeptide, any such amino acid substitutions may be conservative. Conservative substitutions replace one amino acid with another amino acid that is similar in size, hydrophobicity, etc. Such substitutions generally are conservative when it is desired to finely modulate the characteristics of the protein. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gin; Asp for Glu; Pro for Gly; Asn or Gin for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and lie or Leu for Val.

Variations in the cDNA sequence that result in amino acid changes, whether conservative or not, are minimized to enhance preservation of the functional and immunologic identity of the encoded protein. In particular embodiments, any cDNA sequence variant will introduce no more than 20, for example fewer than 10 amino acid substitutions into the encoded polypeptide. Variant amino acid sequences can, for example, be greater than 75%, greater than 80%, greater than 90% or even greater than 95%, greater than 96%, greater than 97%, greater than 98%, or greater than 99% identical (though not perfectly identical at the level of amino acid sequence to be considered a variant amino acid sequence) to the original (e.g., native) amino acid sequence.

Conserved residues in the same or similar nucleic acids or proteins from different species can provide guidance about possible locations for making substitutions in the nucleic acid or amino acid sequence. A residue which is highly conserved across several species is more likely to be important to the function of the nucleic acid or protein than a residue that is less conserved across several species.

By "reduce" or "inhibit" is meant the ability to cause an overall decrease preferably of 10% or greater, 20% or greater, 50% or greater, 75% or greater, 85% or greater, 90% or greater, 95% or greater, 96% or greater, 97% or greater, 98% or greater, or 99% or greater in the level of an assessed effect (e.g., homologous recombination between nucleic acid sequences, cancer cell and/or tumor proliferation, etc.) for a vector, cell, sample, tumor, etc. that has been altered from a native state (e.g., mutated in nucleic acid sequence) and/or contacted with an agent or otherwise employed in creating a composition of the invention or utilizing a method of the invention, as compared to an appropriate vector, control cell, sample, tumor, etc. (e.g., a vector comprising nucleic acid sequences that have not been mutated to decrease homology while retaining homology of the encoded polypeptides, a cell that has not been contacted with an agent or employed in a method of the invention, etc.). In certain aspects of the instant invention, especially those related to reduction of homologous recombination events between nucleic acid sequences that encode homologous polypeptide sequences, as well as those aspects of the invention related, e.g., to reduction of binding affinities of an antigen binding fragment, "reduce" or "inhibit" can refer to a decrease in the rate of occurrence of such events (and/or decrease in binding affinity) that is logarithmic in scale, e.g., 10-fold or greater, 100-fold or greater, 1000-fold or greater, 10,000-fold or greater, 100,000-fold or greater, or a million-fold or greater.

The term "cancer" or "neoplasia" refers in general to any malignant neoplasm or spontaneous growth or proliferation of cells. The term as used herein encompasses both fully developed malignant neoplasms, as well as premalignant lesions. A subject having "cancer", for example, may have a tumor or a white blood cell proliferation such as leukemia. In certain embodiments, a subject having cancer is a subject having a tumor, such as a solid tumor.

The term "solid tumor" refers to a carcinoma, sarcoma, adenorna, cancers of neuronal origin or, in fact, to any type of cancer which does not originate from the hematopoietic cells. Cancers involving a solid tumor include but are not limited to brain cancer, glioma, astrocytoma, medulloblastoma, craniopharyngioma, ependymoma, pinealoma, retinoblastoma, carcinoma, sarcoma, adenoma, hepatocellular cancer, hepatoblastoma, rhabdomyosarcoma, gastric cancer, stomach cancer, esophageal cancer, thyroid cancer, ganglioblastoma, fibrosarcoma, myxosarcoma, liposarcoma, chondrosarcoma, osteogenic sarcoma, chordoma, angiosarcoma, endotheliosarcoma, lymphangiosarcoma, synovioma, Ewing's tumor, leiomyosarcoma, rhabdotheliosarcoma, colon cancer, pancreatic cancer, breast cancer, ovarian cancer, uterine cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, skin cancer, cervical cancer, testicular cancer, lung cancer, small cell lung cancer (SCLC), non small cell lung cancer (NSCLC), colorectal cancer (CRC), bladder cancer, epithelial cancer, multiple myeloma, rectal cancer, thyroid cancer, head and neck cancer, cancer of the peripheral nervous system, cancer of the central nervous system, neuroblastoma, cancer of the endometrium, as well as metastasis of all the above.

As used herein, the term "tumor" refers to a proliferation of cells (e.g., a neoplasia, a growth, a polyp) resulting from neoplastic growth and is most typically a malignant tumor. In the case of a neoplastic transformation, a neoplasia is malignant or is predisposed to become malignant. Malignant tumors are typically characterized as being anaplastic (primitive cellular growth characterized by a lack of differentiation), invasive (moves into and destroys surrounding tissues) and/or metastatic (spreads to other parts of the body).

Various methodologies of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing a vector synthesis and/or treatment methodology, as described herein. For example, a homologous recombination rate, a transcription rate, mRNA level, translation rate, protein level, biological activity, cellular characteristic or property, genotype, phenotype, etc. can be determined for an unmodified vector and compared with the recombination rate, transcription rate, etc., of a vector modified in the manner described herein. Such comparisons can be performed for methods and/or therapies performed in vitro or in vivo. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Additional definitions of terms commonly used in molecular genetics can be found in Benjamin Lewin, *Genes V*, published by Oxford University Press, 1994 (ISBN 0-19-854287-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Various aspects of the invention are described in further detail in the following subsections.

Certain aspects of the instant invention provide viral vectors comprising two or more homologous polypeptides (e.g., CIR polypeptides) and/or polypeptide domains that are used in the treatment of a disease and/or disorder. In certain embodiments, homologous polypeptide-expressing (e.g., CIR-expressing) viral vectors of the instant invention are employed in gene therapy and immunotherapy approaches. For example, the compositions and methods of the invention can be used to treat cancer in a subject (e.g., a human subject), through use of T cells that express antigen-specific CIRs. In such embodiments, the extracellular domains of homologous polypeptides (e.g., CIR polypeptides) are designed to bind specifically to a tumor and/or cancer cell antigen(s), thereby inducing activation of the CIR-presenting T cell ("designer T cell") upon binding of the T cell to the tumor and/or cancer cell antigen, in turn inducing a specific immune response to cancer and/or tumor antigen-presenting cells. Accordingly, the polypeptide-expressing (e.g., CIR-expressing) viral vector(s) of the instant invention can be designed to bind to any art-recognized cancer-specific and/or tumor-specific antigen (e.g., via synthesis of CIR molecules comprising extracellular tumor antigen-binding fragment(s), e.g., extracellular sFv polypeptides, alpha and/or beta chain antibody polypeptides, etc.). Such cancer and/or tumor antigens include, but are not limited to, e.g., cyclin-dependent kinase-4, □-catenin, Caspase-8, MAGE-1, MAGE-3, Tyrosinase, Surface Ig idiogype, Her-2/neu, MUC-1, HPV E6, HPV E7, CD5, idiotype, CAMPATH-1, CD20, CEA, mucin-1, Lewis$^x$, CA-125, EGFR, p185$^{HER2}$, IL-2R, FAP-□, Tenascin, metalloproteinases, phCG, gp100 or Pmell7, HER2/neu, CEA, gp100, MART1, TRP-2, melan-A, NY-ESO-1, MN (gp250), idiotype, MAGE-1, MAGE-3, Tyrosinase, Telomerase, MUC-1 antigens, and germ cell-derived tumor antigens, the blood group antigens, for example, Lea, Leb, LeX, LeY, H-2, B-1, B-2 antigens. In certain embodiments, more than one cancer and/or tumor antigens can be bound by the same CIR-expressing T cell; for example, binding of one CIR of a T cell to a MAGE antigen can be combined with binding of another CIR of the T cell to another antigen, such as melanin A, tyrosinase, or gp100. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor-associated antigens within the meaning of the present invention. Still other exemplary tumor-associated antigens comprise, but are not limited to, MAGE-1, MAGE-3, MUC-1, HPV 16, HPV E6 & E7, TAG-72, CEA, L6-Antigen, CD19, CD22, CD37, CD52, HLA-DR, EGF Receptor and HER2 Receptor. In many cases immunoreactive antibodies (and/or immunoreactive antigen-binding fragments) for each of these antigens have been reported in the literature.

The viral vectors of the invention can also be used as immunotherapeutics in treatment of infectious disease; for example, in procedures that employ CIRs that recognize infectious disease antigens. Accordingly, homologous polypeptides (e.g., CIR polypeptides) of the invention can be made that bind to any of a number of forms of infectious disease antigen, thereby inducing an immune response to the infectious disease antigen upon binding. Infectious disease antigens to which homologous polypeptides (e.g., CIR polypeptides) of the instant invention can be designed to bind include, but are not limited to, bacterial antigens, viral antigens, fungal antigens, parasitic antigens, and microbial toxins. Exemplary forms of each class of antigen are considered in greater detail below.

Bacteria

Examples of bacteria (specifically, epitopes thereof) to which homologous polypeptides (e.g., CIR polypeptides) of the instant invention may bind include, but are not limited to: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacterfreundii, Salmonella enterica Typhimurium, Salmonella enterica Typhi, Salmonella enterica Paratyphi, Salmonella enterica Enteridtidis, Shigella dysenteriae, Shigellaflexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacterfetus, Campylobacterjejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis,* and *Staphylococcus saccharolyticus*. In a particular embodiment, a construct of the invention comprises a binding molecule which binds to Staphylococcal protein A.

Viruses

Examples of viruses (or epitopes thereof) which may be bound by homologous polypeptides (e.g., CIR polypeptides) of the instant invention include, but are not limited to: polyomavirus JC (JCV), human immunodeficiency virus type I (HIV I), hepatitis B virus (HBV), hepatitis C virus (HCV), cytomegalovirus (CMV), Epstein Barr virus (EBV), influenza virus hemagglutinin (Genbank accession no. J02132; Air, 1981, Proc. Natl. Acad. Sci. USA 78:7639-7643; Newton et al., 1983, Virology 128:495-501), human respiratory syncytial virus G glycoprotein (Genbank accession no. Z33429; Garcia et al., 1994, J. Virol.; Collins et al., 1984, Proc. Natl. Acad. Sci. USA 81:7683), measles virus hemagglutinin (Genbank accession no. M81899; Rota et al., 1992, Virology 188:135-142), herpes simplex virus type 2 glycoprotein gB (Genbank accession no. M14923; Bzik et al., 1986, Virology 155:322-333), poliovirus I VP1 (Emini et al., 1983, Nature 304:699), envelope glycoproteins of HIV I (Putney et al., 1986, Science 234:1392-1395), hepatitis B surface antigen (Itoh et al., 1986, Nature 308:19; Neurath et al., 1986, Vaccine 4:34), diphtheria toxin (Audibert et al., 1981, Nature 289:543), *streptococcus* 24M epitope (Beachey, 1985, Adv. Exp. Med. Biol. 185:193), gonococcal pilin (Rothbard and Schoolnik, 1985, Adv. Exp. Med. Biol. 185:247), pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulina hydodysenteriae protective antigen, bovine viral diarrhea glycoprotein 55, Newcastle disease virus hemagglutinin neuraminidase, swine flu hemagglutinin, swine flu neuraminidase, foot and mouth disease virus, hog colera virus, swine influenza virus, African swine fever virus, Mycoplasma hyopneumoniae, infectious bovine rhinotracheitis virus (e.g., infectious bovine rhinotracheitis virus glycoprotein E or glycoprotein G), or infectious laryngotracheitis virus (e.g., infectious laryngotracheitis virus glycoprotein G or glycoprotein I), a glycoprotein of La Crosse virus (Gonzales Scarano et al., 1982, Virology 120:42), neonatal calf diarrhea virus (Matsuno and Inouye, 1983, Infection and Immunity 39:155), Venezuelan equine encephalomyelitis virus (Mathews and Roehrig, 1982, J. Immunol. 129:2763), punta toro virus (Dalrymple et al., 1981, Replication of Negative Strand Viruses, Bishop and Compans (eds.), Elsevier, N.Y., p. 167), murine leukemia virus (Steeves et al., 1974, J. Virol. 14:187), mouse mammary tumor virus (Massey and Schochetman, 1981, Virology 115:20), hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651 693; Tiollais et al., 1985, Nature 317:489 495), of equine influenza virus or equine herpesvirus (e.g., equine influenza virus type A/Alaska 91 neuraminidase, equine influenza virus type A/Miami 63 neuraminidase, equine influenza virus type A/Kentucky 81 neuraminidase equine herpesvirus type 1 glycoprotein B, and equine herpesvirus type I glycoprotein D, antigen of bovine respiratory syncytial virus or bovine parainfluenza virus (e.g., bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, the bovine parainfluenza virus type 3 hemagglutinin neuraminidase), bovine viral diarrhea virus glycoprotein 48 or glycoprotein 53, hepatitis type A, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, echinovirus, arbovirus, hantavirus, coxsackie virus, mumps virus, measles virus, rubella virus, polio virus, human immunodeficiency virus type II (HIV II), any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, human herpesvirus 6, cercopithecine herpes virus I (B virus), and poxviruses.

In certain embodiments, homologous polypeptides (e.g., CIR polypeptides) of the instant invention bind to HIV, inducing an immune response to the virus in a subject to whom the viral vector is administered. Various antigenic domains (e.g., epitopes) of HIV are known in the art and such domains include structural domains such as Gag, Gag-polymerase, Gag-protease, reverse transcriptase (RT), integrase (IN) and Env. The structural domains of HIV are often further subdivided into polypeptides, for example, p55, p24, p6 (Gag); p160, p10, p15, p31, p65 (pol, prot, RT and IN); and gp160, gp120 and gp41 (Ems) or Ogp140 as constructed by Chiron Corporation. Molecular variants of such polypeptides can also be targeted for binding by the homologous polypeptides (e.g., CIR polypeptides) of the instant invention, for example, variants such as those described in PCT/US99/31245; PCT/US99/31273 and PCT/US99/31272.

Fungi

Examples of fungi (or epitopes thereof) which may be bound by homologous polypeptides (e.g., CIR polypeptides) of the instant invention include, but are not limited to fungi from the genus *Mucor, Candida*, and *Aspergillus*, e.g., *Mucor racmeosus, Candida albicans*, and *Aspergillus niger.*

Parasites

Examples of parasites (or epitopes thereof) which may be bound by homologous polypeptides (e.g., CIR polypeptides) of the instant invention include, but are not limited to: *Toxoplasma gondii, Treponema pallidun, Malaria*, and *Cryptosporidium.*

Microbial Toxins

Examples of microbial toxins (or epitopes thereof) which may be bound by homologous polypeptides (e.g., CIR polypeptides) of the instant invention include, but are not limited to: toxins produced by *Bacillus anthracis, Bacillus cereus, Bordatella pertussis, Clostridium botulinum, Clostridium perfringens, Clostridium tetani, Croynebacterium diptheriae, Salmonella* sp. *Shigella* sp., *Staphyloccus* sp., and *Vibrio cholerae*. Toxins such as ricin from jack bean and other naturally-occurring (e.g., produced by an organism) and man-made toxins or portions thereof may also be bound by the homologous polypeptides (e.g., CIR polypeptides) of the instant invention.

Chimeric Immune Receptors

Genetically modified immune function cells, such as T cells and NK cells engineered to express foreign chimeric immune receptors (CIRs) are effective immunotherapeutics for cancer and infectious diseases. Isolation of autologous antigen specific immune cells, such as T cells, for therapeutic application is a laborious task, and is not possible where such cells are absent or rare. Therefore, strategies have been developed to genetically transfer immune receptors specific to tumor or virus into patients' T cells. To this end, chimeric immune receptors (CIRs) have been constructed that join antigen (Ag)-recognition domains to signaling domains of the T-cell receptor (TCR) or Fc receptor. T cells expressing such CIRs recapitulate the immune specific responses mediated by the introduced receptor.

In a prior exemplary description of therapeutic use of CIR molecules, Severino et al. (2003 *Virology* 306: 371-75) proposed transduction of T cells with a CIR as a strategy for generation of cellular immunity against viral pathogens such as HIV-1. Specifically, for the CD4-CD3-zeta chain (CD4-zeta) CIR, specificity for HIV-1 is conferred by binding of the CD4 moiety to gp120 on the surface of infected cells. However, it is unclear whether CD4-zeta-T cells may differ from naturally-derived $CD8^+$ cytotoxic T cells (CTL) in their susceptibility to viral escape mechanisms or the ability to recognize different cell types that support viral replication.

In general, a chimeric immune receptor (CIR) consists of three portions:

1. An "extracellular domain" comprising an antigen binding or target marker binding domain, including, e.g., a variable region of antibody or functional fragment thereof, an extracellar domain of T cell receptor (TCR; e.g., Va or Vb; VaCa or VbCb) or functional fragment thereof, or an extracellular domain of CD4 (binding to HIV gp120) or functional fragment thereof;
2. A "transmembrane domain (TMD)" comprising an art-recognized, functional TMD (in certain embodiments of the present invention, the TMD of the CIR is, e.g., the CD3ζ TMD, CD28 TMD, CD8 TMD, CD4 TMD or FcεRiγ TMD, or a variant polypeptide or functional fragment thereof); and
3. An "intracellular signaling domain," comprising, e.g., the cytoplasmic portion of CD3ζ or a functional fragment thereof, FCεRIγ or a functional fragment thereof, and/or CD28 (CD28 may be used to provide co-stimulatory signaling) or a functional fragment thereof.

In certain embodiments of the instant invention, the extracellular portion of an antibody-based CIR (IgCIR) consists of a single chain Fv or a fragment thereof ("sFv" or "scFv," used interchangably herein). Similar to IgCIR, a TCRCIR is comprised of TCR variable antigen binding fragments (Vα and Vβ, or antigen binding fragments thereof) in the context of specific MHC molecules, linked to nucleic acid molecules (or functional fragments thereof) that encode signaling domains of the T-cell receptor (TCR) or Fc receptor. TCRCIR can be constructed in two basic forms: as a single chain TCRCIR (scTCRCIR), or as a two chain TCRCIR (tcTCRCIR). For a scTCRCIR, both TCR Vα and Vβ are present within the same single chain TCR protein, while in a tcTCRCIR, the Vα and Vβ are in separate chains which form heterodimers (Willemsen et al., 2000 *Gene Ther.* 7: 1369).

A number of published reports have described the fact that TCRs (alpha and beta chains) have around 100- to 1,000-fold lower binding affinities for their cognate antigens (peptide/MHC complex), as compared to antibodies directed to the same cognate antigens. In addition, it has been reported in the literature that the single chain format T cell receptors generally have greatly reduced affinities for cognate antigens, as compared to the affinities of their corresponding parental two chain forms for such antigens, with some single chain T cell receptors completely losing antigen binding affinity. Higher binding affinities of TCRs, including chimeric TCRs, have been shown to be associated with higher potency of modified T cells expressing such receptors, with regard to the function of such cells in T cell activation, including induction of proliferation, killing of target cells and induction of cytokine secretion. Several reports in the literature have indicated that single chain formats of TCRCIRs possess binding affinities that are too low to be of therapeutic or diagnostic value. Therefore, to create functional TCRCIRs with reasonably high antigen binding affinities, the two chain format for natural TCRs possesses significant advantages over a single chain format.

In certain embodiments, the instant invention provides means and compositions designed to exploit the advantages associated with two chain formats for TCRCIR delivery (as well as those advantages associated with co-delivery and/or co-expression of two or more heterologous proteins comprising one or more highly homologous domains—e.g., co-stimulation of both CD3ζ (T cell antigen receptor) and CD28-dependent signaling pathways in T cells using CIRs that possess, e.g., highly homologous (e.g., identical) extracellular domains). In specific embodiments, the instant invention overcomes problems associated with low host cell transduction efficiencies by enabling delivery of two or more nucleic acid sequences encoding for highly homologous (e.g., identical) polypeptides on a single viral vector. In such embodiments of the instant invention, methods as described in greater detail below are employed to produce viral vector sequences comprising nucleic acid sequences encoding two or more highly homologous (e.g., identical) polypeptides or polypeptide domains thereof, yet that possess reduced risk of homologous recombination between such nucleic acid sequences, even during, e.g., extended passage in host cells and/or multiple infection, chromosomal integration, and/or excision events. Such reduced rates of homologous recombination are attributable, at least in part, to exploitation of the degeneracy of the genetic code during synthesis of the viral vectors as described herein.

Certain aspects of the instant invention relate to synthesis of fusion proteins and/or polypeptides (e.g., CIRs). Methods of producing fusion proteins are well known in the art of genetic engineering, with such methods including, e.g., gene splicing methods that rely upon the use of restriction enzymes, cloning vectors and, optionally, site directed mutagenesis procedures; and amplification-reliant methods of gene splicing (e.g., gene splicing by overlap extension ("gene SOE")).

Immune cells that express multiple different CIRs can possess enhanced recognition and killing of the same types of target cells via binding of different surface antigens, or, alternatively, may be capable of recognizing and killing distinct classes of target cells possessing different surface antigens. For example, as described in certain embodiments of the instant invention, T cells that express two different anti-tumor CIRs, anti-CEAsFvCD3Zeta and anti-PSMAsFcCD3Zeta, will be capable of targeting tumor cells that express either CEA or PSMA, or a combination of both antigens on their cell surface.

Two protein molecules comprising highly homologous polypeptide sequences that are encoded by similarly highly homologous nucleic acid sequences can be transduced to a single cell using a two vector approach as a means of reducing possible viral recombination events. For example, TCRCIRs of two-chain format, which consist of various VaCa and VbCb, respectively, but share identical signaling element polypeptide sequences (e.g., cytoplasmic domains of CD28 and/or CD3ζ). The two different vectors, each encoding one of the two homologous proteins of interest, might be generated from separate VPCs. However, the successful transduction rate of a single vector into mammalian cells, such as activated T cells exposed to a retrovirus, is often limited.

A number of additional CIRs that can be used in the methods and compositions of the present invention have been described in the literature, including U.S. Pat. No. 6,407,221 (Extracellular CD4-CD7TMD-Cytoplasmic ζ (CD3ζ)); U.S. Pat. No. 5,912,172 (Extracellular antibody-TMD and cytoplasmic ζ (CD3ζ)); U.S. Pat. No. 5,830,755 (native TCR alpha and TCR beta in one vector), U.S. Pat. No. 7,094,599 (CD4-based anti-HIV CIR); and U.S. Pat. No. 6,770,749 (anti-tumor TCRs).

Therapeutic Use of CIRs

The following list provides a number of examples of the uses of the molecules of the present invention. These examples should not be viewed as limiting.

A. Anti-JCV T Cell Receptors (TCRs) for Recognition of Polyomavirus JC (JCV) Derived Antigenic Peptides Progressive multifocal leukoencephalopathy (PML) is a deadly brain disease caused by the polyomavirus JC (JCV). The disease mainly arises in immunodeficient subjects. The ability to mount a cellular immune response against JCV has been shown to correlate with survival in PML, as evidenced in survivors by the presence of T cells expressing T cell receptors (TCRs) that recognize JCV peptides. Patients without such T cells have a rapidly fatal outcome. "Designer T cells" possessing anti-JCV TCRs by gene modification can provide a genuine therapy for PML by providing patients with otherwise missing T cells possessing anti-viral specificity.

Accordingly, in one aspect, the instant invention provides a viral vector comprising two nucleic acid sequences encoding homologous CIR polypeptides that each possesses an identical TCRZeta (CD3ζ) cytoplasmic domain, yet together comprise both the alpha and beta chain of an anti-JCV antibody. A designer T cell comprising this viral vector of the instant invention can be used in treatment of a subject infected with polyomavirus JC (JCV), as both alpha and beta chains of the anti-JCV antibody will be expressed on a single T cell, and JCV antigen binding will elicit a specific anti-JCV immune response via signalling through the TCRZeta (CD3ζ) signaling pathway of the T cell. The instant invention, therefore, also provides therapeutic methods of using such viral vectors against polyomavirus JC (JCV) and/or other antigen of an infective agent.

B. Anti-CEA CIRs

Carcinoembryonic antigen (CEA) is a human tumor antigen. (Schwartz et al. 1993 *Cancer: Principles and Practice of Oncology*. Lippincott. 929-77). A single chain anti-CEA sFv has been previously described (Nolan et al. 1999 *Clin Cancer Res.* 5: 3928-41). Anti-CEA molecules, e.g., an anti-CEA sFv as previously described, can be used in a CIR format to impart CEA binding to modified T cells.

Accordingly, "designer T cells" possessing anti-CEA antigen binding fragments (e.g., anti-CEA sFv molecules) that have been manipulated using the gene modification techniques described herein, can provide a therapy for CEA-expressing cancers by allowing such "designer T cells" to recognize such cancers. For example, in one aspect, the instant invention provides a viral vector comprising two nucleic acid sequences encoding homologous CIR polypeptides that each possess identical TCRZeta (CD3ζ) and CD28 cytoplasmic domains, yet together comprise both the alpha and beta chain of an anti-CEA antibody. A designer T cell comprising and expressing this viral vector of the instant invention can be used in treatment of a subject with a CEA-expressing cancer, as both alpha and beta chains of the anti-CEA antibody will be expressed on the single T cell, allowing for specific, high affinity binding, and such CEA antigen binding will elicit a specific immune response via signalling through both the TCRZeta (CD3ζ) and CD28 signaling pathways of the T cell, thereby inducing a specific immune response against CEA-expressing cancer cells. The instant invention, therefore, also provides cancer therapeutic methods that involve use of such viral vectors.

C. Anti-PSMA CIRs

Prostate specific membrane antigen (PSMA) is a human tumor antigen (Ma et al. 2004 *Prostate* 6: 12-25). A single chain anti-PSMA sFv has been previously described (ibid). Anti-PSMA molecules, e.g., an anti-PSMA sFv as previously described, can be used in a CIR format to impart PSMA binding to modified T cells. Accordingly, "designer T cells" possessing anti-PSMA antigen binding fragments (e.g., anti-PSMA sFv molecules) that have been manipulated using the gene modification techniques described herein, can provide a therapy for PSMA-expressing cancers by allowing such "designer T cells" to recognize such cancers.

For example, in one aspect, the instant invention provides a viral vector comprising two nucleic acid sequences encoding homologous CIR polypeptides that each possess identical TCRZeta (CD3ζ) and CD28 cytoplasmic domains, yet together comprise both the alpha and beta chain of an anti-PSMA antibody. A designer T cell comprising and expressing this viral vector can be used in treatment of a subject with a PSMA-expressing (e.g., prostate) cancer, as both alpha and beta chains of the anti-PSMA antibody will be expressed on the single T cell, allowing for specific, high affinity binding. Such PSMA antigen binding will, in turn, elicit a specific immune response via signalling through both the TCRZeta (CD3ζ) and CD28 signaling pathways of the T cell, thereby inducing a specific immune response against PSMA-expressing cancer cells. The instant invention, therefore, also provides cancer therapeutic methods that involve use of such viral vectors.

D. CIRs Possessing Enhanced TCR Stimulation Properties

T cells require both primary and costimulatory signals for optimal activation. The primary antigen-specific signal is delivered by engagement of the TCR. The second antigen-independent costimulatory signal is mediated by engagement of the T cell surface costimulatory molecule CD28 with its target cell ligand, B7. However, many tumor cells do not express these costimulatory molecules (Willemsen et al. 2005 *J. Immunol.* 174: 7853-58).

CD28 co-stimulation (signal 2) during T cell activation through TCR (signal 1) has been shown to promote sustained T cell proliferation (Shahinian et al. 1993 *Science* 261: 609-12; Lenschow et al. 1996 *Annu Rev Immunol.* 14: 233-58), decreased activation-induced cell death (AICD) and improved long-term lymphocyte survival (Sperling et al. 1996 *J Immunol.* 157: 3909-17). To combine activation and co-stimulatory functions within a single receptor, CIRs can be constructed that are comprised of both TCRZeta (CD3ζ) and CD28 sequences in the same molecule (Hombach et al. 2001 *Cancer Res* 61: 1976-82; Haynes et al. 2002 *Blood.* 100: 3155-63 (Erratum in: *Blood.* 2003; 101: 3808); Haynes et al. 2002 *J Immunol.* 2002; 169:5780-6. (Erratum in: *J Immunol.* 2003; 170: 3440)). Such IgCD28Z molecules have been demonstrated to possess superior function in T cells for cytotoxicity, proliferation, and IL2 and IFNγ production (Hombach et al. 2001 *Cancer Res* 61: 1976-82; Haynes et al. 2002 *Blood.* 100: 3155-63 (Erratum in: *Blood.* 2003; 101: 3808); Haynes et al. 2002 *J Immunol.* 169:5780-6. (Erratum in: *J Immunol.* 2003 170: 3440)).

Accordingly, in one aspect, the instant invention provides a viral vector comprising two or more nucleic acid sequences encoding CIR polypeptides that possess highly homologous (e.g., identical) extracellular antigen-binding domains, yet comprise distinct cytoplasmic domains. For example, one viral vector-encoded CIR polypeptide can comprise a TCRZeta (CD3ζ) cytoplasmic domain, while another CIR polypeptide encoded by the same viral vector comprises a CD28 cytoplasmic domain, thereby allowing for the binding of a single type of antigen to a T cell that expresses both CIR polypeptides to signal through both the T cell receptor pathway and the normally antigen-independent CD28 signaling pathway, resulting in an enhanced immune response to, e.g., a cancer or infectious disease antigen.

E. CIRs Comprising FcεRI

The FcεRI complex is the high affinity cell surface receptor for the Fc region of antigen specific immunoglobulin E (IgE) molecules. FcεRI is composed of three distinct polypeptides. The α chain (FcεRIα) binds the Fc portion of IgE with high affinity, and the β chain (FcεRIβ) has four transmembrane domains between amino- and carboxyl-terminal cytoplasmic tails. A homodimer of two disulfide-linked γ chains (FcεRIγ) completes the tetrameric structure. In humans, FcεRI controls the activation of mast cells and basophils, and participates in IgE-mediated antigen presentation. Multivalent antigens bind and crosslink IgE molecules held at the cell surface by FcεRI. Receptor aggregation induces multiple signaling pathways that control diverse effector responses, including secretion of allergic mediators and the induction of cytokine gene transcription (such as IL-4, IL-6, TNFα and GM-CSF). FcεRI, therefore, is central to the induction and maintenance of an allergic response and physiologically may confer protection in parasitic infections.

In one aspect, the instant invention provides a viral vector comprising two or more nucleic acid sequences encoding CIR polypeptides that possess distinct extracellular TCRa and TCRb domains, respectively, yet each comprise identical FcεRIγ cytoplasmic domains. The expression of both such fusion proteins on a single T cell allows for the activation of either TCRα or TCRβ to induce the FcεRIγ signaling pathway of the designer T cell, which, in turn, induces multiple signaling pathways that control diverse effector responses, including secretion of allergic mediators and the induction of cytokine gene transcription (such as IL-4, IL-6, TNFα and GM-CSF).

Other protein domains for signaling are by extension covered under this invention with further examples as provided in the Summary section, page 5.

CIRs Comprising Antigen Binding Fragments

In certain embodiments of the present invention, CIRs that comprise antigen binding fragments (e.g., single chain Fv molecules) are employed. While specific anti-CEA and anti-PSMA sFv molecules have been previously described, one of skill in the art will recognize that the present invention is not limited to only constructs that employ such sFv molecules. The sFv (interchangably referred to as "scFv" herein) molecules can be replaced by any number of different antigen binding domains commonly known in the art, ranging from a minimal peptide binding domain, to a structured antigen binding domain from a phase library, to antibody-like domains using different methods to hold the heavy and light chain (or peptide-binding domains of each) together. The arrangement can be multimeric such as in a diabody format. It is possible that the T cell receptor variant is also a multimer. Multimers are most likely caused by cross pairing of the variable portion of the light and heavy chains into what has been referred to by Winters as a diabody. Additionally and/or alternatively, antigen binding fragments employed in CIR polypeptides of the present invention can include non-immunoglobulin scaffold proteins (e.g., fibronectin molecules, lipocalin molecules, etc.) adapted and/or selected for recognition of target antigens via art-recognized methods.

Exploitation of the Degeneracy of the Genetic Code

The 64 codons of the eukaryotic genetic code encode for only the 20 naturally-occurring amino acids and three stop codons, rendering the genetic code degenerate with respect to the encoding of amino acid residues. Specific codon sequences and their corresponding encoded amino acid residues or stop codons are shown below.

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

While methionine (Met, M) and tryptophan (Trp, W) are uniquely encoded by ATG and TTG, respectively, all other amino acid residues may be encoded by two or more distinct codons, often differing by a single base, but in some cases differing from one another at two of three nucleic acid residues. This degeneracy of the genetic code allows for the encoding of identical polypeptides by non-identical nucleic acid sequences. The present invention, at least in some respects, relies upon introducing (and, in some embodiments, maximizing) non-identity between two nucleic acid sequences that encode the same or highly homologous polypeptides (e.g., CIR polypeptides). By maximizing the difference between nucleic acid sequences present in a single vector (e.g., a viral vector comprising viral genomic RNA possessing genes of interest), the possibility of homologous recombination-directed viral recombination between such sequences is minimized. Accordingly, via directed use of degenerate codons in design of viral vectors, genes encoding identical and/or highly homologous polypeptide sequences can be propagated on a single vector with dramatically reduced possibility of homologous recombination events occurring between nucleic acid sequences encoding the highly homologous polypeptides.

Thus, in at least one embodiment, the degeneracy of the genetic code may be exploited through alteration of the codons that encode CIRs, thereby facilitating viral gene transduction of mammalian cells and minimizing viral recombination events, particularly within highly homologous (e.g., identical) TMD and intracellular portions of the CIRs.

Selection of Degenerate Nucleic Acid Sequences

To determine which codons within a nucleic acid sequence can be varied without impact on an encoded polypeptide sequence, the nucleic acid sequence can be inspected to determine reading frame and codons, and one or more degenerate nucleic acid sequences that encode for an identical polypeptide sequence can be determined via use of the genetic code (e.g., if an original, e.g., native, nucleic acid sequence encodes a glycine residue with a "GGT" codon in a polypeptide-encoding reading frame, degenerate nucleic acid sequences that encode for an identical polypeptide sequence would include the three additional sequences that encode the same glycine residue with "GGC," "GGA," and "GGG"). As few as a single codon within a nucleic acid sequence can be replaced by a degenerate codon for purpose of forming a variant nucleic acid sequence that encodes the same polypeptide sequence as the original nucleic acid sequence. However, in preferred embodiments of the present invention, multiple codons of the first nucleic acid sequence are replaced by degenerate codons, to an extent sufficient to dramatically reduce homologous recombination events between the original nucleic acid sequence and the variant (degenerate) nucleic acid sequence, as further described infra.

Selection of nucleic acid sequences that contain degenerate codon sequences can be performed manually and/or randomly for a chosen nucleic acid sequence to be altered. In addition to manual and/or random selection of alternative sequences that contain degenerate codons, a variety of resources are available for generation of nucleic acid sequences containing degenerate codons, including, e.g., a program that allows for selection of commonly used, but degenerate codons according to previously published information, which may be found on the Kazusa DNA Res. Institute (KDRI)'s world-wide-web URL at kazusa(dot)or (dot)jp/codon/internet (Nakamura et al. 2000 *Nucleic Acids Res.* 28(1): 292). Additionally and/or alternatively, software that facilitates the design of artificial DNA (and corresponding RNA) segments, such as Gene Designer (available from DNA2.0, Inc. (AUTM), Newark, Calif., USA; Villalobos et al. 2006 *BMC Bioinformatics* 7: 285.) can be used.

Selection of nucleic acid sequences comprising degenerate codons can be performed upon a single nucleic acid sequence (including, e.g., performance upon an identical nucleic acid sequence encoding an identical polypeptide domain within two distinct polypeptide sequences (e.g., two distinct CIRs)) or upon two homologous nucleic acid sequences encoding highly homologous polypeptide sequences (e.g., polypeptide sequences greater than 80% identical, more preferably greater than 85% identical, more preferably greater than 90% identical, greater than 95% identical, greater than 96% identical, greater than 97% identical, greater than 98% identical, or greater than 99% identical). In certain embodiments of the invention, such highly homologous polypeptide sequences may constitute a polypeptide domain within a chimeric polypeptide/protein sequence (e.g., a TMD within a CIR polypeptide). For such highly homologous polypeptides, use of degenerate codons within nucleic acid sequences encoding such polypeptides may be applied to either sequence individually or to both sequences in order to enhance homology reduction between the nucleic acid sequences encoding the highly homologous polypeptides. The extent of degeneracy that can be incorporated in certain nucleic acid sequences of the invention that encode highly homologous peptides is considered in greater detail below (refer to "Inhibition of Homologous Recombination via Homology Reduction").

Determination and Use of Polypeptide Domains

In certain embodiments of the present invention, the domain structure of polypeptides is determined and/or utilized for synthesis of chimeric polypeptides, e.g., CIRs. Accordingly, certain vectors of the present invention encode two or more polypeptides, e.g., CIRs, that possess highly homologous and/or identical polypeptide domain structures, though regions of the polypeptides outside of the highly homologous and/or identical domain structures may be less homologous (e.g., unrelated and/or more distantly related polypeptides). Because unaltered nucleic acids that encode highly homologous and/or identical domains within two otherwise unrelated and/or distantly related polypeptides can also drive homologous recombination events, it is within the scope of the present invention to introduce degenerate codons across such potentially limited, highly homologous domain regions within a chimeric polypeptide(s), for purpose of reducing the probability of homologous recombination events occurring between chimeric polypeptides contained within a single vector. Accordingly, determination of the domain structure(s) of polypeptides is an art-recognized facet of certain embodiments of the present invention.

The domain structure of polypeptides can be determined by a number of art-recognized methods. For example, determination of the location of a transmembrane domain (TMD) of a polypeptide can be determined using traditional hydropathy analysis, which, for single pass transmembrane proteins that localize to the cell surface, can divide a protein into extracellular domain, TMD, and cytoplasmic domain fragments (with overall orientation within the plasma membrane determined based upon whether the polypeptide is a type I or type II membrane protein). Additional examples of resources that can be used to determine the domain structure of a polypeptide include the SOSUI system, which can be used for prediction of transmembrane helices and signal sequences of protein sequences, and other protein domain architectures can be analysed using Pfam (Protein families database of alignments and HMMs).

Protein domain descriptions can be obtained from Prosite (contains 1030 documentation entries that describe 1366 different patterns, rules and profiles/matrices), and Pfam. A description of the Pfam database can be found in Sonhammer et al. (1997) *Proteins* 28(3): 405-420.

A "portion" of a protein refers to that length of amino acid sequence which would retain at least one biological activity, a domain identified by PFAM or PRINTS analysis or an antigenic determinant of the protein identified using Kate-Doolittle algorithms of the PROTEAN program (DNAS-TAR, Madison, Wis.).

As mentioned above, hydropathy analysis can most readily be used to predict and/or determine transmembrane domains (TMDs) within a polypeptide. TMDs are among the shortest domains readily discerned by domain recognition programs. In general, the individual domain structures within a polypeptide will tend to be at least 10 amino acid residues in length, more commonly at least 15 amino acid residues in length, commonly at least 16 amino acid residues in length, commonly at least 17 amino acid residues in length, commonly at least 18 amino acid residues in length, commonly at least 19 amino acid residues in length, commonly at least 20 amino acid residues in length, commonly at least 21 amino acid residues in length, commonly at least 22 amino acid residues in length, commonly at least 25 amino acid residues in length, commonly at least 30 amino acid residues in length, commonly at least 35 amino acid residues in length, commonly at least 40 amino acid residues in length, commonly at least 45 amino acid residues in length, or commonly at least 50 amino acid residues in length. Some of the shortest polypeptide domains, e.g., TMDs, are generally about 15-30 amino acid residues in length, commonly about 17-25 amino acid residues in length, commonly about 18-22 amino acid residues in length, or commonly about 20 amino acid residues in length.

Once degenerate nucleic acid sequences are selected, homology values may be verified for newly designed sequences in comparison(s) with the original/counterpart genes and, optionally, vector nucleic acid sequence (e.g., retroviral vector RNA sequence), respectively, using relevant software (such as web-based software available from San Diego State University, San Diego, Calif., USA). In certain embodiments, overall nucleic acid homology is less than 80% and/or the length of nucleotide sequences that share over 80% homology is not longer than 50-100 nucleotides.

Inhibition of Homologous Recombination Via Homology Reduction

It is generally accepted that homology (% identity) levels must be very high over a sufficiently long region for recombination event(s) to take place at a significant frequency. In particular, the data from the literature suggest that a region of perfect homology of at least equal to about 200 nucleotides in length is required for the occurrence of such events. Indeed, even though recombination events can take place over shorter regions, their frequency is much lower and irregular. Moreover, over such a region whose homology is reduced by 19%, it appears that the frequency of recombination is reduced by a factor of 1000 (Waldman and Liskay, 1987).

As described herein, nucleic acid sequences can be modified in various ways. With regard to coding sequence, modifications can be introduced based on the degeneracy of the genetic code, as described in more detail above. In this way, regions of otherwise identical sequence are disrupted, thereby reducing homology yet allowing for the expression product to remain unchanged.

The invention resides therefore, at least in part, in a modification of the sequence of nucleic acid sequences (e.g., CIRs) within a vector (e.g., retroviral vector) in such a way as to prevent the pairing between the two homologous regions. The modification makes it possible to decrease the length and degree of homology between the two regions concerned.

Advantageously, in one method of the invention, at least one nucleic acid sequence is degenerated, within a region that would otherwise be highly homologous and/or identical at the amino acid level and, therefore, likely to be involved in homologous recombination events, in a proportion of 1 non-identical base pair at least every 50 base pairs, 1 non-identical base pair at least every 20 base pairs, or 1 non-identical base pair at least every 20 base pairs. More preferably, it is degenerated in a proportion of 1 non-identical base pair at least every 10 base pairs or 1 non-identical base pair at least every 5 base pairs.

In certain embodiments, a sequence can be degenerated over all the possible positions. The degeneracy of a sequence according to the invention is advantageously produced as a function of the codon use of the cell or organism in which the nucleic acid should be used. In the case of a viral vector whose production is carried out in a human cell line, it is particularly advantageous to degenerate the sequences by favouring the preferred codon use in humans when this choice is possible (refer to U.S. Pat. No. 6,410,298).

Moreover, further modifications can be introduced into the nucleic acid sequence. Thus, in, e.g., noncoding regions, it is possible to reduce the size of certain elements (regulatory sequences for expression, promoters) or to modify these elements or to substitute certain other elements with heterologous regions.

It may also be possible to introduce one or more substitutions of amino acid residues within a polypeptide sequence of the invention for purpose of reducing homology. Such modification(s) can be informed by, e.g., alignments of homologous and/or orthologous sequences that identify evolutionarily non-conserved amino acids that are of greatest interest for performance of such substitutions. For example, where native polypeptide(s) and/or domains of native polypeptide(s) derived from both human and chimpanzee sequences are non-identical yet known to be functionally interchangeable, both such sequences can be used within a vector (e.g., within a CIR polypeptide) of the present invention. Alternatively, individual amino acid substitutions selected from among those residues that are non-identical between compared sequences can be performed to reduce homology between nucleic acid sequences, and such approaches can be combined with the use of degenerate codon sequences as described herein, in order to achieve generation of a single vector comprising two nucleic acid sequences possessing dramatically reduced levels of homology yet encoding two identical or highly homologous polypeptides (e.g., CIR polypeptides).

In certain embodiments of the present invention, when two nucleic acid sequences encoding identical and/or highly homologous polypeptide sequence(s) (e.g., nucleic acid sequences encoding CIRs possessing identical CD3ζ cytoplasmic domain polypeptides) contained within a single vector of the invention are compared, at least 2% of codons within the region of nucleic acid sequence that encodes the identical and/or highly homologous domain of polypeptide sequence are non-identical, degenerate codons. In certain additional embodiments, at least 5% of such codons are non-identical, optionally at least 10% of such codons are non-identical, optionally at least 15% of such codons are non-identical, optionally at least 20% of such codons are non-identical, optionally at least 25% of such codons are non-identical, optionally at least 30% of such codons are non-identical, optionally at least 35% of such codons are non-identical, optionally at least 40% of such codons are non-identical, optionally at least 45% of such codons are non-identical, optionally at least 50% of such codons are non-identical, optionally at least 55% of such codons are non-identical, optionally at least 60% of such codons are non-identical, optionally at least 65% of such codons are non-identical, optionally at least 70% of such codons are non-identical, optionally at least 75% of such codons are non-identical, optionally at least 80% of such codons are non-identical, optionally at least 85% of such codons are non-identical, optionally at least 90% of such codons are non-identical, or optionally at least 95% of such codons are non-identical. Optionally, all codons other than those encoding methionine or tryptophan are non-identical between the two compared nucleic acid sequences.

In certain embodiments of the present invention, when two nucleic acid sequences encoding identical and/or highly homologous polypeptide sequence(s) (e.g., nucleic acid sequences encoding CIRs possessing identical CD3ζ cytoplasmic domain polypeptides) contained within a single vector of the invention are compared, at least 1 codon within the region of nucleic acid sequence that encodes the identical and/or highly homologous domain of polypeptide sequence is a non-identical, degenerate codon. In certain additional embodiments, at least 2 such codons are non-identical, optionally at least 3 such codons are non-identical, optionally at least 4 such codons are non-identical, optionally at least 5 such codons are non-identical, optionally at least 10 such codons are non-identical, optionally at least 15 such codons are non-identical, optionally at least 20 such codons are non-identical, optionally at least 25 such codons are non-identical, optionally at least 30 such codons are non-identical, optionally at least 35 such codons are non-identical, optionally at least 40 such codons are non-identical, optionally at least 45 such codons are non-identical, optionally at least 50 such codons are non-identical, optionally at least 55 such codons are non-identical, optionally at least 60 such codons are non-identical, optionally at least 65 such codons are non-identical, optionally at least 70 such codons are non-identical, optionally at least 75 such codons are non-identical, optionally at least 80 such codons are non-identical, optionally at least 85 such codons are non-identical, optionally at least 90 such codons are non-identical, optionally at least 95 such codons are non-identical, optionally at least 100 such codons are non-identical, optionally at least 110 such codons are non-identical, optionally at least 120 such codons are non-identical, optionally at least 130 such codons are non-identical, optionally at least 140 such codons are non-identical, optionally at least 150 such codons are non-identical, optionally at least 160 such codons are non-identical, optionally at least 170 such codons are non-identical, optionally at least 180 such codons are non-identical, optionally at least 190 such codons are non-identical, or optionally at least 200 such codons are non-identical.

In certain embodiments, the percent identity values of two nucleic acid sequences that encode for identical and/or highly homologous polypeptides (e.g., certain CIR polypeptide domain sequences, e.g., the CD3ζ cytoplasmic domain of two CIRs of the invention located upon the same vector yet wherein at least one nucleic acid sequence has been modified through use of degenerate codons to reduce nucleic acid homology) are reduced to less than 98% identity between such nucleic acid sequences, more preferably less than 95% identity between such nucleic acid sequences, more preferably less than 90% identity between such nucleic acid sequences, more preferably less than 85% identity between such nucleic acid sequences, more preferably less than 80% identity between such nucleic acid sequences, optionally less than 75% identity between such nucleic acid sequences, optionally less than 70% identity between such nucleic acid sequences, optionally less than 65% identity between such nucleic acid sequences, or optionally less than 60% identity between such nucleic acid sequences.

Therapeutic Use of Vectors Comprising Degenerate CIR Sequences

The vectors of the present invention, possessing mutated genes as described infra, can be used for applications including, but not limited to, gene therapy and immunotherapy. For example, immunotherapy for infectious disease may be performed via use of CIRs that recognize the infectious disease, or cancer may be treated using T cells that express antigen-specific CIRs.

In certain embodiments, production of a T cell that expresses such CIRs may be accomplished via retroviral gene therapy.

Retroviral Gene Therapy

Gene therapy includes any one or more of: the addition, the replacement, the deletion, the supplementation, the manipulation of one or more nucleotide sequences in, for example, one or more targeted sites, e.g., targeted cells. If the targeted sites are targeted cells, then the cells may be part of a tissue or an organ. General teachings on gene therapy may be found in *Molecular Biology* (Ed Robert Meyers, Pub VCH, e.g., refer to pages 556-558).

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favorable phenotype; cells can be manipulated at the molecular level to treat cancer (Schmidt-Wolf and Schmidt-Wolf, 1994, Annals of Hematology 69:273-279) or other conditions—such as immune, cardiovascular, neurological, inflammatory or infectious disorders; antigens can be manipulated and/or introduced to elicit an immune response—such as genetic vaccination.

In certain embodiments of the invention, retroviral gene therapy is performed upon T cells in vitro to achieve T cell expression of CIR molecules. In other embodiments of the invention, retroviral gene therapy that introduces CIR molecules to T cells is performed upon such T cells in vivo.

Retroviruses and Lentiviruses

In recent years, retroviruses have been proposed for use in gene therapy. Essentially, retroviruses are RNA viruses with a life cycle different from that of lytic viruses. In this regard, when a retrovirus infects a cell, its genome is converted to a DNA form. In other words, a retrovirus is an infectious entity that replicates through a DNA intermediate.

Lentivirus is a genus of slow viruses within the Retroviridae (retrovirus) family. Lentiviruses are characterized by a long incubation period, and can deliver a significant amount of genetic information into the DNA of a host cell. Accordingly, they are one of the most efficient forms of gene delivery vector. HIV, SIV and FIV are all examples of lentiviruses. Notably, lentiviruses are capable of infecting neighboring cells in direct contact with host cells, absent the need to form extracellular particles (though virions can be produced and harvested for implementation of cell-free infection of newly-targeted cells).

Any of the following exemplary retroviruses are contemplated for use in the methods of the invention: murine leukemia virus (MLV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV), AKR (endogenous) murine leukemia virus, Avian carcinoma, Mill Hill virus 2, Avian leukosis virus-RSA, Avian myeloblastosis virus, Avian myelocytomatosis virus 29, Bovine syncytial virus, Caprine arthritis encephalitis virus, Chick syncytial virus, Feline leukemia virus, Feline syncytial virus, Finkel-Biskis-Jinkins murine sarcoma virus, Friend murine leukemia virus, Fujinami sarcoma virus, Gardner-Arnstein feline sarcoma virus, Gibbon ape leukemia virus, Guinea pig type C oncovirus, Hardy-Auckerman feline sarcoma virus, Harvey murine sarcoma virus, Human foamy virus, Human spumavirus, Human T-lymphotropic virus 1, Human T-lymphotropic virus 2, Jaagsiekte virus, Kirsten murine sarcoma virus, Langur virus, Mason-Pfizer monkey vikrus, Moloney murine sarcoma virus, Ovine pulmonary adenocarcinoma virus, Porcine type C oncovirus, Reticuloendotheliosis virus, Simian foamy virus, Simian sarcoma virus, Simian T-lymphotropic virus, Simian type D virus 1, Snyder-Theilen feline sarcoma virus, Squirrel monkey retrovirus, Trager duck spleen necrosis virus, UR2 sarcoma virus, Viper retrovirus, Visna/maedi virus, Woolly monkey sarcoma virus, and Y73 sarcoma virus human-, simian-, feline-, and bovine immunodeficiency viruses (HIV, SIV, FIV, BIV).

A detailed list of retroviruses can be found in Coffin et al ("Retroviruses" 1997 Cold Spring Harbour Laboratory Press Eds: J M Coffin, S M Hughes, H E Varmus pp. 758-763). Details on the genomic structure of some retroviruses can also be found in the art. By way of example, details regarding HIV structure can be found in NCBI Genbank (i.e. Genome Accession No. AF033819).

Retroviral Transduction of CIRs into Primary Human Lymphocytes

The use of retroviral vectors to transduce chimeric immune receptors into primary human lymphocytes has been limited by low gene transfer efficiency when viral supernatant infections have been carried out. Transfer rates into primary human T cells using amphotropic virus in such prior studies has ranged from 1 to 12% (Bunnell, 1995 Proc Natl Acad Sci USA. 92(17): 7739-43). Certain strategies have been employed to increase the transduction rates to 20-50%, as described in WO 03/033670.

The methods of the instant invention allow for use of a single vector possessing two or more nucleic acid sequences encoding highly homologous polypeptide sequences for transduction into host cells, thereby overcoming problems associated with low transduction efficiencies of retroviral vectors into host cells.

Retrovirus Structure

All retroviruses contain three major coding domains, gag, pol, and env, which code for essential virion proteins. Nevertheless, retroviruses may be broadly divided into two categories: "simple" and "complex". These categories are distinguishable by the organization of their genomes. Simple retroviruses usually carry only this elementary information. In contrast, complex retroviruses also code for additional regulatory proteins derived from multiple spliced messages.

Retroviruses can be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbour Laboratory Press Eds: J M Coffin, S M Hughes, H E Varmus pp 1-25).

All oncogenic members except the human T-cell leukemia virus-bovine leukemia virus (HTLV-BLV) are simple retroviruses. HTLV, BLV and the lentiviruses and spumaviruses are complex. Some of the best-studied oncogenic retroviruses are Rous sarcoma virus (RSV), mouse mammary tumour virus (MMTV) and murine leukemia virus (MLV) and the human T-cell leukemia virus (HTLV).

The lentivirus group can be split even further into "primate" and "non-primate". Examples of primate lentiviruses useful in the methods and compositions of the instant invention include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiencey virus (FIV) and bovine immunodeficiencey virus (BIV).

In a typical recombinant retroviral vector for use in gene therapy, at least part of one or more of the gag, pol and env protein coding regions may be removed from the virus. This makes the retroviral vector replication-defective. The removed portions can be replaced by a nucleotide of interest (NOI; e.g., a CIR sequence) in order to generate a virus capable of integrating its genome into a host genome but wherein the modified viral genome is unable to propagate itself due to a lack of structural proteins. When integrated in the host genome, expression of the NOI occurs, resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest, such as a targeted cell or a targeted cell population (e.g., human T cell population).

It is possible to propagate and isolate quantities of retroviral vectors (e.g., to prepare suitable titres of the retroviral vector) for subsequent transduction of, for example, a site of interest via use of a combination of a packaging or helper cell line and a recombinant vector.

In some instances, propagation and isolation can entail isolation of the retroviral gag, pol and env genes and their separate introduction into a host cell to produce a "packaging cell line". The packaging cell line produces the proteins required for packaging retroviral DNA but it cannot bring about encapsidation due to the lack of a psi region. However, when a recombinant vector carrying a NOI and a psi region is introduced into the packaging cell line, the helper proteins can package the psi-positive recombinant vector to produce the recombinant virus stock. This can be used to infect cells to introduce the NOI (e.g., CIR) into the genome of the cells. The recombinant virus whose genome lacks all genes required to make viral proteins can infect only once and cannot propagate. Hence, the NOI (e.g., CIR) is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The above technique, however, can be problematic in the sense that viral titre levels are not always at a satisfactory level. Nevertheless, the design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production.

In another embodiment, a strategy sometimes referred to as the three plasmid transfection method is used in the methods of the invention (Soneoka et al. 1995 *Nucl. Acids Res.* 23: 628-633). In this method, packaging cells in which the gag, pol and env viral coding regions are carried on separate expression plasmids are independently transfected into a packaging cell line, such that three recombinant events are required for wild type viral production.

Transient transfection can be used to measure vector production when vectors are being developed. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing a NOI (e.g., CIR). Vector production involves transient transfection of one or more of these components into cells containing the other required components. If the vector encodes toxic genes or genes that interfere with the replication of the host cell, such as inhibitors of the cell cycle or genes that induce apotosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, *PNAS* 90:8392-8396). The compositions and methods of the present invention provide particular advantage in such transient transfection strategies, in view of their reliance upon a single viral vector transformation event, rather than multiple viral vector transformation events.

In view of the toxicity of some HIV proteins—which can make it difficult to generate stable HIV-based packaging cells—HIV vectors are usually made by transient transfection of vector and helper virus. Some workers have even replaced the HIV Env protein with that of vesicular stomatis virus (VSV). Insertion of the Env protein of VSV facilitates vector concentration as HIV/VSV-G vectors with titres of $5 \times 10^5$ ($10^8$ after concentration) were generated by transient transfection (Naldini et al 1996 *Science* 272: 263-267). Thus, transient transfection of HIV vectors can provide a useful strategy for the generation of high titre vectors (Yee et al 1994 *PNAS* 91: 9564-9568). A drawback, however, with this approach is that the VSV-G protein is quite toxic to cells.

Replacement of the env gene with a heterologous env gene is an example of a technique or strategy called pseudotyping. Pseudotyping is not a new phenomenon and examples may be found in WO 98/05759, WO 98/05754, WO 97/17457, WO 96/09400, WO 91/00047 and Mebatsion et al 1997 *Cell* 90: 841-847. Various methods of pseudotyping are described, e.g., in WO 03/066868.

Retroviral Vectors

The present invention, at least in part, provides a retroviral vector that contains two or more nucleic acid sequences that encode homologous, optionally perfectly identical or highly identical, polypeptides, wherein the at least two nucleic acid sequences, by design, are insufficiently homologous to enable homologous recombination to occur between the two or more highly homologous, optionally identical, nucleic acid sequences.

Thus, in certain embodiments, the present invention provides a retroviral vector having at least two exogenous nucleic acid sequences that encode homologous polypeptides, e.g., CIR polypeptides. This retroviral vector is useful in gene therapy.

The retroviral vectors of the present invention are useful for the delivery of nucleic acid sequences expressing at least two homologous polypeptide (e.g., CIR polypeptide) sequences to cells (e.g., T cells) in vivo and in vitro, in particular the delivery of therapeutically active nucleic acid sequences that encode CIR polypeptides. Two or more selected nucleic acid sequences encoding homologous polypeptides (e.g., CIR polypeptides) can be incorporated in the same vector genome for expression in the target cell. The homologous polypeptide-encoding (e.g., CIR-encoding) nucleic acid sequences can have one or more expression control sequences of their own, or their expression can be controlled by the vector LTRs. For appropriate expression of the polypeptides, e.g., CIRs, a promoter may be included in or between the LTRs which is preferentially active under certain conditions or in certain cell types. In certain embodiments of the present invention, an IRES is included between nucleotide sequences encoding highly homologous (e.g., identical) polypeptides and/or polypeptide domains. In certain other embodiments, nucleotides encoding a 'self-cleaving' 2A peptide are included between nucleotide sequences encoding highly homologous (e.g., identical) polypeptides and/or polypeptide domains. The plurality of nucleic acid sequences that encode homologous polypeptides (e.g., CIR polypeptides) can be sense sequences, antisense sequences, or combinations thereof.

In certain embodiments of the instant invention, the two or more selected nucleic acid sequences encoding homologous polypeptides (e.g., CIR polypeptides) can be incorporated in two or more distinct viral vectors for expression in a target cell. While such two vector approaches confront the potential difficulties associated with achieving co-transduction of independent viral vectors into the same host cell, the methods of the invention may be implemented to reduce the probability of homologous recombination events occurring between such co-transduced highly homologous (e.g., identical) polypeptides and/or polypeptide domains. As for single viral vector embodiments, degenerate codons can be employed during synthesis of nucleic acid sequences to reduce homology levels present between nucleic acid sequences encoding homologous (e.g., identical) polypeptides and/or polypeptide domains. Polypeptide-encoding (e.g., CIR-encoding) nucleic acid sequences can have one or more expression control sequences of their own, or their expression can be controlled by the vector LTRs. For appropriate expression of the homologous polypeptides, e.g., CIRs, a promoter may be included in or between the LTRs which is preferentially active under certain conditions or in certain cell types. In certain embodiments of the present invention, an IRES is included in appropriate position to induce transcription and expression of nucleotide sequences encoding highly homologous (e.g., identical) polypeptides and/or polypeptide domains. As for single viral vector compositions and methods of the instant invention, the plurality of nucleic acid sequences that encode homologous polypeptides (e.g., CIR polypeptides) may be sense sequences, antisense sequences, or combinations thereof.

The retroviral vector genome of the present invention may generally comprise LTRs at the 5' and 3' ends, two or more NOIs (e.g., CIRs) including therapeutically active genes and/or marker genes, or suitable insertion sites for inserting two or more NOIs, and a packaging signal to enable the genome to be packaged into a vector particle in a producer cell. At least one of the NOIs of the present invention is modified to incorporate at least one degenerate codon sequence (as compared to another NOI sequence contained within the same viral vector), optionally enough degenerate codons are introduced to reduce nucleic acid identity between sequences encoding highly homologous polypeptides to less than, e.g., 80% identity, thereby significantly reducing the probability of a homologous recombination event between the NOI sequences. Within the retroviral vectors of the present invention, there may be suitable primer binding sites and integration sites to allow reverse transcription of the vector RNA to DNA, and integration of the proviral DNA into the target cell genome. In certain embodiments, the retroviral vector particle has a reverse transcription system (compatible reverse transcription and primer binding sites) and an integration system (compatible integrase and integration sites).

Thus, in accordance with the present invention, it is possible to manipulate the viral genome or the retroviral vector nucleotide sequence, so that viral genes are replaced or supplemented with two or more nucleic acid sequences encoding homologous CIR polypeptides. Such retroviral vector nucleotide sequences will also contain genes that enable identification of transformed cells. Such genes may be any one or more of selection gene(s) and marker gene(s). Many different selectable markers have been used successfully in retroviral vectors. These are reviewed in "Retroviruses" (1997 Cold Spring Harbour Laboratory Press Eds: J M Coffin, S M Hughes, H E Varmus pp 444) and include, but are not limited to, the bacterial neomycin and hygromycin phosphotransferase genes which confer resistance to G418- and hygromycin, respectively; a mutant mouse dihydrofolate reductase gene which confers resistance to methotrexate; the bacterial gpt gene which allows cells to grow in medium containing mycophenolic acid, xanthine and aminopterin; the bacterial hisD gene which allows cells to grow in medium without histidine but containing histidinol; the multidrug resistance gene (mdr) which confers resistance to a variety of drugs; and the bacterial genes which confer resistance to puromycin or phleomycin. All of these markers are dominant selectable and allow for chemical selection of cells expressing these genes.

Therapeutic Use of Retroviral Vectors and Recombinant Retrovirus

In certain embodiments of the present invention, diseases which may be treated by the compositions and methods of the invention include, but are not limited to infectious diseases and cancer, though any disease or disorder for which "designer T cells" and modified NK cells can be used for treatment of the disease or disorder is within the scope of the present invention. Accordingly, within such embodiments, target cells for gene therapy using retroviral vectors include but are not limited to T cells and NK cells.

Within the retroviral vectors of the present invention, two or more nucleic acid sequences that encode highly homologous polypeptides, e.g., CIR polypeptides, can be under the transcriptional control of the viral LTRs. However, in certain embodiments of the present invention, the two or more nucleic acid sequences of the retroviral vector are under the transcriptional control of an IRES element. Alternatively, a combination of enhancer-promoter elements can be present in order to achieve higher levels of expression. The promoter-enhancer elements are preferably strongly active or capable of being strongly induced in the target cells. An example of a strongly active promoter-enhancer combination is a human cytomegalovirus (HCMV) major intermediate early (MIE) promoter/enhancer combination. The promoter-enhancer combination may be tissue or temporally restricted in their activity. Examples of a suitable tissue restricted promoter-enhancer combinations are those which are highly active in tumor cells such as a promoter-enhancer combination from a MUC1 gene or a CEA gene.

Hypoxia or ischemia regulatable expression is also useful in certain embodiments of the invention. Hypoxia is a powerful regulator of gene expression in a wide range of different cell types and acts by the induction of the activity of hypoxia-inducible transcription factors such as hypoxia inducible factor-1 (HIF-1) (Wang and Semenza 1993 *PNAS (USA)* 90: 430) which bind to cognate DNA recognition sites, the hypoxia responsive elements (HREs) on various gene promoters. A multimeric form of HRE from the mouse phosphoglycerate kinase-1 (PGK-1) gene has been used to control expression of both marker and therapeutic genes by human fibrosarcoma cells in response to hypoxia in vitro and within solid tumors in vivo (Firth et al 1994 *PNAS* 91(14): 6496-6500; Dachs et al 1997 *Nature Med.* 5: 515). Alternatively, the fact that glucose deprivation is also present in ischemic areas of tumours can be used to activate heterologous gene expression, especially in tumors. A truncated 632 base pair sequence of the grp 78 gene promoter, known to be activated specifically by glucose deprivation, has been shown to be capable of driving high level expression of a reporter gene in murine tumors in vivo (Gazit et al 1995 *Cancer Res.* 55: 1660).

The retroviral vector genomes of the present invention for subsequent use in gene therapy preferably contain the minimum retroviral material necessary to function efficiently as vectors. The purpose of this is to allow space for the incorporation of the homologous exogenous polypeptides, and for safety reasons. Retroviral vector genomes are preferably replication defective due to the absence of functional genes encoding one or more of the structural (or packaging) components encoded by the gag-pol and env genes. The absent components required for particle production are provided in trans in the producer cell. The absence of virus structural components in the genome also means that undesirable immune responses generated against virus proteins expressed in the target cell are reduced or avoided. Furthermore, possible reconstruction of infectious viral particles is preferably avoided where in vivo use is contemplated. Therefore, the viral structural components are preferably excluded from the genome as far as possible, in order to reduce the chance of any successful recombination.

Retroviral Host/Producer Cells

The retroviral vector particles of the present invention are typically generated in a suitable producer cell. Producer cells are generally mammalian cells but can be, for example, insect cells. A producer cell may be a packaging cell containing the virus structural genes, normally integrated into its genome. The packaging cell is then transfected with a nucleic acid encoding the vector genome, for the production of infective, replication defective vector particles. Alternatively, the producer cell may be co-transfected with nucleic acid sequences encoding the vector genome and the structural components, and/or with the nucleic acid sequences present on one or more expression vectors such as plasmids, adenovirus vectors, herpes viral vectors or any method known to deliver functional DNA into target cells.

In one embodiment, the vector of the present invention is constructed from or is derivable from a lentivirus. This has the advantage that the vector may be capable of transducing non-dividing cells and dividing cells. Accordingly, in certain aspects of the instant invention, the retroviral vectors of the invention are lentivirus vectors such as HIV or EIAV vectors. These have the advantages noted above.

Use of Codon Degeneracy to Reduce Homologous Recombination in Vectors Comprising IRES and Carcinoembryonic Antigen (CA) Sequences The methods of the present invention can also be applied to reduce homologous recombination events caused by homologous natural domains found within, e.g., IRES and carcinoembryonic antigen (CA) sequences. Both IRES and CA have replicated domains within their sequences that could lead to deletion of such sequences. Accordingly, the use of codon degeneracy in synthesis of vectors containing such nucleic acid sequences can prove advantageous for the same reasons described infra for CIR production. Highly homologous natural domains within distinct polypeptides are also a concern for vectors that comprise e.g., TCR-☐ and TCR-☐ in same vector with an IRES, if homology between them is significant—in such instances, one molecule can comprise multiple repeated domains, with two such genes joined by an IRES.

Pharmaceutical Compositions

In certain embodiments, the present invention provides a pharmaceutical composition for treating an individual by gene therapy, wherein the composition comprises a therapeutically effective amount of a retroviral vector according to the present invention. The pharmaceutical composition may be for human or animal usage. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Kits

In certain embodiments, the invention provides kits which contain, e.g., compositions of the invention as described herein and/or components specifically useful in the methods described herein. In other embodiments, the invention provides kits useful in the generation of vectors of the invention. For example, the pharmaceutical compositions of the invention can be included in a container, pack, or dispenser together with instructions for use.

EXAMPLES

The present invention is further detailed in the following examples, which are offered by way of illustration and are not intended to limit the invention in any manner. Standard techniques well known in the art or the techniques specifically described below are utilized.

General Methods

In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g. Sambrook, Fritsch and Maniatis, Molecular Cloning. Cold Spring Harbor Laboratory Press (1989); DNA Cloning, Vols. 1 and 2, (D. N. Glover, Ed. 1985); Oligonucleoide Synthesis (M. J. Gait, Ed. 1984); PCR Handbook Current Protocols in Nucleic Acid Chemistry, Beaucage, Ed. John Wiley & Sons (1999) (Editor), Oxford Handbook of Nucleic Acid Structure, Neidle, Ed., Oxford Univ Press (1999); PCR Protocols: A Guide to Methods and Applications, Innis et al., Academic Press (1990); PCI2 Essential Techniques: Essential Techniques, Burke, Ed., John Wiley & Son Ltd (1996); The PCR Technique. RT-PCR, Siebert, Ed., Eaton Pub. Although certain aspects of the present invention relate to compositions and uses of recombinant RNA retrovirus (e.g., lentiviral HIV-2, SIV, etc.), the molecular cloning may be done using proviral DNA clones, thus allowing the use of standard cloning techniques.

Site-directed mutagenesis in vitro by synthetic oligodeoxynucleotides can be carried out according to the method developed by Taylor et al. (*Nucleic Acids Res.* 13 (1985): 8749-8764) using the kit distributed by Amersham. Genetic fusions, especially of use in the synthesis of fusion proteins, e.g., CIRs, of the present invention can be made by art-recognized methods, e.g., gene SOE (splicing by overlap extension) methods that commonly rely upon the use of fusion primers (which are optionally mutagenic) during PCR amplification. (Horton et al. 1989 *Gene* 77: 61-68; U.S. Pat. No. 5,023,171).

Enzymatic amplification of DNA fragments by the so-called PCR technique (polymerase-catalysed Chain Reaction, Saiki R. K. et al., *Science* 230 (1985) 1350-1354; Mullis K. B. and Faloona F. A., *Meth. Enzym.* 155 (1987) 335-350) can be carried out using a DNA thermal cycler (Perkin Elmer Cetus) according to the manufacturer's specifications.

Verification of the nucleotide sequences can be carried out by the method developed by Sanger et al., (*Proc. Natl. Acad. Sci. USA*, 74 (1977): 5463-5467) using the kit distributed by Amersham. Verification of whether a homologous recombination event has occurred between two homologous polypeptides that were and likely still are contained within a single vector of the present invention may be performed by any art-recognized method, including but not limited to, Northern blot and/or RT-PCR methods (e.g., if assessed directly within isolated retroviral genomes), Southern blot and/or PCR methods (e.g., if assessed upon host cell genomic DNAs comprising integrated retroviral vectors), and SDS-PAGE followed by Western blot and/or immunoprecipitation followed by SDS-PAGE and detection of labeled polypeptides (e.g., if homologous polypeptides are of discernible sizes and/or contain distinguishable domains, features and/or epitopes).

Example 1

Use of the present invention to develop "designer T cells" initially involved the use of two nine-mer immunodominant CTL epitopes derived from JCV VP1 proteins (termed p36 and p100) in HLA-A0201+ subjects to expand JCV-specific T cells from an HLA-A0201+ PML survivor. Following this expansion of JCV-specific T cells, cell sorting was performed to identify and isolate p36 or p100/HLA-A0201 tetramer-positive cells. Two cell populations, one specific to p36 and another specific to p100, were subjected to TCR cloning. Two distinct dominant alpha ($\alpha$) chains (Va6 and Va12) and a unique beta ($\beta$) chain (Vb5.1) were cloned from the p36-specific cell line, while only one alpha (Va8.6) and one beta (Vb2) chain were dominant in the p100-specific line. DNA constructs encoding chimeric immune receptors (CIRs) were created comprising the extracellular domains of TCR alpha and beta chains fused to the transmembrane and cytoplasmic portions of CD3zeta (these CIRs were designated VaCaCD3z or VbCbCD3z, respectively). Recombinant retroviruses encoding each of the CIRs were then constructed. Each pair of alpha and beta chains in CIR format (two pairs for p36 due to two alpha chains and one pair for p100) were subjected to cellular expression and screened for specific binding of the peptide-HLA-A0201 tetramer. This screening confirmed the reactivity of the p100 TCRab and of one of the two pairs of p36 TCRab (Va12 and Vb5.1). Having established the successful isolation and expression of JCV-specific TCRs, functional tests of the CIRs in human T cells were performed, including assessment of T cell activation, cytokine expression and cytotoxic potency on contact with JCV antigen positive target cells. (Yang et al. 2005 *J. Neuro Virology* 11(Suppl. 2): 124).

Retroviral vectors encoding these anti-JCV CIRs (see FIG. 25, diagrams 1-3 (Tctv-anti-JCV p36Z CIR, Tcsv-anti-JCV p36Z CIR and Tcsv-anti JCV p3628Z CIR)), were then also constructed for purpose of testing two chain two vector (Tctv) and two chain single vector (Tcsv) approaches. Such retroviral vectors were constructed using art-recognized methods for synthesis of nucleic acid sequences encoding fusion proteins. However, in the Tcsv approach, one or both nucleic acid sequences encoding the cytoplasmic CD3$\zeta$ domain common to and encoding an identical polypeptide within both anti-JCV p36Z CIR and anti JCV p3628Z CIR nucleic acid sequences were subjected to mutagenesis using degenerate codon usage, for purpose of reducing the nucleic acid sequence identity of this domain between the two CIRs of the single vector. Human T cells containing the Tctv CIRs and Tcsv CIRs were then tested for expression of such CIRs in mammalian cells.

Example 2

It was demonstrated that CIR-T cells can mediate antiviral activity against HIV-1 in cells that are resistant to class I-restricted CTL-mediated activity. Furthermore, CIR-T cells can suppress virus in multiple cell types, including monocytes, dendritic cells, and lymphocyte-dendritic cell clusters. These results showed that T cells can be redirected against novel targets, and that independence from the class I pathway can have distinct advantages. (See Ma et al, 2002, for review.)

Example 3

Construction of vectors containing CIR nucleic acid sequences involved the mutation of a number of genes, with such mutations performed in order to exploit the degeneracy of the genetic code, thereby reducing homologous recombination in vectors that contain two or more CIR molecules encoding for highly homologous polypeptide sequences (e.g., highly homologous proteins and/or polypeptide domains within CIR polypeptide sequences). Genes that were altered at the nucleotide level include: CD3$\zeta$ (refer to the exemplary mutated CD3$\zeta$ nucleic acid sequence shown in FIG. 1, which comprises a partial extracellular domain-TMD-intracellular domain sequence of mutated CD3$\zeta$); CD28 (refer to the exemplary mutated CD28CD3$\zeta$ nucleic acid sequence shown in FIG. 3, which comprises a partial extracellular domain-TMD-intracellular domain sequence of mutated CD28 and an intracellular (cytoplasmic) domain of mutated CD3$\zeta$); and Fc$\epsilon$RI$\gamma$ (refer to the exemplary mutated hFc$\epsilon$RI$\gamma$ nucleic acid sequence shown in FIG. 5, which comprises a partial extracellular domain-TMD-intracellular domain sequence of mutated human Fc$\epsilon$RI$\gamma$). The preceding mutated sequences were used to produce the retroviral vector constructs shown in FIGS. 7-10. Construction of these vectors was performed by art-recognized methods of vector and/or fusion protein construction.

Example 4

Figure 11:
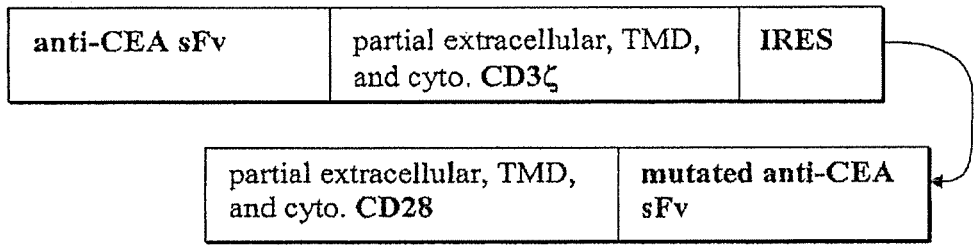
FIG. 11 depicts a schematic diagram of a viral vector comprising sequences encoding two chimeric immune receptor (CIR) polypeptides linked by an IRES sequence. Sequence encoding the first polypeptide comprises native sequences encoding anti-CEA sFv, fused to the partial extracellular domain, TMD and cytoplasmic domain of CD3ζ. Sequence encoding the second polypeptide comprises mutated sequence (using degenerate codon sequences) that encodes anti-CEA sFv fused to native sequence encoding the partial extracellular domain, TMD and cytoplasmic domain of CD28.
Figure 27:
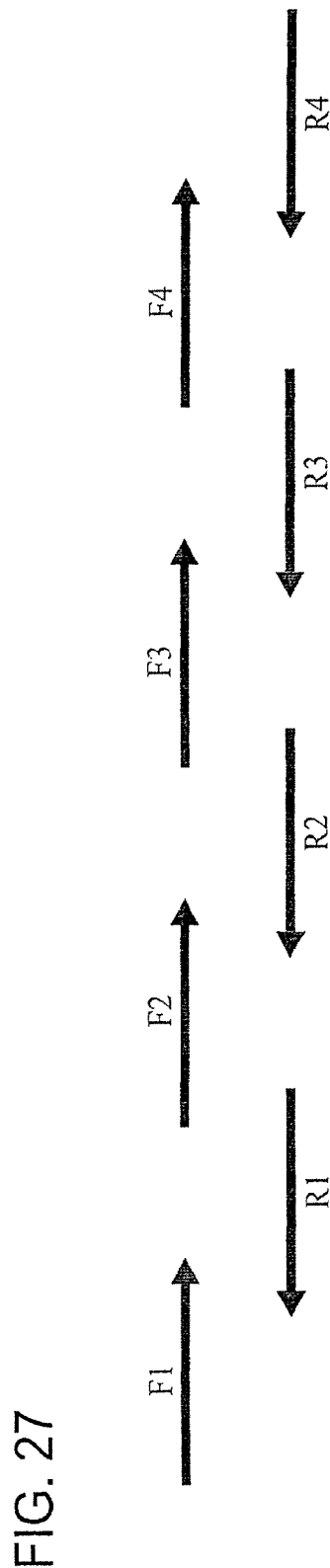
FIG. 27 depicts a schematic diagram of the eight overlapping primers used in PCR to produce a DNA fragment of mutated CD3ζ (muZ) that comprises degenerate codons yet encodes the native TMD and cytoplasmic domain polypeptide sequences of human CD3ζ.
Figure 28:
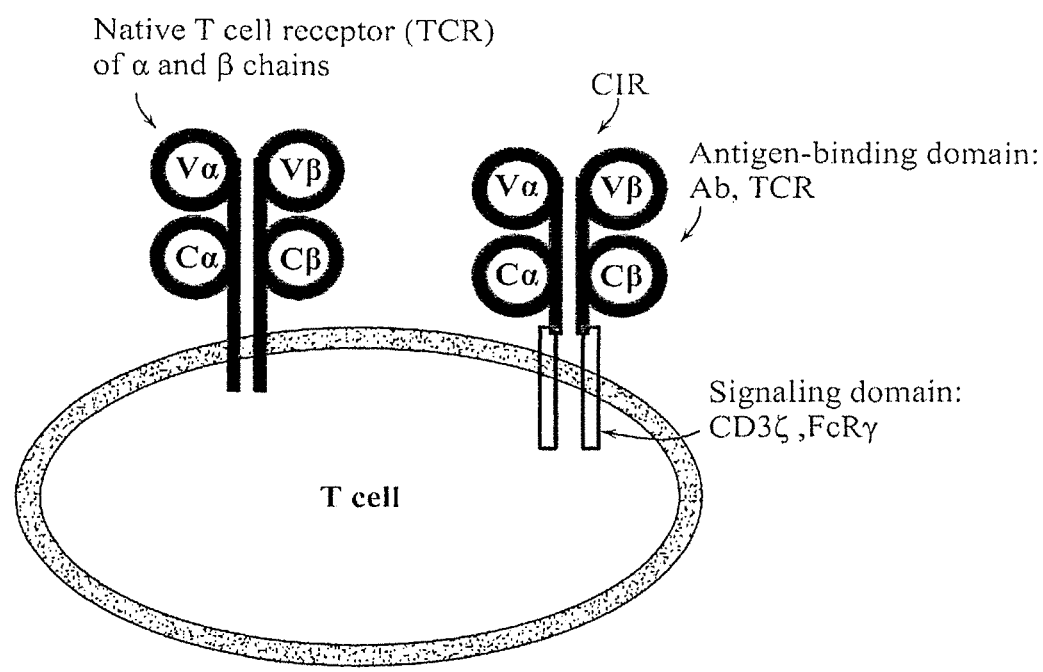
FIG. 28 depicts a model of a chimeric immune receptor (CIR) molecule, located at the plasma membrane of a "designer T cell."
Figure 29:
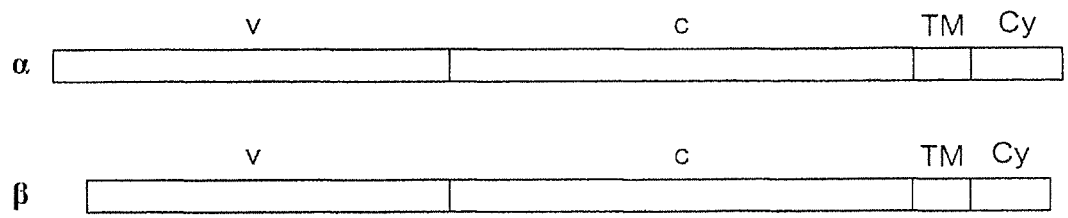
FIG. 29 depicts a schematic diagram showing the domain structure of TCR α and TCR β chain polypeptides.
Figure 30:
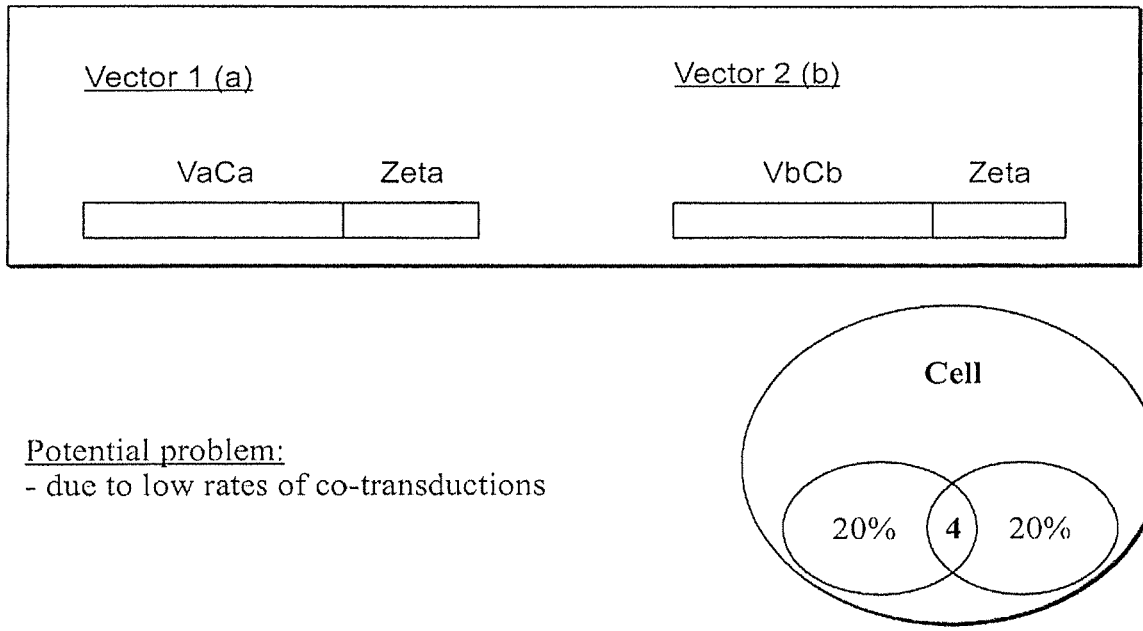
FIG. 30 depicts a schmatic diagram of a two-chain two-vector (Tctv) approach to CIR use, and displays a Venn diagram illustrating certain problems associated with such approaches, as they are reliant upon the occurrence of two different transfection and/or transformation events of potentially low probability.
Figure 31:
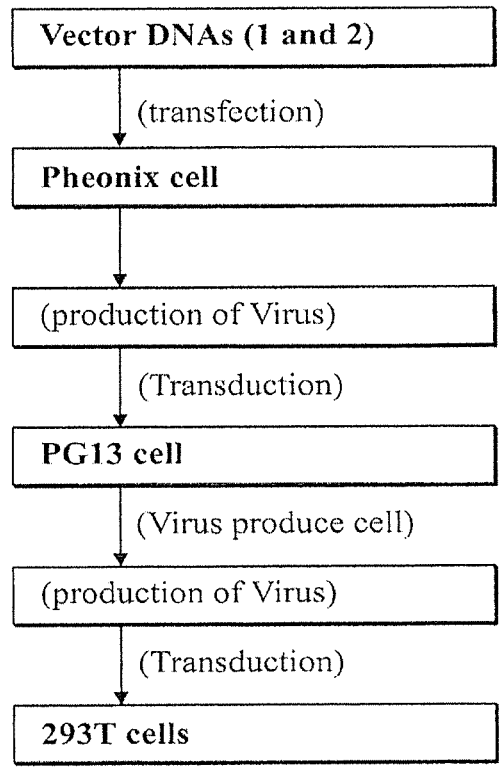
FIG. 31 depicts a flow chart showing the viral transduction procedure.
Figure 32:
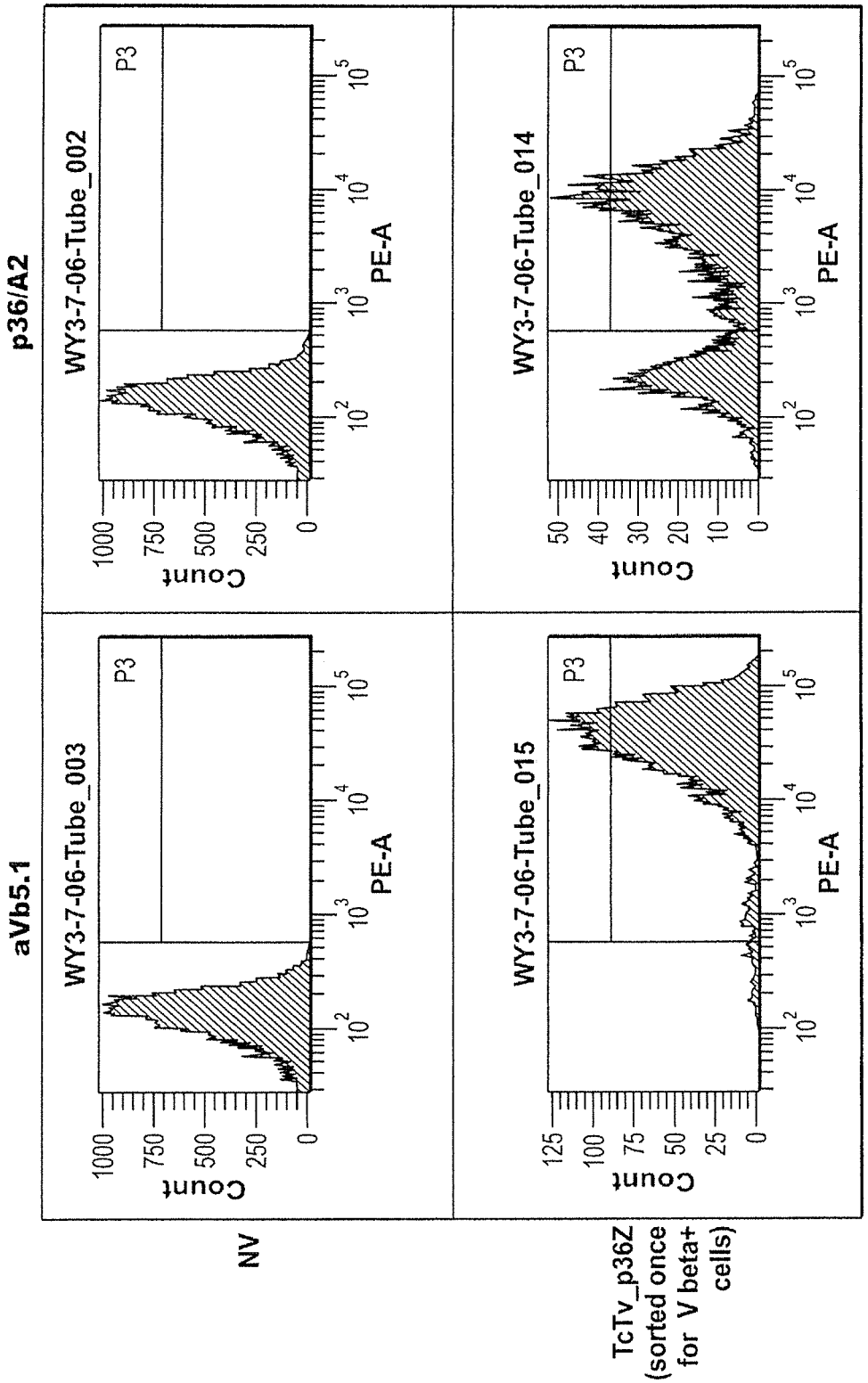
FIG. 32 shows cell sorting results demonstrating that some cells transduced with Tctv CIRs of TCR α and TCR β chains express the β chain on the cell surface but are not bound by the α chain antigen, P36/A2, indicating a lack of TCR α chain expression in these cells.
Figure 35:
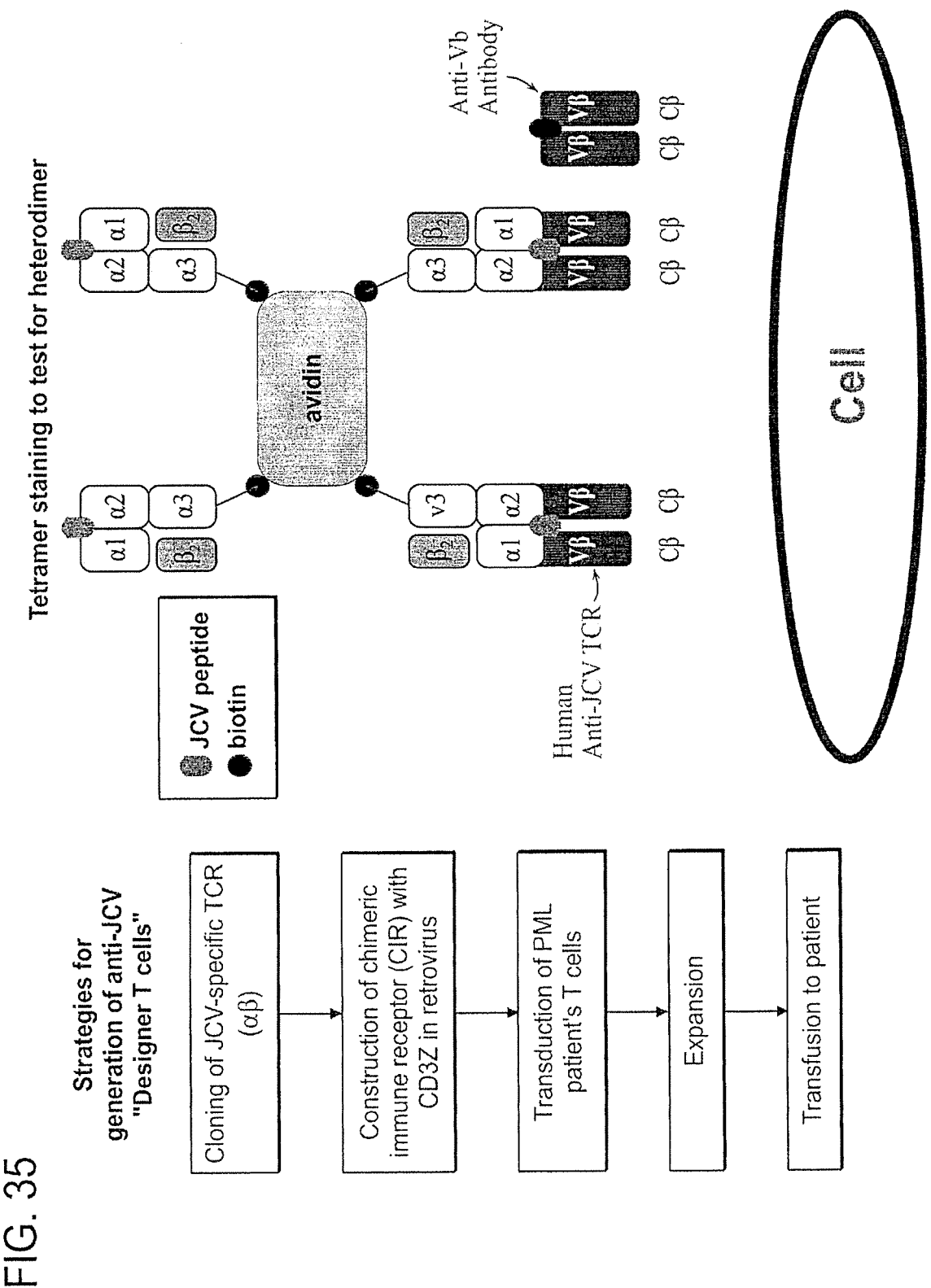
FIG. 35 is a schematic of strategies for generation of anti-JVC designer T cells and tetramer staining to test for heterodimer.
Figure 39:
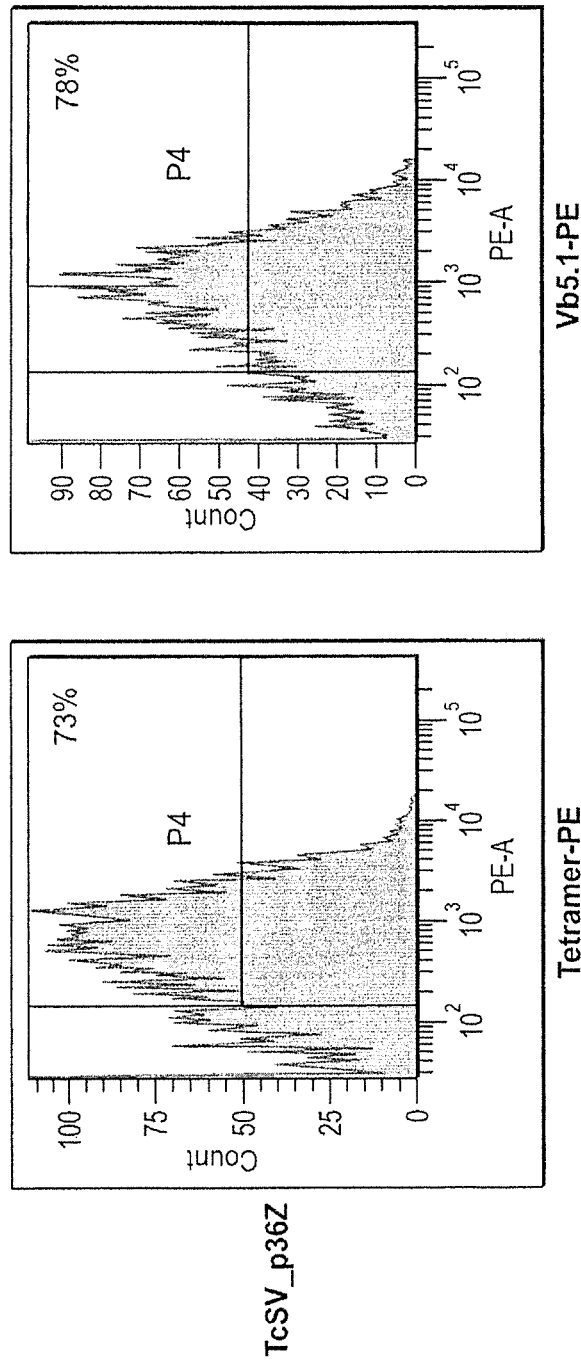
FIG. 39 shows the results of transfection and transducing of TcTv TcSv which were run in parallel with equal ratio chains used for transfection and the alignment of nucleotide sequences of chimeric CD28CD3Zeta (SEQ ID NO: 33) with mutated chimeric CD28CD3Zeta (SEQ ID NO: 34). The corresponding nucleotide sequences encoding partial CD28 and CD3Zeta are from native human CD28.
Figure 43:
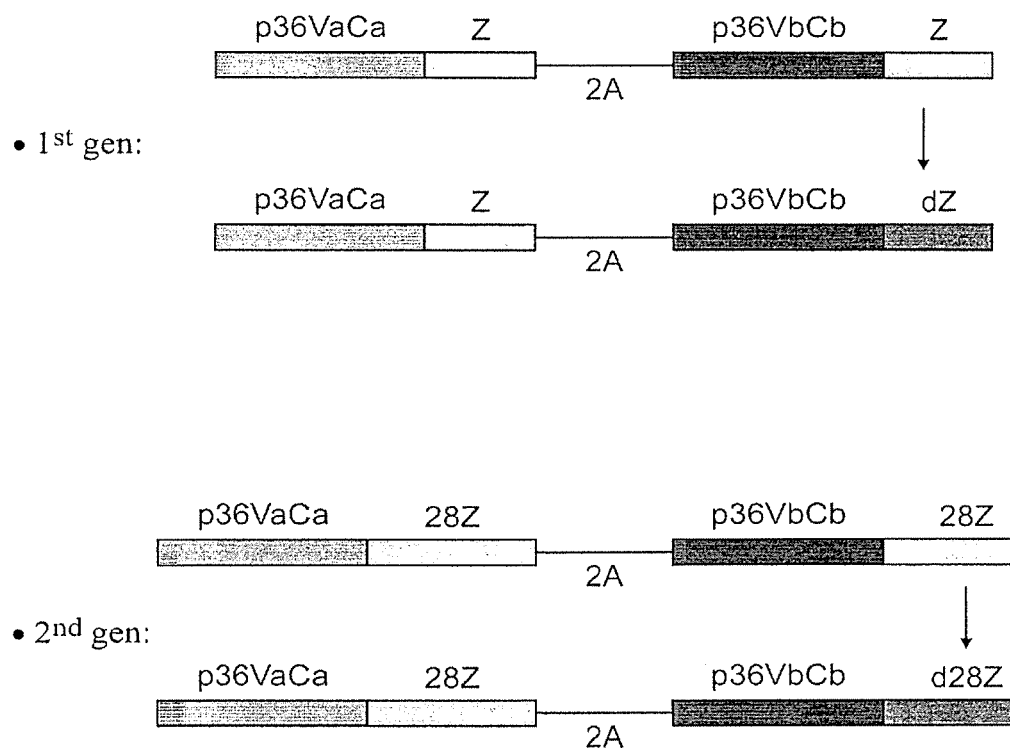
FIG. 43 show degenerate codon TcSv anti-JCV TCRs.
Figure 44:
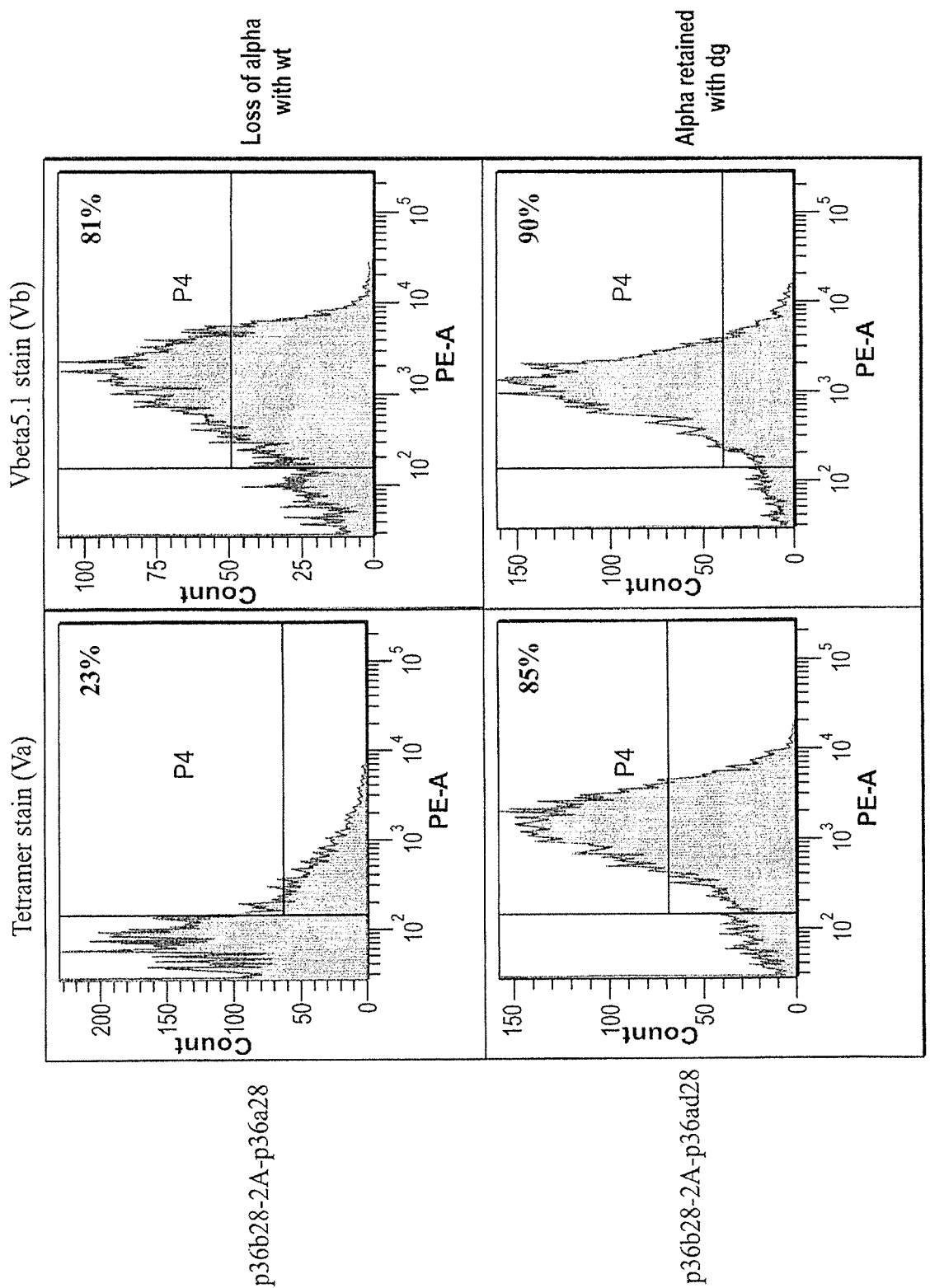
FIG. 44 shows the results of tetramer staining for degenerate codon TcSv anti-JCV TCR expression.
Figure 44:
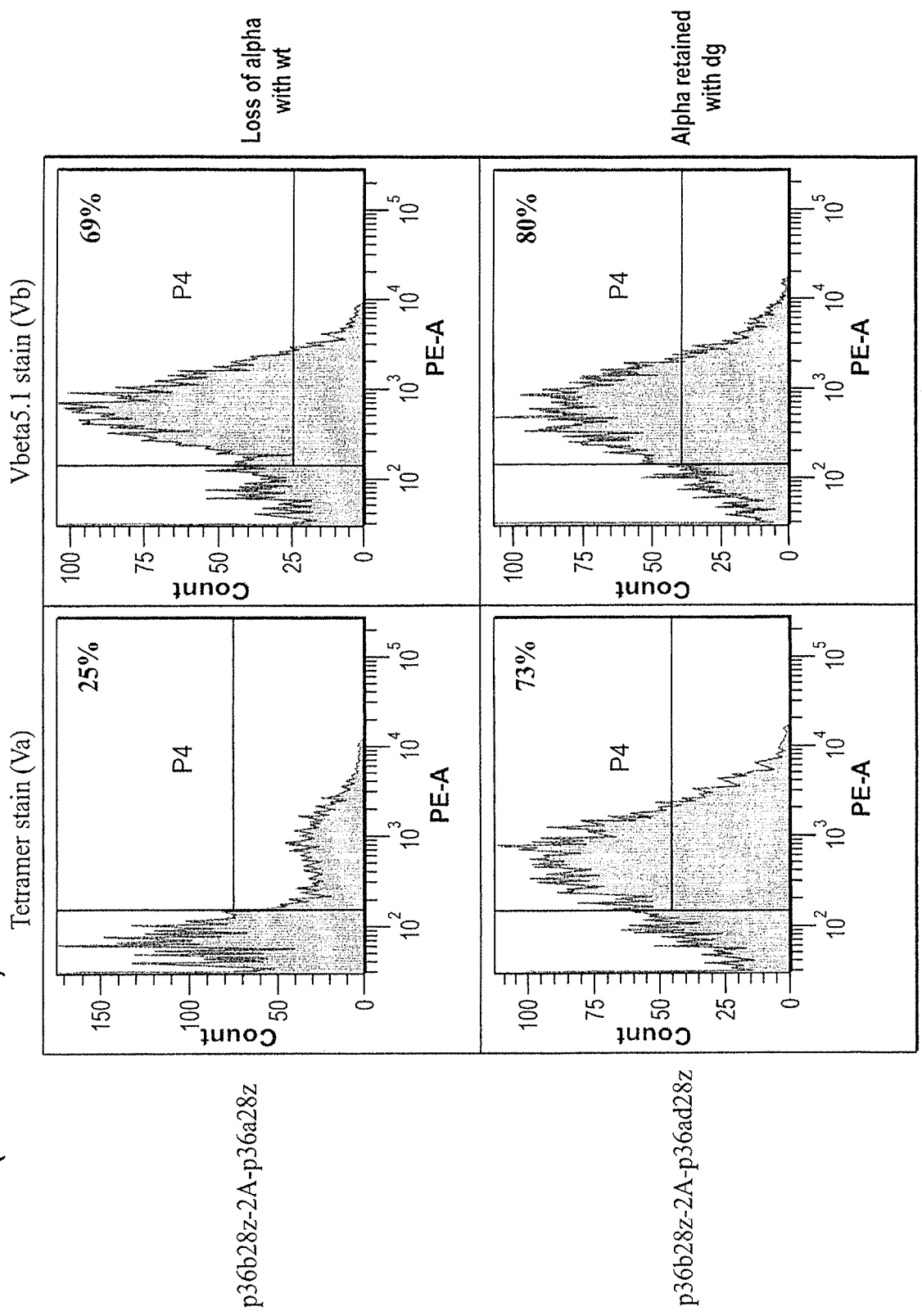

Vectors containing CIR nucleic acid sequences are also constructed to include human CD4, anti-CEA sFv and anti-PSMA sFv sequences. Mutated nucleic acid sequences that encode the signal peptide and extracellular domain polypeptides of human CD4 were generated (refer to FIG. 21). Mutated forms of anti-CEA sFv and anti-PSMA sFv sequences are readily constructed by applying the methods of degenerate codon usage described infra to the sequences of anti-CEA sFv (Nolan et al. 1999 *Clin Cancer Res.* 5: 3928-41) and anti-PSMA sFv (Ma et al. 2004 *Prostate* 6:

12-25). Mutated sequences of human CD4, anti-CEA sFv, and anti-PSMA sFv are used in combination with non-mutated forms of such sequences to synthesize retroviral vectors containing both mutated and non-mutated forms of such sequences (e.g., one such viral vector construct is schematically depicted in FIG. 11). Construction of such vectors is performed using art-recognized methods of vector and/or fusion protein construction.

Example 5

To perform immunotherapy using designer T cells that contain anti-JCV p36 and anti-JCV p100 CIR molecules, the following procedures can be implemented. First, mutated CD28Z-MFG based anti-JCV TCRCIR vectors are created that contain either alpha and beta chains of an anti-JCV p36 antibody or alpha and beta chains of an anti-JCV p100 antibody. For anti-JCV p36, the vector VaCaCD28Z-IRES-VbCbmuCD28Z-MFG (henceforth referred to as "tcp36muCD28Z") is generated, while for anti-JCV p100, the vector VaCaCD28Z-IRES-VbCbmuCD28Z-MFG (henceforth referred to as "tcp100muCD28Z") is made. Both vectors are constructed using art-recognized methods of vector and/or fusion protein construction. Second, Phoenix cells (a 293 cell derivative line with high calcium phosphate transfection efficiency; mix of ampho and ecto) are transfected with either the tcp36muCD28Z or tcp100muCD28Z vector. Third, PG13 cells (viral producing cells; VPCs) are infected with viral supernatants (containing viral virions) of the transfected Phoenix cells. Fourth, Jurkat T cells are transduced with viral supernatants of the cultured PG13 cells that have been infected with virus encoding either the tcp36muCD28Z or the tcp100muCD28Z CIR polypeptide. Fifth, transduced Jurkat T cells are subjected to FACS-based sorting to identify TCRVb5$^+$ (for tcp36muCD28Z) or TCRVb2$^+$ (for tcp100muCD28Z) cells that also bind specific PE-labeled anti-human TCRVb antibodies (native Jurkat cells are negative for both TCRVb2 and Vb5). Sixth, possible viral recombination events are evaluated by generating (from sorted cells) and then selecting 15-20 Jurkat T cell clones that are TCRVb5.1$^+$ (for tcp36muCD28Z-transduced) or TCRVb2$^+$ (for tcp100muCD28Z-transduced), isolating genomic DNAs from such T cell clones, and subjecting these genomic DNAs to amplification as PCR templates using specific primers designed to match sequences immediately upstream of the VaCaCD28Z and immediately downstream of VbCbmuCD28Z, respectively. Changes in amplification product sizes derived from individual clones will reflect the occurrence of any recombination events, while the absence of such alterations will verify that no such events have occurred.

Once Jurkat T cell clones that are TCRVb5.1$^+$ (for tcp36muCD28Z-transduced) or TCRVb2$^+$ (for tcp100muCD28Z-transduced) are generated, isolated and verified in the above manner, such cells are optionally subjected to tests for binding function and/or activity in inducing cytokine secretion. An exemplary binding assay for such Jurkat T cells is a tetramer binding assay in which the Jurkat cells are stained with PE-p36/HLA-A0201 tetramer or PE-p100/HLA-A0201 tetramer, then subjected to FACS analysis to determine whether the labeled p36 or p100 antigen-containing tetramer has bound. Additionally and/or alternatively, such Jurkat cells can be subjected to an exemplary cytokine secretion assay to identify those cells expressing functionally active CIRs, with such assays involving co-culture of the TCRVb5.1$^+$ (for tcp36muCD28Z-transduced) or TCRVb2$^+$ (for tcp100muCD28Z-transduced) Jurkat cells with HLA-A0201$^+$ B cells in the presence of peptide (antigen) p36 or p100. Jurkat cells expressing functional CIR molecules can then be identified by assessing the cultured supernatant for IL-2 or IFNγ cytokines.

Finally, once CIR-positive cells are identified that have not undergone recombination events between the nucleic acid sequences encoding highly homologous CIR polypeptides, human PBMC cells are transduced with viral supernatant from PG13 cells that contain either tcp36muCD28Z or tcp100muCD28Z. Transduced human (PBMC) T cells are then tested for their in vivo function as an effective immunotherapy capable of, e.g., killing target cells, inducing cytokine secretion and proliferation upon antigen stimulation, reducing JCV titer in a subject, reducing morbidity and/or mortality in a JCV-infected subject, etc.

Example 6

The approach described in Example 5 is readily applied to achieve gene therapy and/or immunotherapy of a number of diseases and/or disorders. For example, immunotherapy for infectious disease or cancer that uses retrovirally-transduced T cells that express antigen-specific CIRs can be employed with the following exemplary CIR-containing vector constructs:

anti-JCV TCRVaCaCD28CD3Z-IRES-anti-JCV TCRVbCbmuCD28muCD3Z (refer to FIG. 7);
anti-JCV TCRVaCaCD3Z-IRES-anti-JCV TCRVbCbmuCD3Z (refer to FIG. 8);
anti-JCV TCRVaCaFC(e)RIγ-IRES-anti-JCV TCRVbCbmuFC(e)RIγ (refer to FIG. 9);
anti-CEA sFV-CD28CD3Z-IRES-anti-PSMA sFV-muCD28muCD3Z (refer to FIG. 10); and
anti-CEA sFV-CD3Z-IRES-mu anti-CEA sFV-CD28 (refer to FIG. 11).

Example 7

Retroviral Vectors Encoding Anti-JC Virus Chimeric T Cell Receptors with Degenerate Codons Progressive multifocal leukoencephalopathy (PML), is a rare and usually fatal viral disease that is characterized by progressive damage or inflammation of the white matter of the brain at multiple locations. It occurs almost exclusively in people with severe immune deficiency, e.g. transplant patients on immunosuppressive medications, or AIDS patients.

The cause of PML is a type of polyomavirus called the JC virus (JCV), after the initials of the patient in whom it was first discovered. The virus is widespread, with 86% of the general population presenting antibodies, but it usually remains latent, causing disease only when the immune system has been severely weakened.

The immune response to JCV could be humoral. 90% adults have anti-JCV IgG but the humoral immune response is unable to prevent PML.

The cellular immune response is mediated by CD8+ T cells. The presence of JCV-specific CTL is associated with long-term survival in HIV+/PML patients.

Two JCV VP1 derived nonamer peptides (P36 and P100) have been shown to be immunodominant.

Described herein is the creation of anti-JC virus (JCV) chimeric T cell receptors (cTCRs) to redirect autologous T cells to recognize and lyse JCV infected cells for therapy in progressive multifocal leukoencephalopathy (PML), a demyelinating AIDS-associated brain disease. These cTCRs are engineered with JCV specific TCRa and TCRb chains, each fused to the transmembrane (TM) and cytoplasmic (cyt) domains of CD3zeta. Both chains are co-expressed in recipient T cells to create a functional TCR. As shown herein, co-expression of two partially homologous chimeric immune receptors (CIRs) in a retroviral vector (two chain single vector, tcsv) led to recombination-deletion between repeated sequences, excising the equivalent of one of the CIRs. Also shown herein is that cells could be transduced with separate chains in two vectors (called two chain two vector (tctv). This arrangement displayed poor cell co-expression due to low probability of co-transduction from two separate retroviral vectors. In an effort to improve co-transduction, a novel type of tcsv anti-JCV cTCR that would resist this deletion process was designed. To suppress the potential for homologous recombination in the tcsv format, mutagenesis was applied to create codon degeneracy to minimize sequence homology between the repeated CD3zeta domains while preserving the final protein sequence. This strategy showed co-expression of chains as expected. A redesign of the tcsv configuration is underway to allow a definitive measurement of the actual efficiency of the deletion suppression.

CONCLUSION

TcTv format resulted in low cell co-expression due to low probability of same cell transduction.

TcSv format enabled same cell transduction and co-expression but required engineering of degenerate nucleotides in repeated sequence to prevent homologous recombination and deletion.

Degenerate nucleotide TcSV format enabled high-level coexpression.

Thus, provided herein is a new approach for T cell Therapy for PML, that is and anti-JCV "designer T cell" therapy, using ex vivo expansion of T cells transduced with anti-JCV TCRs.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A retroviral vector comprising:
a first nucleic acid sequence that encodes a first polypeptide sequence and a second nucleic acid sequence that encodes a second polypeptide sequence, wherein:
(a) the first polypeptide sequence and the second polypeptide sequence comprise an identical polypeptide sequence of greater than 15 amino acids in length; and
(b) the first nucleic acid sequence and the second nucleic acid sequence contain at least one non-identical codon within the codons that encode the identical polypeptide sequence of the first and second nucleic acid sequences; and
(c) one of the first or second nucleic acid sequences is selected from the group consisting of:
(1) a nucleic acid comprising at least 95% sequence identity to the polynucleotide sequence of SEQ ID NO:1;
(2) a nucleic acid comprising at least 95% sequence identity to the polynucleotide sequence of SEQ ID NO:4;
(3) a nucleic acid comprising at least 95% sequence identity to the polynucleotide sequence of SEQ ID NO:7;
(4) a nucleic acid comprising at least 95% sequence identity to the polynucleotide sequence of SEQ ID NO:16;
(5) a nucleic acid comprising at least 95% sequence identity to the polynucleotide sequence of SEQ ID NO: 20; and
(6) a nucleic acid comprising at least 95% sequence identity to the polynucleotide sequence of SEQ ID NO:22.

2. A retroviral vector comprising:
a first nucleic acid sequence that encodes a first polypeptide sequence and a second nucleic acid sequence that encodes a second polypeptide sequence, wherein:
(a) the first polypeptide sequence comprises a polypeptide sequence of greater than 15 amino acids in length that is greater than 90% identical to the second polypeptide sequence;
(b) the first nucleic acid sequence and the second nucleic acid sequence contain at least one non-identical codon that encodes an identical amino acid residue, wherein the greater than 90% identical polypeptide sequence of the first and second nucleic acid sequences comprises the identical amino acid residue; and (c) one of the first or second nucleic acid sequences is selected from the group consisting of:
   (1) a nucleic acid comprising at least 95% sequence identity to the polynucleotide sequence of SEQ ID NO:1;
   (2) a nucleic acid comprising at least 95% sequence identity to the polynucleotide sequence of SEQ ID NO:4;
   (3) a nucleic acid comprising at least 95% sequence identity to the polynucleotide sequence of SEQ ID NO:7;
   (4) a nucleic acid comprising at least 95% sequence identity to the polynucleotide sequence of SEQ ID NO:16;
   (5) a nucleic acid comprising at least 95% sequence identity to the polynucleotide sequence of SEQ ID NO: 20; and
   (6) a nucleic acid comprising at least 95% sequence identity to the polynucleotide sequence of SEQ ID NO:22.

3. The retroviral vector of claim 1, wherein the retroviral vector is selected from the group consisting of avian sarcoma-leukosis virus (ASLV), murine leukemia virus (MLV), human-, simian-, feline-, and bovine immunodeficiency viruses (HIV, SIV, FIV, BIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), MFG, FBR murine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV), AKR (endogenous) murine leukemia virus, Avian carcinoma, Mill Hill virus 2, Avian leukosis virus—RSA, Avian myeloblastosis virus, Avian myelocytomatosis virus 29, Bovine syncytial virus, Caprine arthritis encephalitis virus, Chick syncytial virus, Equine infectious anemia virus, Feline leukemia virus, Feline syncytial virus, Finkel-Biskis-Jinkins murine sarcoma virus, Friend murine leukemia virus, Fujinami sarcoma virus, Gardner-Arnstein feline sarcoma virus, Gibbon ape leukemia virus, Guinea pig type C oncovirus, Hardy-Auckerman feline sarcoma virus, Harvey murine sarcoma virus, Human foamy virus, Human spumavirus, Human T-lymphotropic virus 1, Human T-lymphotropic virus 2, Jaagsiekte virus, Kirsten murine sarcoma virus, Langur virus, Mason-Pfizer monkey virus, Mouse mammary tumor virus, Ovine pulmonary adenocarcinoma virus, Porcine type C oncovirus, Reticuloendotheliosis virus, Rous sarcoma virus, Simian foamy virus, Simian sarcoma virus, Simian T-lymphotropic virus, Simian type D virus 1, Snyder-Theilen feline sarcoma virus, Squirrel monkey retrovirus, Trager duck spleen necrosis virus, UR2 sarcoma virus, Viper retrovirus, Visna/maedi virus, Woolly monkey sarcoma virus, and Y73 sarcoma virus.

4. The retroviral vector of claim 1, wherein at least 20% of the codons that encode the at least one identical polypeptide domain of the first and second nucleic acid sequences are non-identical.

5. The retroviral vector of claim 1, wherein the first nucleic acid sequence and the second nucleic acid sequence are less than 80% identical within the codons that encode the at least one identical polypeptide domain of the first and second nucleic acid sequences.

6. The retroviral vector of claim 1, wherein at least one of the first and second polypeptide sequences is a chimeric immune receptor polypeptide sequence.

7. The retroviral vector of claim 6, wherein at least one of the first and second polypeptide sequences is a chimeric immune receptor polypeptide sequence comprising a signal sequence that directs the polypeptide to the cell surface.

8. The retroviral vector of claim 6, wherein the signal sequence that directs the polypeptide to the cell surface is selected from the group consisting of TCR-α, TCR-β, TCR-.gamma., IgG-Δ, IgG, IgA, IgM, IgE, IgD, CD2, CD4, CD8, CD28, CD3λ, FcεRIγ, and LFA-1.

9. The retroviral vector of claim 6, wherein at least one of the first and second polypeptide sequences is a chimeric immune receptor polypeptide sequence comprising an extracellular binding domain selected from the group consisting of a surface membrane polypeptide that binds specifically to at least one ligand and a secreted polypeptide that binds specifically to at least one ligand.

10. The retroviral vector of claim 6, wherein at least one of the first and second polypeptide sequences is a chimeric immune receptor polypeptide sequence comprising a transmembrane domain selected from the group consisting of TCR-α, TCR-β, TCR-γ, TCR-Δ, IgG, IgA, IgM, IgE, IgD, CD2, CD4, CD8, CD28, CD3ζ, FcεRIγ, and LFA-1.

11. The retroviral vector of claim 6, wherein both of the first and second polypeptide sequences is a chimeric immune receptor polypeptide sequence.

12. The retroviral vector of claim 7, wherein both of the first and second polypeptide sequences is a chimeric immune receptor polypeptide sequence.

13. The retroviral vector of claim 1 comprising a mutant nucleic acid sequence selected from the group consisting of SEQ ID NO:1, SEQ ID NO:4, SEQ ID NO:7, SEQ ID NO:16, SEQ ID NO:20 and SEQ ID NO:22.

14. A recombinant virus comprising the retroviral vector of claim 1.

15. A cell comprising the retroviral vector of claim 1.

16. The retroviral vector of claim 1 wherein: (a) the first polypeptide sequence and the second polypeptide sequence each comprises an identical single chain antibody polypeptide sequence or an antigen-binding fragment thereof and (b) the first nucleic acid sequence and the second nucleic acid sequence contain at least one non-identical codon within the codons that encode the identical single chain antibody polypeptide sequence or the antigen-binding fragment thereof.

17. The retroviral vector of claim 1 wherein: (a) the first polypeptide sequence and the second polypeptide sequence each comprises a TCR alpha chain and a TCR beta chain, respectively, or an antigen-binding fragment thereof and (b) the first nucleic acid sequence and the second nucleic acid sequence contain at least one non-identical codon within the codons that encode the first and the second polypeptide or the antigen-binding fragment thereof.

18. A pharmaceutical composition comprising the recombinant retrovirus of claim 1, and a pharmaceutically acceptable carrier.

19. A kit comprising a virus comprising the retroviral vector of claim 1, and instructions for use.

* * * * *